US009425409B2

(12) United States Patent
Schwaiger et al.

(10) Patent No.: US 9,425,409 B2
(45) Date of Patent: Aug. 23, 2016

(54) MATERIALS FOR ELECTRONIC DEVICES

(75) Inventors: Jochen Schwaiger, Darmstadt (AT);
Heinrich Becker, Ober-Ramstadt (DE)

(73) Assignee: Merck Patent GmbH (DE)

( * ) Notice: Subject to any disclaimer, the term of this patent is extended or adjusted under 35 U.S.C. 154(b) by 663 days.

(21) Appl. No.: 13/878,332

(22) PCT Filed: Sep. 8, 2011

(86) PCT No.: PCT/EP2011/004529
§ 371 (c)(1),
(2), (4) Date: Apr. 25, 2013

(87) PCT Pub. No.: WO2012/045384
PCT Pub. Date: Apr. 12, 2012

(65) Prior Publication Data
US 2013/0207048 A1    Aug. 15, 2013

(30) Foreign Application Priority Data
Oct. 9, 2010   (DE) .................. 10 2010 048 074

(51) Int. Cl.
*H01L 51/54*    (2006.01)
*C09K 11/06*    (2006.01)
*H01L 51/00*    (2006.01)
*H01L 51/50*    (2006.01)
*C07D 487/04*   (2006.01)

(52) U.S. Cl.
CPC ......... *H01L 51/0072* (2013.01); *C07D 487/04* (2013.01); *H01L 51/0052* (2013.01); *H01L 51/0058* (2013.01); *H01L 51/5072* (2013.01)

(58) Field of Classification Search
None
See application file for complete search history.

(56) References Cited

U.S. PATENT DOCUMENTS

| 2007/0131929 | A1  | 6/2007  | Bae et al. | |
|---|---|---|---|---|
| 2011/0127513 | A1* | 6/2011  | Lee ..................... | C07D 401/04 257/40 |
| 2011/0284799 | A1  | 11/2011 | Stoessel et al. | |
| 2015/0018549 | A1  | 1/2015  | Knowles et al. | |

FOREIGN PATENT DOCUMENTS

| JP | 2001043978 A | 2/2001 | | |
|---|---|---|---|---|
| JP | 2009-516652 A | 4/2009 | | |
| JP | 2009-526071 A | 7/2009 | | |
| KR | WO 2010062065 A2 * | 6/2010 | ........... | C07D 401/04 |
| KR | WO 2011010842 A2 * | 1/2011 | ............ | C09K 11/06 |
| WO | WO-2007/095118 A2 | 8/2007 | | |
| WO | WO-2008142635 A2 | 11/2008 | | |
| WO | WO-2010/086089 A1 | 8/2010 | | |

OTHER PUBLICATIONS

Machine translation of JP2001-043978. Date of publication: Feb. 16, 2001.*
Adam, Jean-Marie, et al., "Arylierungen von Cyclischen Guanidin-Analogen mit α-Halogenierten Anthrachinonen: Neue Anthrapyrimidine", Helvetica Chimica Acta, vol. 65, No. 227, (1982), pp. 2318-2325.
Avendano, C., et al., "Product Class 10: Anthraquinone and Phenanthrenedione Imines and Diimines", Science of Synthesis, vol. 28, (2006), pp. 735-806.
International Search Report for PCT/EP2011/004529 mailed Mar. 9, 2012.
Korshak, et al., "Synthesis and Investigation of New Highly Fused Polyheteroarylenes", Macromolecules, vol. 9, No. 4, pp. 626-632 (1976).
Austin et al., "Facile Synthesis of Ethynylated Beszole Acid Derivatives and Aromatic Compounds via Ethynyltrimethylsilane", J. Org. Chem., vol. 46, pp. 2280-2286 (1981).
Niume et al., "Novel Thermostable Polymers from Bis-o-Aminophenylbenzimidazoles and Aromatic Tetracarboxylic Dianhydrides", Journal of Polymer Science, vol. 19, pp. 1745-1755 (1981).
Padmaja et al, "Reaction of 1,2-Dihydronaphth[1,2-d][3,1]oxazin-2,4(H)-dione with ortho-Substituted Anilines", Indian Journal of Chemistry, vol. 26B, pp. 951-954 (1987).
Padmaja et al., "Reaction of 2-(1-Amino-2-naphthyl)benzimidazole with Aldehydes", Indian Journal of Chemistry, vol. 27B, pp. 418-420 (1988).
Devi et al., "Synthesis of 6,7-dihydro-6-suhstituted benzimidazo[1,2-c]benzo[g]quinazolines and their heteroaromatic analogues", Indian Journal of Chemistry, vol. 33B, pp. 1013-1016 (1994).
Sharma et al., "Synthesis of a Novel Structure Variant of Imidazoquinazoline with Three-Point Diversity[1]", Synthesis, vol. 11, pp. 1841-1847 (2006).
Shi et al., "An efficient synthesis of quinazoline-2,4-dione derivatives with the aid of a low-valent titanium reagent", Tetrahedron, vol. 63, pp. 9764-9773 (2007).
Dou et al., "One-Pot Synthesis of Quinazolinone Derivatives from Nitro-Compounds with the Aid of Low-Valent Titanium", J. Comb. Chem., vol. 11, pp. 151-154 (2009).

(Continued)

Primary Examiner — Andrew K Bohaty
(74) Attorney, Agent, or Firm — Drinker Biddle & Reath LLP

(57) ABSTRACT

The present invention relates to compounds of the formula (I)

to the use of the compounds in electronic devices, to processes for the preparation of the compounds, and to electronic devices comprising the compounds, preferably as electron-transport materials, as hole-blocking materials, as matrix materials and/or as emitter materials.

11 Claims, No Drawings

(56) References Cited

OTHER PUBLICATIONS

Shi et al., "One-Pot Synthesis of Imidazo[1,2-c]Quinazolinone Derivatives from Nitro-Compounds Reduced by Zinc", *Journal of Heterocyclic Chemistry*, vol. 46, pp. 971-974 (2009).

Wang et al., "One-Pot Synthesis of Imidazo[1,2-c]Quinazolinone-5(6H)-thione and Imidazo[1,2-c]quinazolin-5(6H)-one with the Aid of Tin(II) Chloride", *Journal of Heterocyclic Chemistry*, vol. 46, pp. 1364-1368 (2009).

\* cited by examiner

MATERIALS FOR ELECTRONIC DEVICES

CROSS-REFERENCE TO RELATED APPLICATIONS

This application is a national stage application (under 35 U.S.C. §371) of PCT/EP2011/004529, filed Sep. 8, 2011, which claims benefit of German application 10 2010 048 074.6, filed Oct. 9, 2010 which are both incorporated by reference.

The present invention relates to compounds of the formula (I) and to the use thereof as functional materials in electronic devices, where the said devices are preferably used as electron-transport material, as hole-blocking material, as matrix material and/or as emitter material. The invention furthermore relates to processes for the preparation of the compounds of the formula (I) and to electronic devices comprising the compounds of the formula (I).

Organic semiconductor materials, such as the compounds according to the invention, are being developed for a number of different applications in electronic devices. The structure of organic electroluminescent devices (OLEDs) in which the compounds according to the invention can be employed as functional materials is described, for example, in U.S. Pat. No. 4,539,507, U.S. Pat. No. 5,151,629, EP 0676461 and WO 98/27136.

Further improvements are still necessary with respect to the performance data of the organic electroluminescent devices, in particular with a view to broad commercial use. Of particular importance in this connection are the lifetime, the efficiency and the operating voltage of the organic electroluminescent devices and the colour values achieved. In particular in the case of blue-emitting electroluminescent devices, there is potential for improvement with respect to the lifetime of the devices. Furthermore, it is desirable for the compounds for use as organic semiconductor materials to have high thermal stability and a high glass-transition temperature and to be sublimable without decomposition.

In particular in the case of the electron-transport materials available at present, improvements are desirable since the properties of the electron-transport material, in particular, also have a significant influence on the above-mentioned properties of the organic electroluminescent device. In particular, there is a demand for electron-transport materials which simultaneously result in good efficiency, a long lifetime and a low operating voltage.

In this connection, there is considerable interest in electron-transport materials which result in better electron injection into the emitting layer, since an electron-richer emission layer results in better efficiency. In addition, better injection enables the operating voltage to be reduced. In order to achieve this aim, the provision of novel electron-transport materials having improved properties is desirable.

Improvements are also desirable in the case of the hole-blocking materials known in the prior art, since they likewise have a significant influence on the above-mentioned properties of the organic electroluminescent device. In this connection, there is considerable interest in hole-blocking materials which, owing to the suitable position of their HOMO or LUMO energy levels, keep holes away from the electron-transport layer and keep them in the emission layer and at the same time transfer electrons from the electron-transport layer into the emission layer. In order to achieve this aim, the provision of novel materials is.

Furthermore, there is a demand for matrix materials for use in electronic devices. In particular, there is a demand for matrix materials for phosphorescent emitters which simultaneously result in good efficiency, a long lifetime and a low operating voltage. It is precisely the properties of the matrix materials that are frequently limiting for the lifetime and efficiency of the organic electroluminescent device.

In accordance with the prior art, carbazole derivatives, for example bis-(carbazolyl)biphenyl, are frequently used as matrix materials. There is still potential for improvement here, in particular with respect to the lifetime and glass-transition temperature of the materials. Furthermore, ketones (WO 04/093207), phosphine oxides and sulfones (WO 05/003253) are used as matrix materials for phosphorescent emitters. There is still potential for improvement here, in particular with respect to the efficiency and compatibility with metal complexes which contain ketoketonate ligands, for example acetylacetonate. Furthermore, metal complexes, for example BAlq or zinc(II) bis[2-(2-benzothiazolyl)phenolate], are used as matrix materials for phosphorescent emitters. There is still a need for improvement here, in particular with respect to the operating voltage and chemical stability. Purely organic compounds are frequently more stable than these metal complexes. Thus, some of these metal complexes are hydrolysis-sensitive, which makes handling the complexes more difficult.

For fluorescent OLEDs, the matrix materials used in accordance with the prior art, especially for blue-emitting electroluminescent devices, are especially condensed aromatic compounds, for example anthracene derivatives, for example 9,10-bis(2-naphthyl)anthracene (U.S. Pat. No. 5,935,721). WO 03/095445 and CN 1362464 disclose 9,10-bis(1-naphthyl)anthracene derivatives for use in OLEDs. Further anthracene derivatives are disclosed in WO 01/076323, WO 01/021729, WO 04/013073, WO 04/018588, WO 03/087023 or WO 04/018587. Matrix materials based on aryl-substituted pyrenes and chrysenes are disclosed in WO 04/016575. Matrix materials based on benzanthracene derivatives are disclosed in WO 08/145239. For high-quality applications, it is desirable to have available further matrix materials, which preferably have improved properties.

There continues to be a demand for fluorescent emitter materials for use in electronic devices. In particular, there is a demand for emitter materials which have high sublimation stability and deep-blue colour coordinates.

Prior art which may be mentioned in the case of blue-emitting compounds is the use of arylvinylamines (for example WO 04/013073, WO 04/016575, WO 04/018587). However, these compounds are thermally unstable and cannot be evaporated without decomposition, which requires high technical complexity for OLED production and thus represents a technical disadvantage.

In the area of nitrogen-containing heteroaromatic compounds for use in organic electroluminescent devices, the following documents should be cited as prior art.

The patent applications WO 2008/145239 and US 2007/0131929 disclose compounds for use in organic electroluminescent devices in which an electron-deficient heteroaromatic unit, such as, for example, a benzimidazole unit or a benzodiazine unit, is bonded in the periphery of the aromatic system.

The patent application JP 2001-43978 discloses diazaindolizine derivatives and imidazoquinazoline derivatives for use in organic electroluminescent devices.

However, there continues to be a demand for heteroaromatic compounds for use in the said devices. In particular, there is a demand for compounds which have an extended aromatic or heteroaromatic system and therefore have improved properties as functional materials in organic electroluminescent devices. Particularly relevant desired material properties are a high glass-transition temperature and good film-formation properties.

In the course of the present invention, it has now been found that compounds of the formula (I) containing an imidazoquinazoline group are highly suitable for use as functional materials in organic electroluminescent devices.

The invention thus relates to a compound of the formula (I) which has precisely one ring A, B or C,

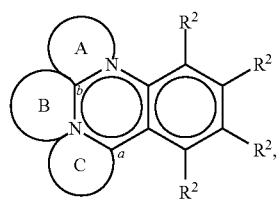

formula (I)

where ring A has a structure of the formula (Ia)

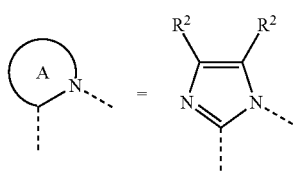

formula (Ia)

and ring B has a structure of the formula (Ib)

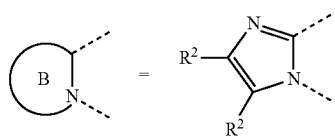

formula (Ib)

and ring C has a structure of the formula (Ic)

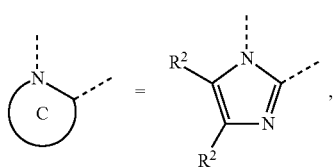

formula (Ic)

and, if ring A or ring B occurs, a group $R^1$ is bonded in position a of formula (I) and, if ring C occurs, a group $R^1$ is bonded in position b of formula (I),
and furthermore:

$R^1$ is H, D, F, Cl, Br, I, CHO, $N(R^3)_2$, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OS(=O)_2R^3$, $SO_3H$, $C(=O)OR^3$, $OR^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $-R^3C=CR^3-$, $-C\equiv C-$, $Si(R^3)_2$, $Ge(R^3)_2$, $Sn(R^3)_2$, C=O, C=S, C=Se, $C=NR^3$, $P(=O)(R^3)$, $S=O$, $S(=O)_2$, $NR^3$, $-O-$, $-S-$ or $C(=O)NR^3$ and where one or more H atoms may be replaced by D, F, Cl, Br, I, CN or $NO_2$, and where, furthermore, $R^1$ may be linked to a group $R^2$ bonded in the 1,3-position adjacent to $R^1$ and may form a mono- or polycyclic, aliphatic or aromatic ring system;

$R^2$ is on each occurrence, identically or differently, H, D, F, Cl, Br, I, CHO, $N(R^3)_2$, $C(=O)R^3$, $P(=O)(R^3)_2$, $S(=O)R^3$, $S(=O)_2R^3$, $CR^3=C(R^3)_2$, CN, $NO_2$, $Si(R^3)_3$, $B(OR^3)_2$, $OS(=O)_2R^3$, $SO_3H$, $C(=O)OR^3$, $OR^3$, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which may be substituted by one or more radicals $R^3$, where one or more non-adjacent $CH_2$ groups may be replaced by $-R^3C=CR^3-$, $-C\equiv C-$, $Si(R^3)_2$, $Ge(R^3)_2$, $Sn(R^3)_2$, C=O, C=S, C=Se, $C=NR^3$, $P(=O)(R^3)$, $S(=O)_2$, $NR^3$, $-O-$, $-S-$ or $C(=O)NR^3$ and where one or more H atoms may be replaced by D, F, Cl, Br, I, CN or $NO_2$, or an aromatic or heteroaromatic ring system having 5 to 60 aromatic ring atoms, which may in each case be substituted by one or more radicals $R^3$, and which may be condensed with the ring to which it is bonded, or an aryloxy or heteroaryloxy group having 5 to 60 aromatic ring atoms, which may be substituted by one or more radicals $R^3$, or a combination of these systems, where two or more radicals $R^2$ may be linked to one another and may form a mono- or polycyclic, aliphatic or aromatic ring system, $R^3$ is on each occurrence, identically or differently, H, D, F, Cl, Br, I, CHO, $N(R^4)_2$, $C(=O)R^4$, $P(=O)(R^4)_2$, $S(=O)R^4$, $S(=O)_2R^4$, $CR^4=C(R^4)_2$, CN, $NO_2$, $Si(R^4)_3$, $B(OR^4)_2$, $OS(=O)_2R^4$, $SO_3H$, $C(=O)OR^4$, $OR^4$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each of which may be substituted by one or more radicals $R^4$, where one or more non-adjacent $CH_2$ groups may be replaced by $-R^4C=CR^4-$, $-C\equiv C-$, $Si(R^4)_2$, $Ge(R^4)_2$, $Sn(R^4)_2$, C=O, C=S, C=Se, $C=NR^4$, $P(=O)(R^4)$, $S=O$, $S(=O)_2$, $NR^4$, $-O-$, $-S-$ or $C(=O)NR^4$ and where one or more H atoms may be replaced by D, F, Cl, Br, I, CN or $NO_2$, or an aromatic or heteroaromatic ring system having 5 to 30 aromatic ring atoms, which may in each case be substituted by one or more radicals $R^4$, or an aryloxy or heteroaryloxy group having 5 to 30 aromatic ring atoms, which may be substituted by one or more radicals $R^4$, or a combination of these systems, where two or more radicals $R^3$ may be linked to one another and may form a mono- or polycyclic, aliphatic or aromatic ring system, $R^4$ is on each occurrence, identically or differently, H, D, F or an aliphatic, aromatic and/or heteroaromatic organic radical having 1 to 20 C atoms, in which, in addition, one or more H atoms may be replaced by D or F; two or more identical or different substituents $R^4$ here may also be linked to one another and form a mono- or polycyclic, aliphatic or aromatic ring system;

where at least two radicals $R^2$ in the compound of the formula (I) must be selected from the group comprising aromatic or heteroaromatic ring systems having 5 to 60 aromatic ring atoms, which may in each case be substituted by one or more radicals R³ and which may be condensed with the ring to which they are bonded, and fully conjugated alkenyl or alkynyl groups having 2 to 40 C atoms, which may be substituted by one or more radicals R³;

and where the following compound is excluded from the claim:

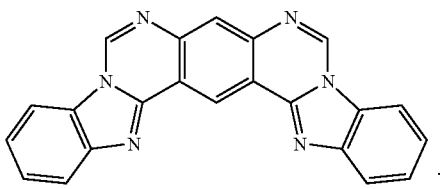 [SMILES: c1ccc2c(c1)nc1c3cc4c(cc3ncn21)ncn1c2ccccc2nc41]

An aryl group in the sense of this invention contains 6 to 60 C atoms; a heteroaryl group in the sense of this invention contains 1 to 60 C atoms and at least one heteroatom, with the proviso that the sum of C atoms and heteroatoms is at least 5. The heteroatoms are preferably selected from N, O and/or S. An aryl group or heteroaryl group here is taken to mean either a simple aromatic ring, i.e. benzene, or a simple heteroaromatic ring, for example pyridine, pyrimidine, thiophene, etc., or a condensed (fused) aryl or heteroaryl group, for example naphthalene, anthracene, phenanthrene, quinoline, isoquinoline, carbazole, etc.

An aryl group in the sense of this invention preferably contains 6 to 30 C atoms, very particularly preferably 6 to 20 C atoms.

A heteroaryl group in the sense of this invention preferably contains 2 to 30 C atoms, very particularly preferably 3 to 20 C atoms, and at least one heteroatom, with the proviso that the sum of C atoms and heteroatoms is at least 5.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an sp³-hybridised C, N or O atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl group or by a silyl group.

An aromatic or heteroaromatic ring system preferably contains 5 to 30 aromatic ring atoms, very particularly preferably 5 to 24 aromatic ring atoms.

An aromatic or heteroaromatic ring system having 5-60 aromatic ring atoms, which may be monocyclic or polycyclic, which may in each case be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic or heteroaromatic ring system R² which is condensed with the ring to which it is bonded is, for the purposes of the present invention, taken to mean a ring system which has at least one common aromatic bond with the ring in question. The following scheme is intended to illustrate this:

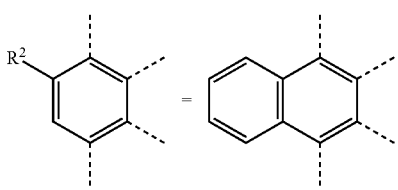

R² = condensed-on Ph

In the scheme shown, the aromatic or heteroaromatic ring system R² represents a condensed-on phenyl group. This shares a common aromatic bond (bold) with the ring to which it is bonded.

The embodiment where a radical R¹ is linked to a group R² bonded in the 1,3-position to the radical R¹ and at the same time forms a mono- or polycyclic, aliphatic or aromatic ring system is taken to mean, for example, that a structure depicted in the following scheme is present, in which the radicals R¹ and R² printed in bold are connected to one another with ring closure.

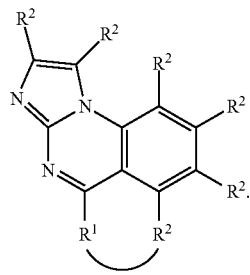

In the embodiment shown above, a compound of the formula (I) having a ring A is present (cf. formula (I-1) below). Equally, however, an embodiment of this type may also be present for a compound of the formula (I) which has a ring B (cf. formula (I-2) below).

Embodiments which are preferred in accordance with the invention of the said aromatic or heteroaromatic ring systems which are condensed with the ring to which they are bonded are phenyl groups, as shown above, and aryl groups, such as naphthyl, anthracenyl, phenanthrenyl or pyrenyl groups, and nitrogen-containing heterocycles, such as pyridine, pyrrole or imidazole.

For the purposes of the present application, a group R² which is condensed to the ring to which it is bonded is to be taken to mean a single group R². If just one group R² which represents a condensed-on aromatic or heteroaromatic system is present, a further group R² which is selected from aromatic or heteroaromatic ring systems, as defined above, and fully conjugated alkenyl or alkynyl groups, as defined above, must thus additionally be present in accordance with the definition of the compounds of the formula (I).

Fully conjugated alkenyl or alkynyl groups in the sense of the present invention are taken to mean groups which have a branched, unbranched or cyclised carbon chain in which C—C single bonds and C—C double bonds or triple bonds alternate in a regular manner, so that two C—C single bonds in no case follow one another directly in the chain. The fully conjugated alkenyl or alkynyl groups may contain both C—C double bonds and C—C triple bonds in the chain. The fully conjugated alkenyl or alkynyl groups may be substituted by one or more radicals R³, preferably by D, F, aryl groups, such as, for example, phenyl, naphthyl or anthracenyl, or heteroaryl groups, such as, for example, pyridyl, pyrimidyl, pyrazinyl, pyridazinyl, triazinyl or benzimidazolyl. The fully conjugated alkenyl or alkynyl groups preferably have 4 to 20 C atoms, very particularly preferably 4 to 10 C atoms.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or CH₂ groups may be substituted by the groups mentioned above under the definition of the radicals R¹ and R², is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The compounds of the formula (I) correspond to compounds of the following formulae (I-1), (I-2) and (I-3):

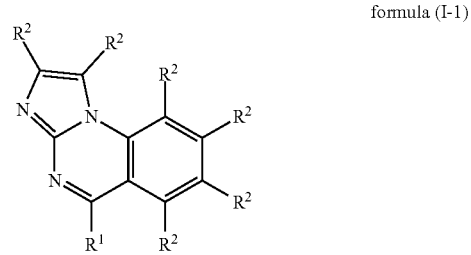

formula (I-1)

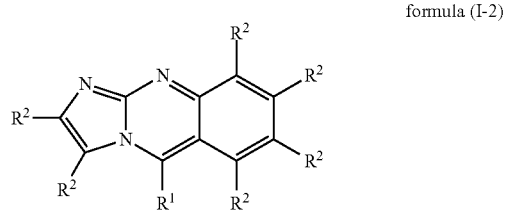

formula (I-2)

-continued formula (I-3)

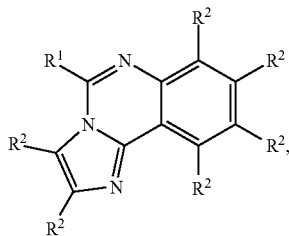

where the symbols occurring are defined as indicated above.

In a preferred embodiment of the invention, at least one radical $R^2$ is selected from aromatic or heteroaromatic ring systems having 5 to 60 aromatic ring atoms which are condensed with the ring to which they are bonded and which may in each case be substituted by one or more radicals $R^3$.

In a particularly preferred embodiment of the invention, at least two radicals $R^2$ are selected from aromatic or heteroaromatic ring systems having 5 to 30 aromatic ring atoms which are condensed with the ring to which they are bonded and which may in each case be substituted by one or more radicals $R^3$.

It is furthermore preferred in accordance with the invention for one of the two radicals $R^2$ which is bonded to the ring A, B or C in formula (I) to represent an aromatic or heteroaromatic ring system which is condensed with this ring. Particularly preferably, one of the two radicals $R^2$ which is bonded to the ring A, B or C in formula (I) represents a phenyl ring which is condensed with this ring.

In a preferred embodiment of the invention, the compound of the formula (I) contains at least one condensed aryl or heteroaryl group having more than 5 aromatic or heteroaromatic rings which are condensed with one another. In a particularly preferred embodiment of the invention, the compound of the formula (I) contains at least one condensed aryl or heteroaryl group having more than 6 aromatic or heteroaromatic rings which are condensed with one another.

Preferred embodiments of the compounds according to the invention are represented by the formulae (I-1a) to (I-3d):

formula (I-1a)

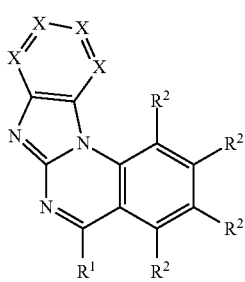

formula (I-1b)

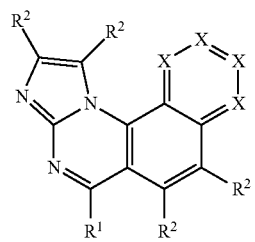

formula (I-1c)

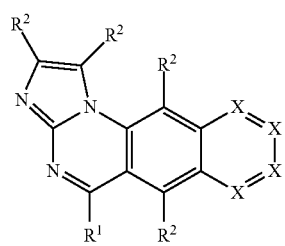

formula (I-1d)

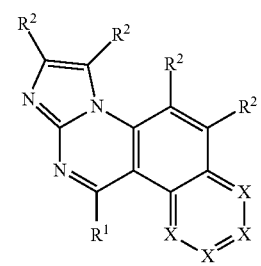

formula (I-2a)

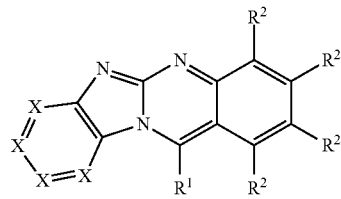

formula (I-2b)

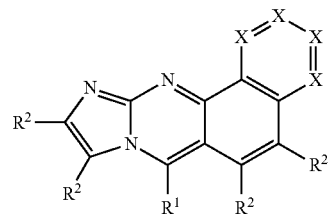

formula (I-2c)

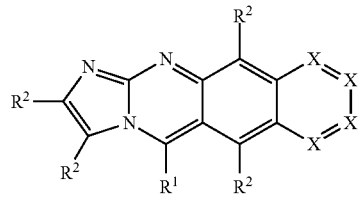

formula (I-2d)

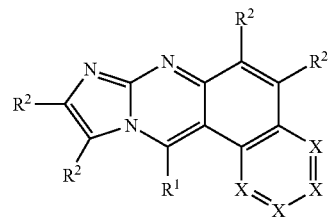

formula (I-3a)

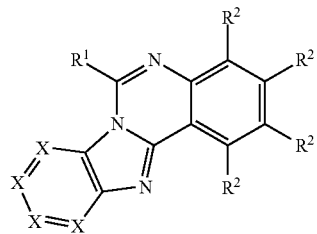

formula (I-3b)

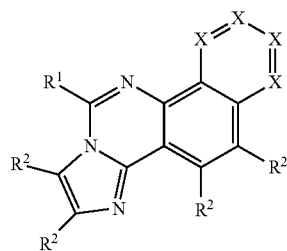

formula (I-3c)

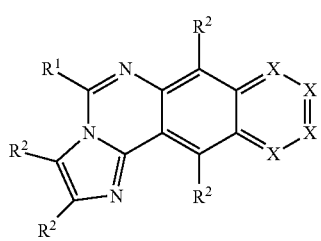

formula (I-3d)

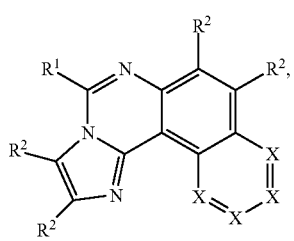

where R¹ and R² are defined as indicated above and furthermore:

X is on each occurrence, identically or differently, $CR^3$ or N, with the proviso that not more than two adjacent X are simultaneously equal to N; and where at least one radical $R^2$ must be selected from the group comprising aromatic or heteroaromatic ring systems having 5 to 60 aromatic ring atoms, which may in each case be substituted by one or more radicals $R^3$ and which may be condensed with the ring to which they are bonded, and fully conjugated alkenyl or alkynyl groups having 2 to 40 C atoms, which may be substituted by one or more radicals $R^3$.

Further preferred embodiments of the compounds according to the invention are represented by the formulae (I-1e) to (I-1k), (I-2e) to (I-2k) and (I-3e) to (I-3k):

formula (I-1e)

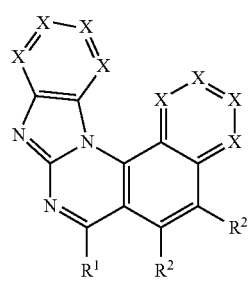

formula (I-1f)

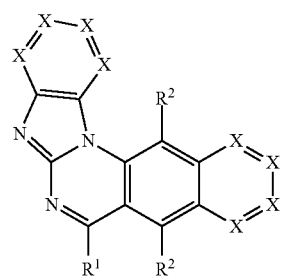

formula (I-1g)

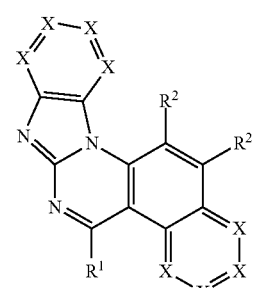

formula (I-1h)

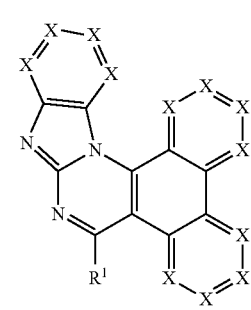

formula (I-1i)

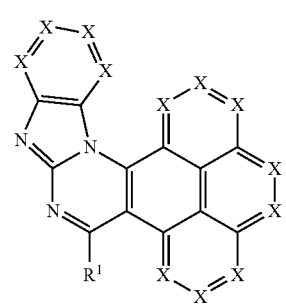

formula (I-1j)

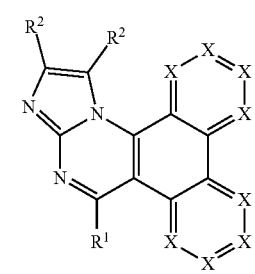

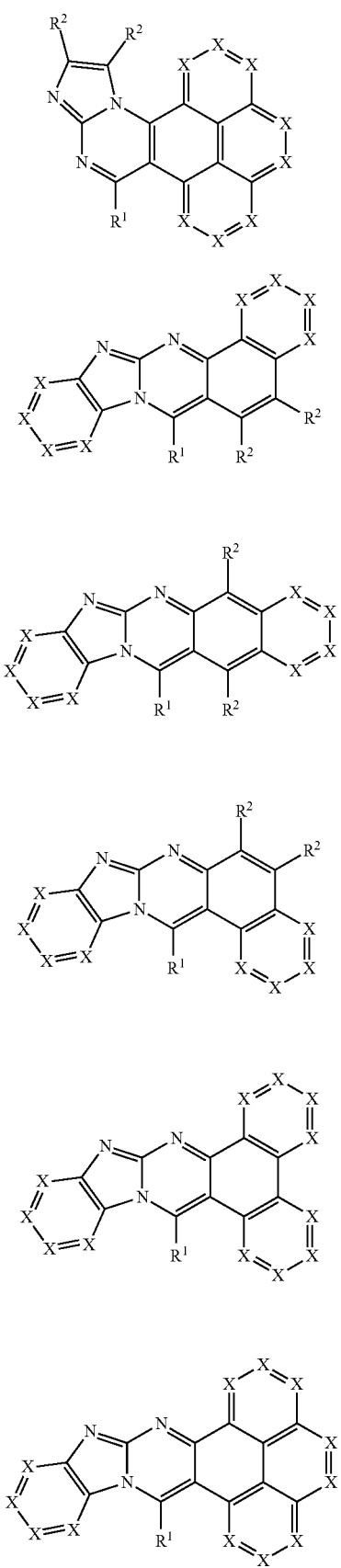
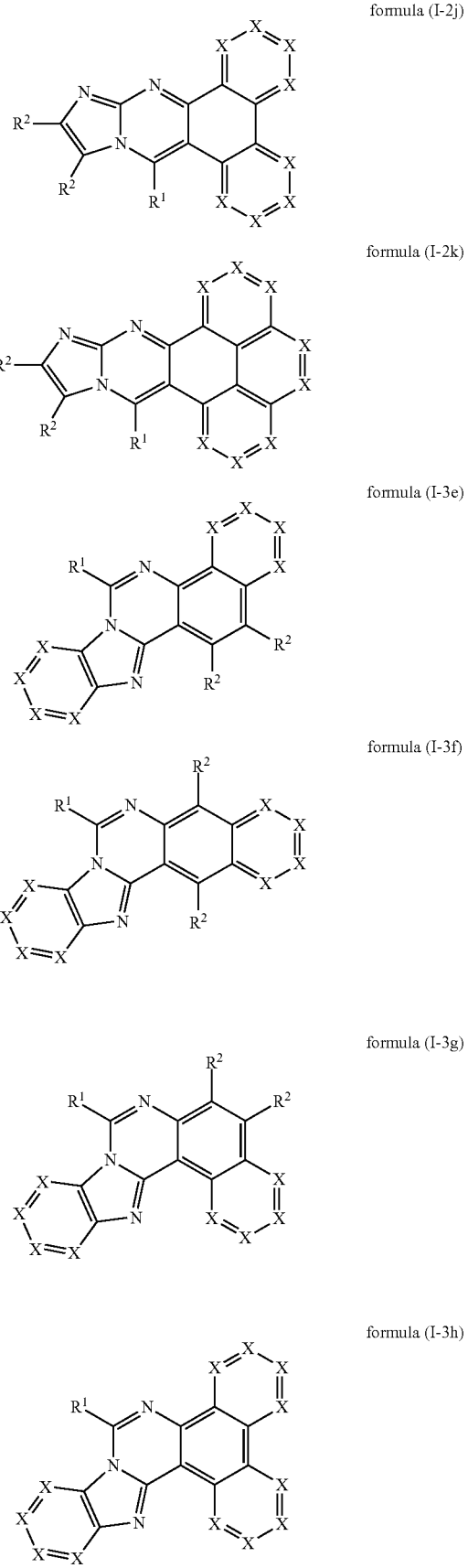

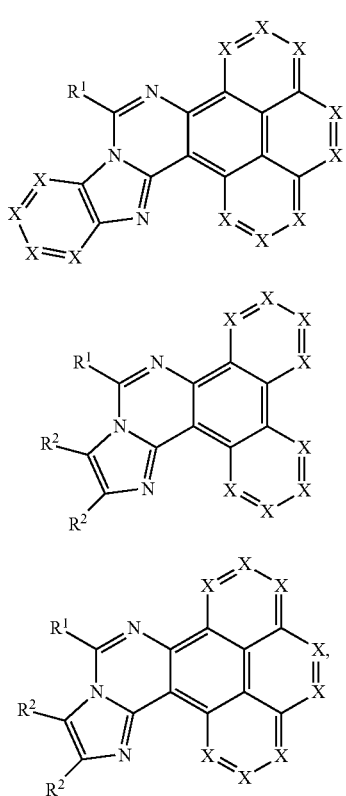

formula (I-3i)

formula (I-3j)

formula (I-3k)

where $R^1$, $R^2$ and X are as defined above.

For the compounds of the formulae (I-1a) to (I-1k), (I-2a) to (I-2k) and (I-3a) to (I-3k) shown above, it is preferred for X to be equal to $CR^3$.

It is furthermore preferred, in particular for compounds of the formulae (I-1a) to (I-1k), (I-2a) to (I-2k) and (I-3a) to (I-3k), for the following to apply to the radical $R^1$:

$R^1$ is H, D, F, $N(R^3)_2$, $C(=O)R^3$, $CR^3=C(R^3)_2$, CN, $Si(R^3)_3$, $OR^3$, a straight-chain alkyl or alkoxy group having 1 to 10 C atoms, a branched or cyclic alkyl or alkoxy group having 3 to 10 C atoms or an alkenyl or alkynyl group having 2 to 10 C atoms, where the said groups may be substituted by one or more radicals $R^3$ and where one or more adjacent or non-adjacent $CH_2$ groups may be replaced by —C≡C—, $R^3C=CR^3$, $Si(R^3)_2$, C=O, $C=NR^3$, $NR^3$, —O—, —S— or $C(=O)NR^3$.

It is very particularly preferred, especially for compounds of the formulae (I-1a) to (I-1k), (I-2a) to (I-2k) and (I-3a) to (I-3k), for $R^1$ to be selected from H, D, $N(R^3)_2$, $C(=O)R^3$, $CR^3=C(R^3)_2$, $OR^3$, a straight-chain alkyl group having 1 to 8 C atoms or a branched or cyclic alkyl group having 3 to 8 C atoms, where the said groups may each be substituted by one or more radicals $R^3$ and where one or more adjacent or non-adjacent $CH_2$ groups may be replaced by —C≡C—, $R^3C=CR^3$, C=O, $NR^3$, —O— or —S—.

It is furthermore preferred, especially for compounds of the formulae (I-1a) to (I-1 k), (I-2a) to (I-2k) and (I-3a) to (I-3k), for the following to apply to the radical $R^2$:

$R^2$ is, identically or differently on each occurrence, H, D, F, $N(R^3)_2$, $C(=O)R^3$, $CR^3=C(R^3)_2$, CN, $Si(R^3)_3$, $OR^3$, a straight-chain alkyl or alkoxy group having 1 to 10 C atoms, a branched or cyclic alkyl or alkoxy group having 3 to 10 C atoms or an alkenyl or alkynyl group having 2 to 10 C atoms, where the said groups may each be substituted by one or more radicals $R^3$ and where one or more adjacent or non-adjacent $CH_2$ groups in the above-mentioned groups may be replaced by —C≡C—, $R^3C=CR^3$, $Si(R^3)_2$, C=O, $C=NR^3$, $NR^3$, —O—, —S— or $C(=O)NR^3$, or an aryl or heteroaryl group having 5 to 30 aromatic ring atoms, which may be condensed with the ring to which it is bonded, and which may be substituted by one or more groups $R^3$.

It is very particularly preferred, especially for compounds of the formulae (I-1a) to (I-1k), (I-2a) to (I-2k) and (I-3a) to (I-3k), for $R^2$ to be selected from H, D, $N(R^3)_2$, $C(=O)R^3$, $CR^3=C(R^3)_2$, $OR^3$, a straight-chain alkyl group having 1 to 8 C atoms or a branched or cyclic alkyl group having 3 to 8 C atoms, where the said groups may each be substituted by one or more radicals $R^3$ and where one or more adjacent or non-adjacent $CH_2$ groups may be replaced by —C≡C—, $R^3C=CR^3$, C=O, $NR^3$, —O— or —S—, or an aryl or heteroaryl group having 5 to 20 aromatic ring atoms, which may be condensed with the ring to which it is bonded, and which may be substituted by one or more groups $R^3$.

It is furthermore preferred, especially for compounds of the formulae (I-1a) to (I-1k), (I-2a) to (I-2k) and (I-3a) to (I-3k), for the following to apply to the radical $R^3$:

$R^3$ is, identically or differently on each occurrence, H, D, F, $N(R^4)_2$, $C(=O)R^4$, $CR^4=C(R^4)_2$, CN, $Si(R^4)_3$, $OR^4$, a straight-chain alkyl or alkoxy group having 1 to 10 C atoms, a branched or cyclic alkyl or alkoxy group having 3 to 10 C atoms or an alkenyl or alkynyl group having 2 to 10 C atoms, where the said groups may each be substituted by one or more radicals $R^4$ and where one or more adjacent or non-adjacent $CH_2$ groups in the above-mentioned groups may be replaced by —C≡C—, $R^4C=CR^4$, $Si(R^4)_2$, C=O, $C=NR^4$, $NR^4$, —O—, —S— or $C(=O)NR^4$, or an aryl or heteroaryl group having 5 to 30 aromatic ring atoms, which may be substituted by one or more groups $R^4$.

It is very particularly preferred, especially for compounds of the formulae (I-1a) to (I-1k), (I-2a) to (I-2k) and (I-3a) to (I-3k), for $R^3$ to be selected from H, D, $N(R^4)_2$, $C(=O)R^4$, $CR^4=C(R^4)_2 OR^4$, a straight-chain alkyl group having 1 to 8 C atoms or a branched or cyclic alkyl group having 3 to 8 C atoms, where the said groups may each be substituted by one or more radicals $R^4$ and where one or more adjacent or non-adjacent $CH_2$ groups may be replaced by —C≡C—, $R^4C=CR^4$, C=O, $NR^4$, —O— or —S—, or an aryl or heteroaryl group having 5 to 20 aromatic ring atoms, which may be condensed with the ring to which it is bonded, and which may be substituted by one or more groups $R^4$.

The above-mentioned preferred embodiments according to the invention can be combined with one another as desired for the purposes of the present invention.

In a preferred embodiment of the invention, the preferred embodiments of the groups $R^1$, $R^2$ and $R^3$ occur combined with the preferred embodiments of the formulae (I-1a) to (I-1k), (I-2a) to (I-2k) and (I-3a) to (I-3k).

Examples of compounds of the formula (I) are the compounds shown below:

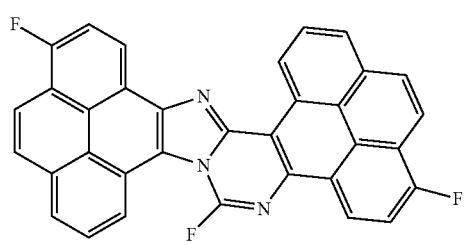

1

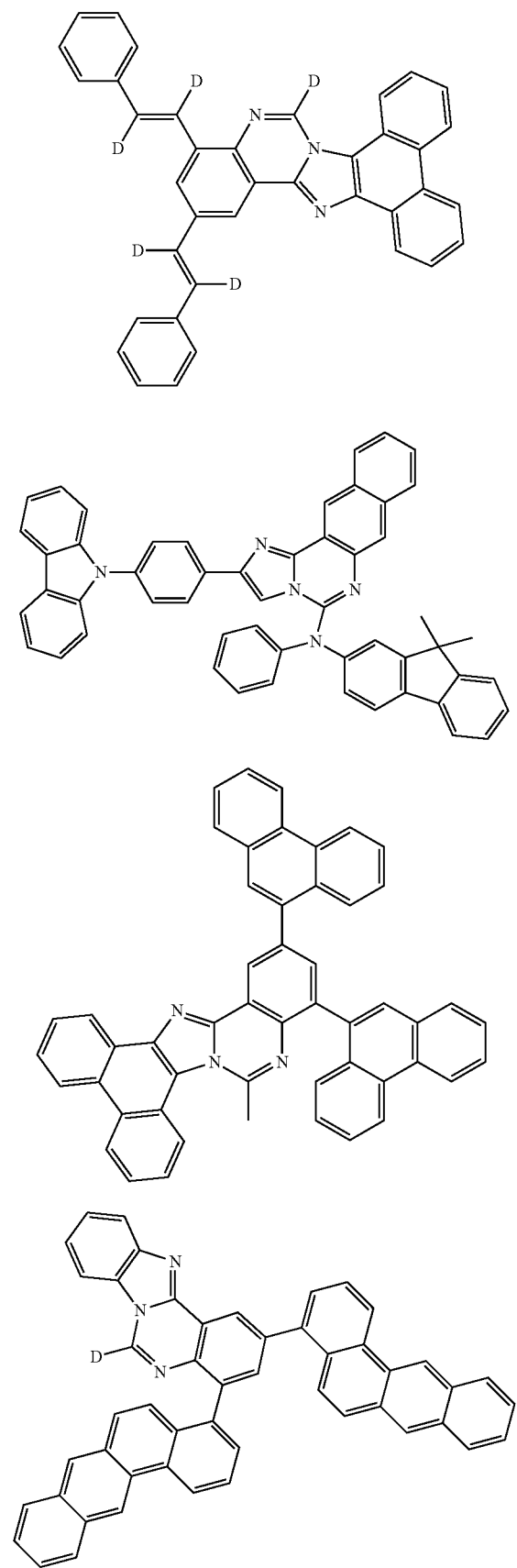
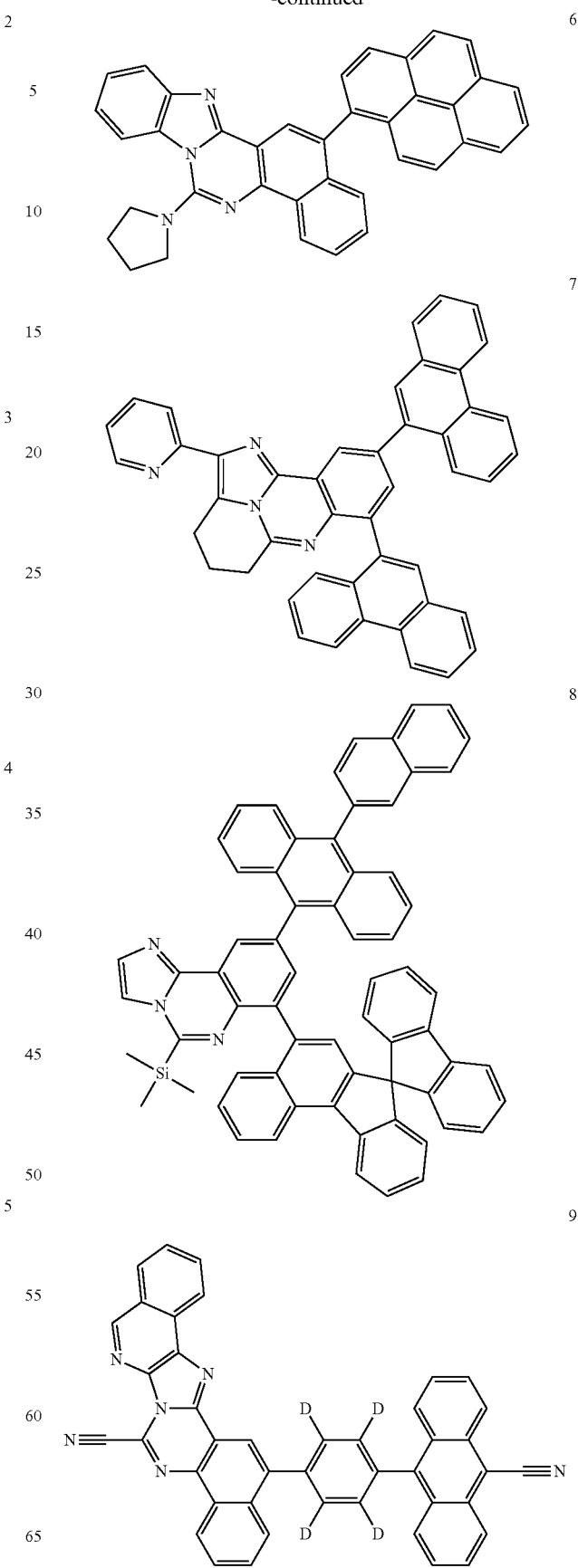

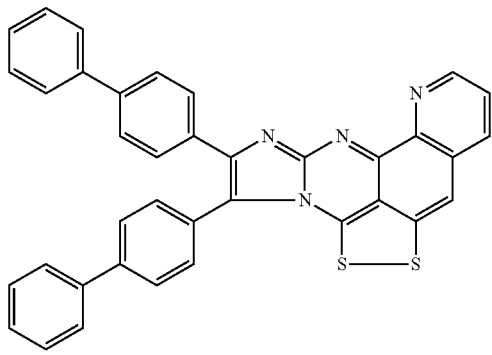
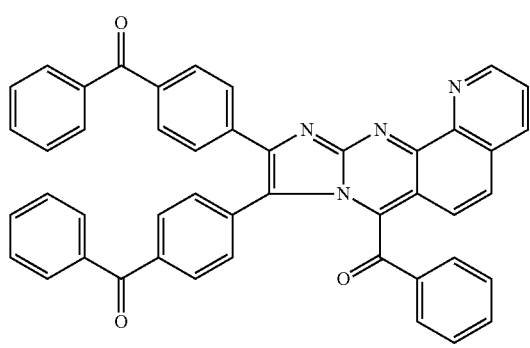
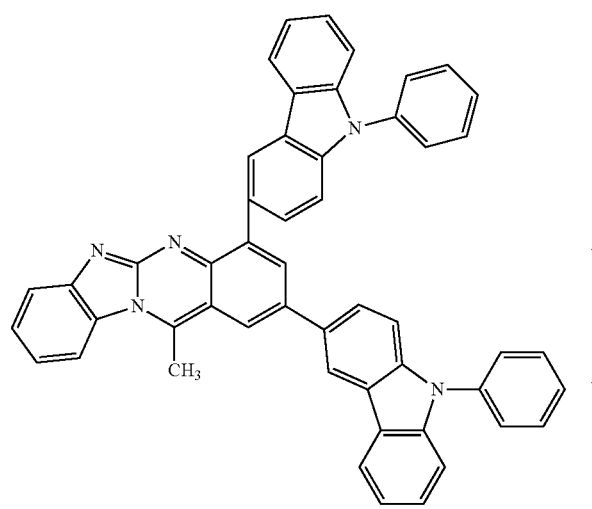
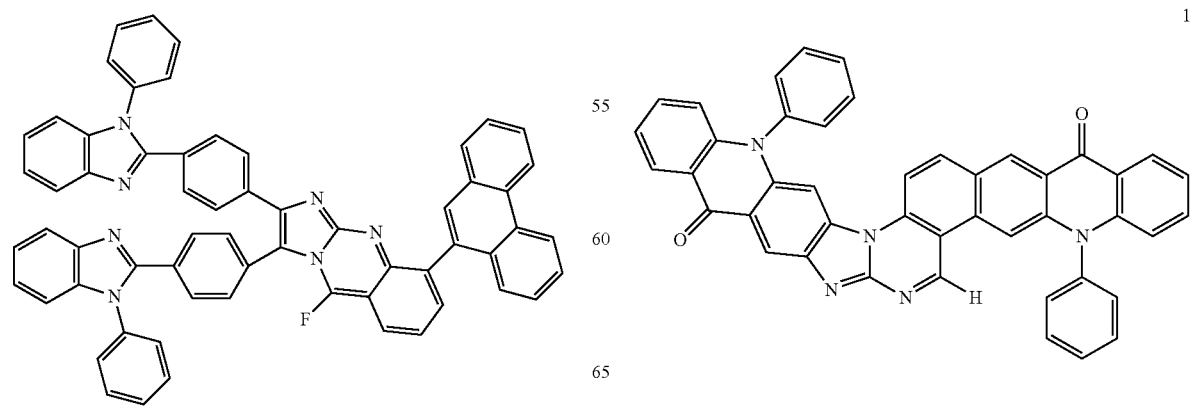
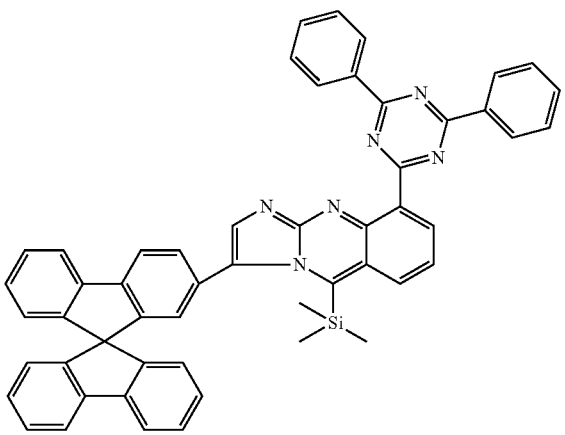
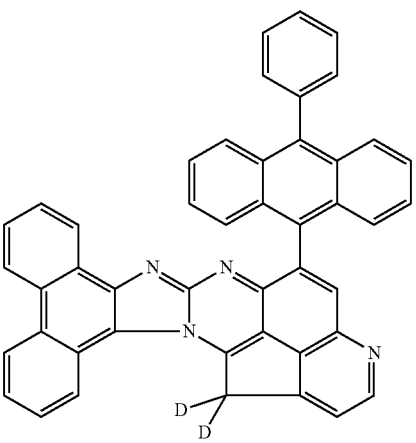
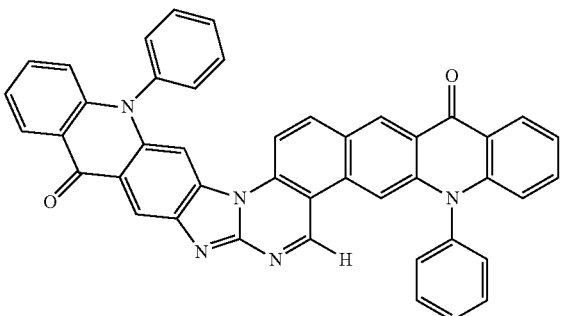

17

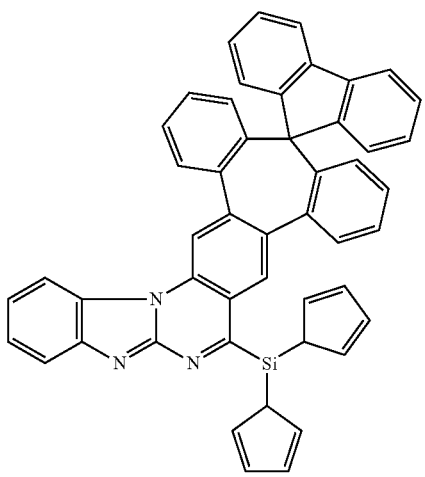

18

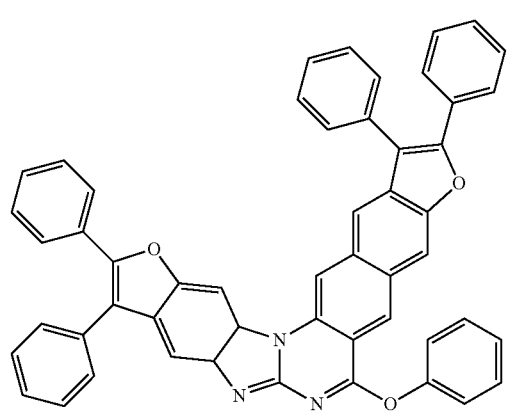

19

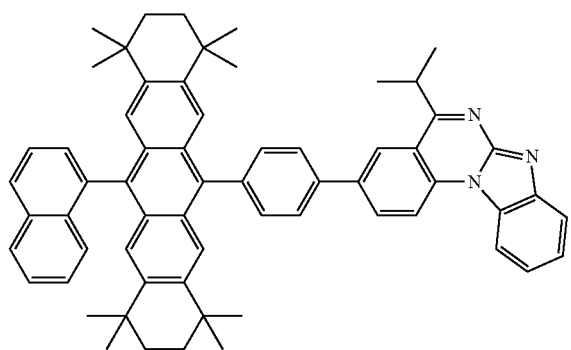

20

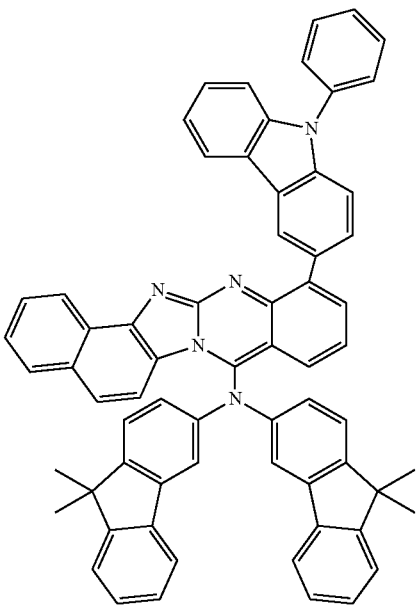

21

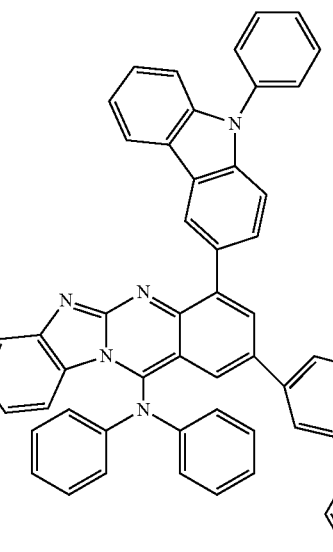

The basic structures of the compounds according to the invention can be prepared by synthetic processes known to the person skilled in the art. Examples of the synthesis of compounds of the formulae (I-1), (I-2) and (I-3) are given below.

The synthesis of the skeleton of the compounds according to the invention in the embodiment of the formula (I-1) can be carried out as shown in Scheme 1. The substituents R, R' and R" here are preferably defined as shown below. The definitions also apply to the following reaction schemes.

For the synthesis of the compounds of the formula (I-1), firstly, for example, a 1-amino-2-cyanophenyl compound is reacted with $CO_2$ and DBU. A quinazolinone compound which is selectively chlorinated in the 2-position is obtained by chlorination and hydrolysis of one of the two chlorine substituents introduced. This is followed by coupling to an aliphatic amino compound which additionally carries an acetal group. The acetal group subsequently reacts with the unsubstituted amino group of the quinazoline, giving an imidazoquinazoline basic structure of the formula (I-1). This can subsequently be functionalised further by means of a substituent R".

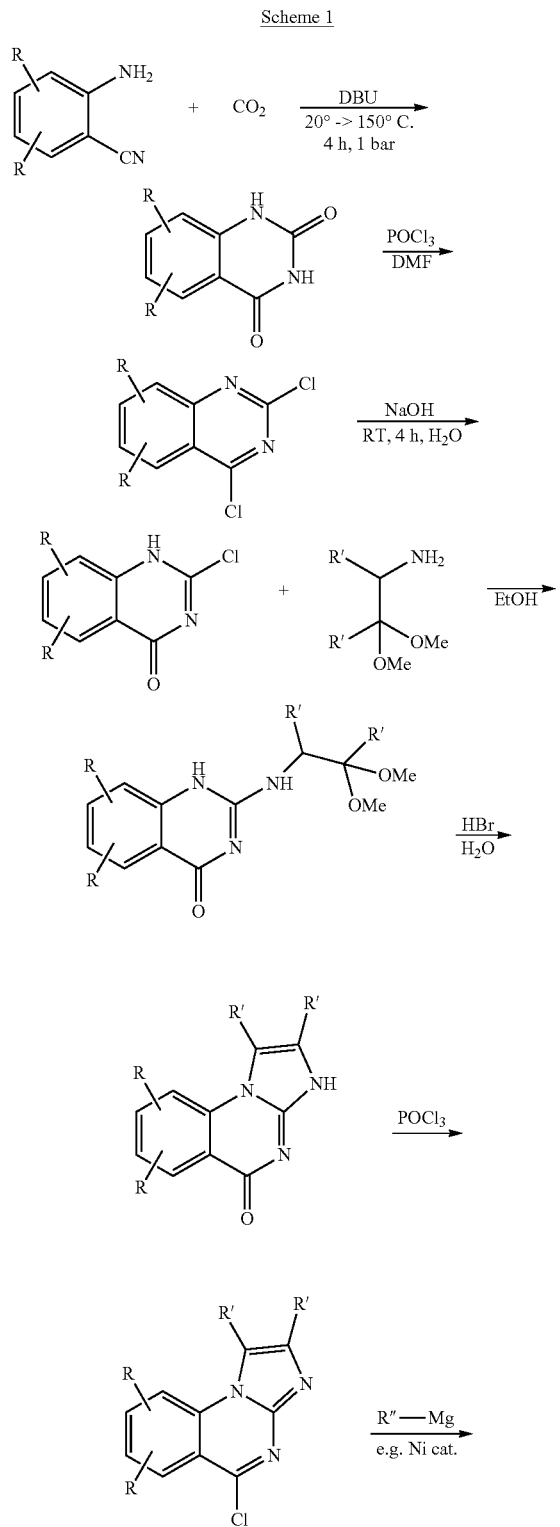

-continued

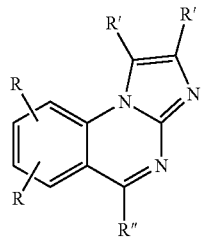

R = H, I, Br, NO$_2$
R' = H, alkyl or part of a (hetero)aromatic group
R" = alkyl, thioether, alkoxy, CN, F, deuterium For the synthesis of benzo-fused compounds of the formula (I-1), the process as shown in Scheme 2, for example, can be followed. To this end, firstly a 2-aminobenzimidazole derivative is synthesised and subsequently reacted with ortho-bromobenzoic acid. The resultant benzimidazoquinazoline basic structure of the formula (I-1) can be functionalised as already shown in Scheme 1 via organometallic coupling to a substituent R".

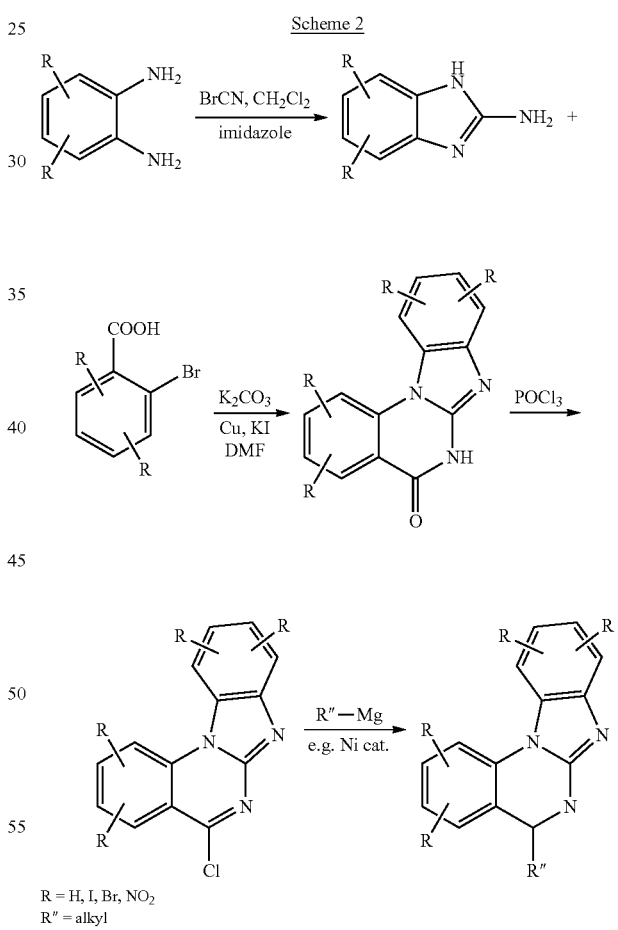

R = H, I, Br, NO$_2$
R" = alkyl

Scheme 3 shows the synthesis of an imidazoquinazoline derivative of the formula (I-2). Firstly, a 2-chlorine-substituted imidazole derivative is prepared, which is reacted with an ortho-aminobenzoyl chloride. In this reaction, the imidazoquinazoline basic structure is built up. The substituent R" can subsequently be introduced via the sequence comprising chlorination and organometallic coupling.

Scheme 3

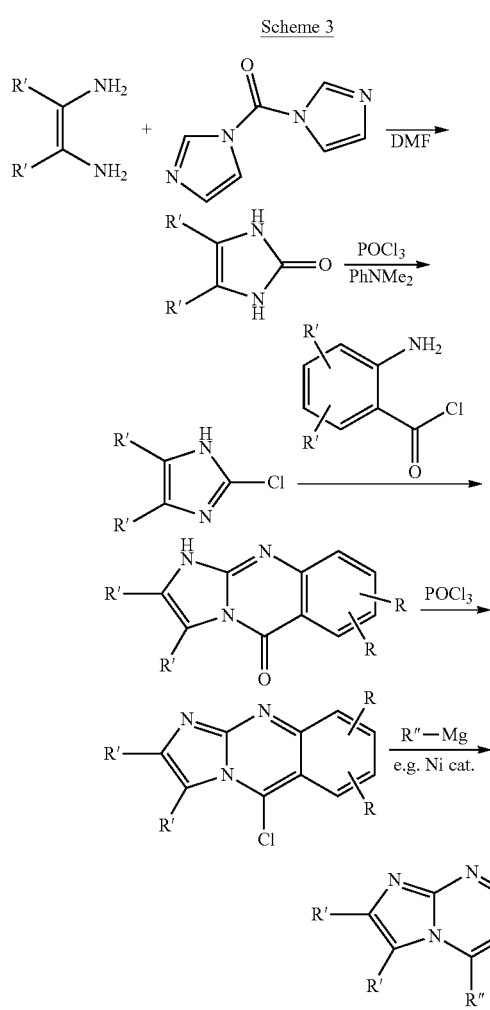

R = H, I, Br, NO$_2$
R' = H, alkyl or part of a (hetero)aromatic group
R" = alkyl Scheme 4 shows the synthesis of a benzimidazoquinazoline derivative of the formula (I-2). It starts from an ortho-diaminophenyl derivative, which is reacted firstly with diisopropylcarbodiimide and a second phenyl derivative containing an isothiocyanate group and an o-carboxylate group. Ba(OH)$_2$ is subsequently added, and the reaction mixture is irradiated with microwaves, during which the benzimidazoquinazoline basic structure of the formula (I-2) forms. A substituent R" can subsequently be introduced via a sequence comprising chlorination and organometallic coupling.

Scheme 4

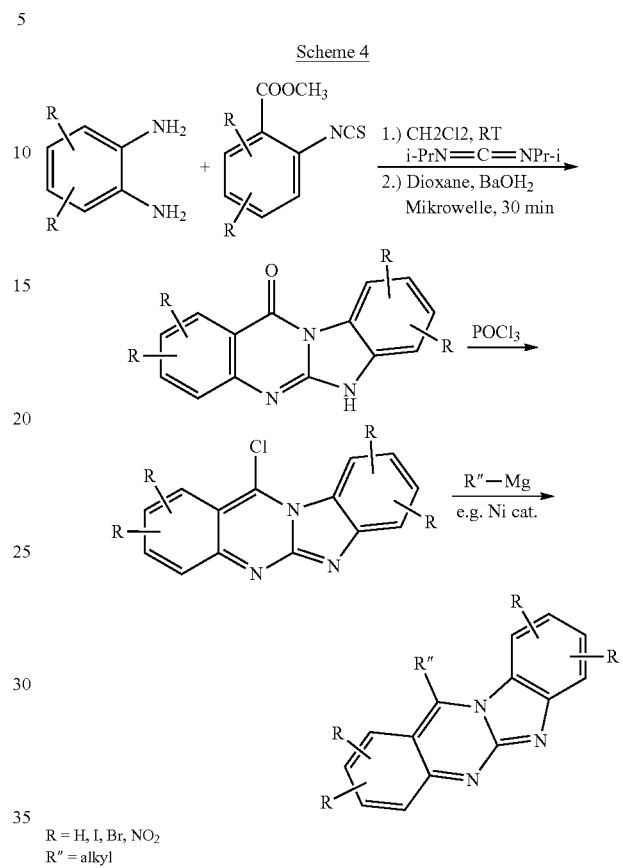

R = H, I, Br, NO$_2$
R" = alkyl

Scheme 5 shows by way of example possible synthetic routes for the preparation of compounds of the formula (I-3) according to the invention. The common intermediate is a 2-phenylimidazolyl derivative, which can be obtained via two alternative reaction routes from ortho-aminobenzoic acid and a 1,2-diaminoethene derivative. Compounds containing thioether radicals as R" can be obtained therefrom by microwave-supported reaction with CS$_2$ and subsequent alkylation, compounds containing alkyl radicals as R" can be obtained by reaction with carboxylic anhydrides, and compounds in which R" represents a cyano group can be obtained by reaction with the Appel reagent shown.

Scheme 5

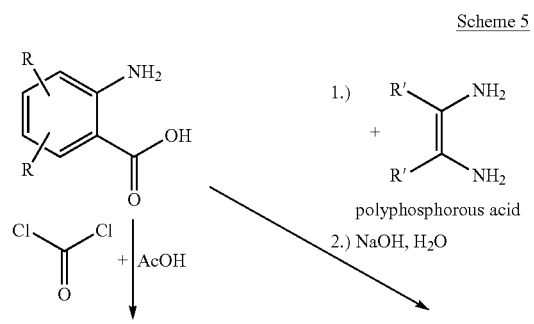

-continued

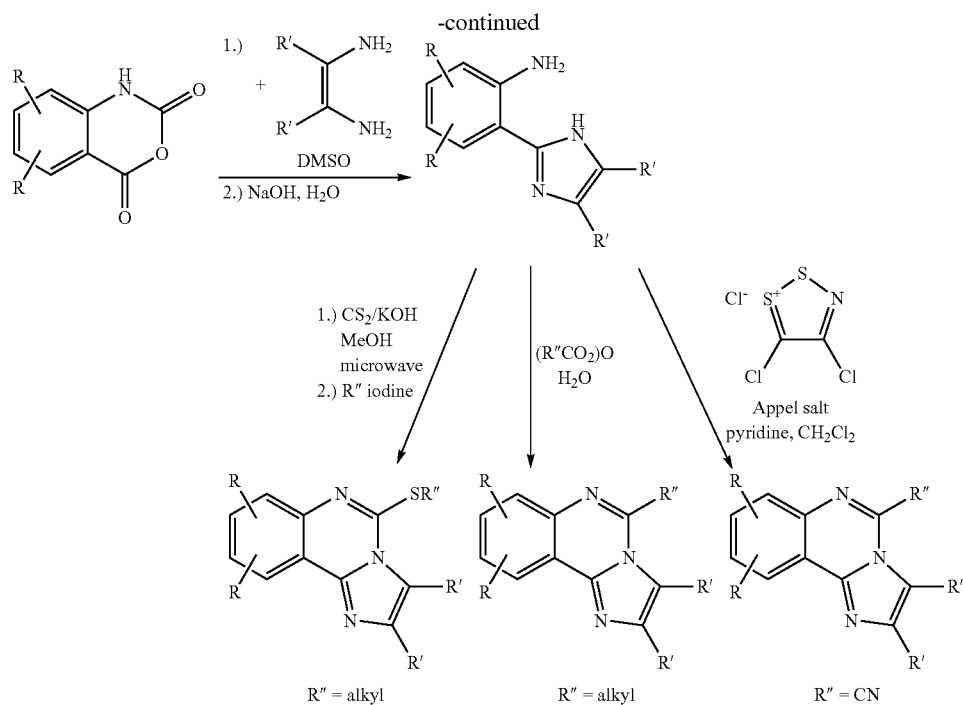

R = H, I, Br, NO₂
R' = H, alkyl or part of a (hetero)aromatic group
R" = alkyl, CN A common feature of the processes for the preparation of the skeletons of the compounds of the formula (I) according to the invention is the use of one or more condensation reactions between one or more amino groups and one or more carbonyl or carboxyl functions with formation of a heterocyclic ring.

The reactions shown are followed by further reaction steps for the introduction of, for example, (hetero)aryl substituents by organometallic coupling reactions, such as, for example, Suzuki, Sonogashira, Stille, Heck reaction, without making a restrictive choice.

Further functionalisation steps can then follow in order to introduce any additional substituents. Examples thereof are halogenation, preferably bromination, and subsequent coupling reactions, such as Hartwig-Buchwald coupling, Stille coupling and/or Sonogashira coupling, The synthetic processes shown represent preferred embodiments of processes for the preparation of the skeletons of the compounds according to the invention. The person skilled in the art will be able to develop alternative synthetic routes within the bounds of his expert knowledge in the area of organic synthesis and employ them for the synthesis of the compounds according to the invention.

The invention thus relates to a process for the preparation of compounds of the formula (I) in which one or more condensation reactions between one or more amino groups and one or more carbonyl or carboxyl functions with formation of a heterocyclic ring are included.

The invention furthermore relates to formulations comprising at least one compound of the formula (I) and at least one solvent, preferably an organic solvent. All organic solvents as are usually used in processes for the production of organic electroluminescent devices can be used here.

The invention furthermore relates to mixtures comprising at least one compound of the formula (I) and at least one further organic or inorganic compound. Preference is given to mixtures comprising at least one compound of the formula (I) and at least one organic or inorganic alkali-metal compound.

Preference is furthermore given to mixtures comprising at least one matrix compound and at least one emitter compound, where at least one compound of the formula (I), which represents either a matrix compound or an emitter compound, must be present. Particular preference is given to mixtures comprising at least one compound of the formula (I) and at least one phosphorescent emitter compound.

The compounds of the formula (I) according to the invention are suitable for use in electronic devices, in particular in organic electroluminescent devices (OLEDs). The compounds mentioned as preferred above are also preferred for use in OLEDs. Depending on the substitution, the compounds are employed in different functions and layers, but preferably as electron-transport material, as hole-blocking material, as matrix material and/or as emitter material. Particular preference is given to the use as electron-transport material and/or as matrix material. The preferred use of the compounds depends, in particular, on the choice of substituents $R^1$ and $R^2$ in formula (I). It should furthermore be noted that certain embodiments of the compounds according to the invention may be suitable both as electron-transport material and also as hole-blocking material, matrix material and emitter material.

The invention thus furthermore relates to the use of the compounds of the formula (I) according to the invention in electronic devices, preferably in organic electroluminescent devices.

In a preferred embodiment of the present invention, the compounds of the formula (I) are employed as electron-transport material, preferably in an electron-transport layer.

In this case, it may be preferred for the compounds of the formula (I) to be employed in combination with a further electron-transport material. Particularly suitable electron-transport materials which can be employed in combination with the compounds according to the invention are, for example, the electron-transport materials shown in one of the following tables or the materials disclosed in Y. Shirota et al., Chem. Rev. 2007, 107(4), 953-1010.

If the compound of the formula (I) and one of the above-mentioned electron-transport materials are present in a mixture, the ratio of the compound of the formula (I) to the electron-transport material is preferably 20:80 to 80:20, particularly preferably 30:70 to 70:30 and very particularly preferably 30:70 to 50:50, in each case based on the volume.

If the compounds of the formula (I) are employed as electron-transport material in an organic electroluminescent device, they can, in accordance with the invention, be employed in combination with an organic or inorganic alkali-metal compound. "In combination with an organic alkali-metal compound" here means that the compounds of the formula (I) and the alkali-metal compound are either in the form of a mixture in one layer or separately in two successive layers. In a preferred embodiment of the invention, the compounds of the formula (I) and the organic alkali-metal compound are in the form of a mixture in one layer.

An organic alkali-metal compound in the sense of this invention is intended to be taken to mean a compound which contains at least one alkali metal, i.e. lithium, sodium, potassium, rubidium or caesium, and which furthermore contains at least one organic ligand. Suitable organic alkali-metal compounds are, for example, the compounds disclosed in WO 07/050301, WO 07/050334 and EP 1144543. These are incorporated into the present application by way of reference.

If the compound of the formula (I) and the organic or inorganic alkali-metal compound are in a mixture, the ratio of the compound of the formula (I) to the organic alkali-metal compound is preferably 10:90 to 90:10, particularly preferably 20:80 to 80:20, very particularly preferably 30:70 to 50:50, especially 30:70 to 45:55, in each case based on the volume. The organic alkali-metal compound is thus particularly preferably present in higher proportion than the compound of the formula (I).

In a further preferred embodiment of the invention, the compounds according to the invention are employed as hole-blocking material. The use as hole-blocking material preferably takes place in a hole-blocking layer, in particular in a hole-blocking layer of a phosphorescent OLED. A hole-blocking layer in the sense of this invention is a layer which is arranged between an emitting layer and an electron-transport layer.

In a further preferred embodiment of the invention, the compound of the formula (I) is employed as matrix material for a fluorescent emitter in an emitting layer. Particularly suitable for use as matrix materials are compounds of the formula (I) which have an extended aromatic or heteroaromatic system, for example through condensation of a plurality of aryl or heteroaryl groups onto the skeleton of the compound. Also particularly suitable for use as matrix materials are compounds of the formula (I) which contain condensed aryl or heteroaryl groups as substituents.

A matrix material in a system comprising matrix and emitter is taken to mean the component which is present in the higher proportion in the system. In a system comprising a matrix material and a plurality of emitter materials, the matrix material is taken to mean the component whose proportion in the mixture is the highest.

The proportion of the matrix material of the formula (I) in the emitting layer is between 50.0 and 99.9% by vol., preferably between 80.0 and 99.5% by vol., particularly preferably between 90.0 and 99.0% by vol. Correspondingly, the proportion of the emitter material is between 0.1 and 50.0% by vol., preferably between 0.5 and 20.0% by vol. and particularly preferably between 1.0 and 10.0% by vol.

If the compounds according to the invention are employed as matrix materials for fluorescent emitters, the emitter compounds used can be the compounds usually employed by the person skilled in the art in electronic devices. Fluorescent emitter materials which are preferred in accordance with the invention are mentioned in one of the following sections.

It may furthermore be preferred for the compound of the formula (I) to be employed as matrix material in combination with a further matrix material in the emitting layer. Particularly suitable matrix materials which can be employed in combination with the compounds according to the invention are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461) or the benzanthracenes (for example in accordance with WO 08/145239). Particular preference is given to compounds selected from the classes of the oligoarylenes comprising naphthalene, anthracene, benzanthracene and/or pyrene or atropisomers of these compounds. An oligoarylene in the sense of this invention is intended to be taken to mean a compound in which at least three aryl or arylene groups are bonded to one another.

Suitable matrix materials for combination with the compounds according to the invention are, for example, the compounds shown as preferred matrix materials in one of the following table, and compounds as disclosed in WO 04/018587, WO 08/006449, U.S. Pat. No. 5,935,721, US 2005/0181232, JP 2000/273056, EP 681019, US 2004/0247937 and US 2005/0211958.

If the compound of the formula (I) and one of the above-mentioned matrix compound are in a mixture, the ratio of the compound of the formula (I) to the matrix compound is preferably 20:80 to 80:20, particularly preferably 30:70 to 70:30, very particularly preferably 30:70 to 50:50, especially 30:70 to 45:55, in each case based on the volume. One of the above-mentioned matrix compounds is thus particularly preferably present in higher proportion than the compound of the formula (I).

In a further embodiment of the invention, the compounds according to the invention are used as matrix materials for phosphorescent emitters.

In this case, it may likewise be preferred for the compounds of the formula (I) to be employed in combination with a further matrix material in the emitting layer. Particularly suitable matrix materials which can be employed in combination with the compounds according to the invention are aromatic ketones, aromatic phosphine oxides or aromatic sulfoxides or sulfones, for example in accordance with WO 04/013080, WO 04/093207, WO 06/005627 or the application WO 10/006680, triarylamines, carbazole derivatives, for example CBP (N,N-biscarbazolylbiphenyl) or the carbazole derivatives disclosed in WO 05/039246, US 2005/0069729, JP 2004/288381, EP 1205527 or WO 08/086851, indolocarbazole derivatives, for example in accordance with WO 07/063754 or WO 08/056746, azacarbazole derivatives, for example in accordance with EP 1617710, EP 1617711, EP 1731584, JP 2005/347160, bipolar matrix materials, for example in accordance with WO 07/137725, silanes, for example in accordance with WO 05/111172, azaboroles or boronic esters, for example in accordance with WO 06/117052, triazine derivatives, for example in accordance with WO 2010/015306, WO 07/063754 or WO 08/056746, zinc complexes, for example in accordance with EP 652273 or WO 09/062578, diazasilole or tetraazasilole derivatives, for example in accordance with the application WO 10/054729, diazaphosphole derivatives, for example in accordance with the application WO 10/054730, indenocarbazole derivatives, for example in accordance with WO 2010/136109, or bridged carbazole derivatives, for example in accordance with WO 2011/042107.

Suitable phosphorescent compounds (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. For this purpose, use is preferably made of compounds which contain copper, molybdenum, tungsten, rhenium, ruthenium, osmium, rhodium, iridium, palladium, platinum, silver, gold or europium, in particular compounds which contain iridium, platinum or copper.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as used in accordance with the prior art for phosphorescent OLEDs and as are known to the person skilled in the art in the area of organic electroluminescent devices are suitable. The person skilled in the art will also be able to use further phosphorescent complexes without an inventive step.

In a further embodiment of the invention, the compounds of the formula (I) are employed as emitting materials in an emitting layer. Particularly suitable for use as emitter materials are compounds of the formula (I) which have an extended aromatic or heteroaromatic system, for example through condensation of a plurality of aryl or heteroaryl groups onto the skeleton of the compound. Also particularly suitable for use as matrix materials are compounds of the formula (I) which contain condensed aryl or heteroaryl groups or arylamino groups as substituents. The compounds according to the invention are preferably used as green or blue emitters. If the compounds according to the invention are used as emitter materials, they are preferably employed in a mixture with one or more matrix materials in the emitting layer. Matrix materials which are preferred in accordance with the invention are mentioned in a following section.

The proportion of the compound of the formula (I) as emitter in the mixture of the emitting layer is in these cases between 0.1 and 50.0% by vol., preferably between 0.5 and 20.0% by vol., particularly preferably between 1.0 and 10.0% by vol. Correspondingly, the proportion of the matrix material is between 50.0 and 99.9% by vol., preferably between 80.0 and 99.5% by vol., particularly preferably between 90.0 and 99.0% by vol.

The invention furthermore relates to electronic devices comprising at least one compound of the formula (I). The electronic devices here are preferably selected from the devices mentioned above. Particular preference is given to organic electroluminescent devices comprising anode, cathode and at least one emitting layer, characterised in that at least one organic layer, which may be an emitting layer, an electron-transport layer or another layer, comprises at least one compound of the formula (I).

The electronic device is preferably selected from the group consisting of organic electroluminescent devices (OLEDs), organic integrated circuits (O-ICs), organic field-effect transistors (O-FETs), organic thin-film transistors (O-TFTs), organic light-emitting transistors (O-LETs), organic solar cells (O-SCs), organic optical detectors, organic photoreceptors, organic field-quench devices (O-FQDs), light-emitting electrochemical cells (LECs or OLECs), organic laser diodes (O-lasers) and "organic plasmon emitting devices" (D. M. Koller et al., Nature Photonics 2008, 1-4), but preferably organic electroluminescent devices (OLEDs).

The organic electroluminescent device according to the invention comprises cathode, anode and at least one emitting layer. Apart from these layers, it may also comprise further layers, for example one or more hole-injection layers, hole-transport layers, hole-blocking layers, electron-transport layers, electron-injection layers, exciton-blocking layers and/or charge-generation layers. It is likewise possible for interlayers, which have, for example, an exciton-blocking function, to be introduced between two emitting layers. However, it should be pointed out that each of these layers does not necessarily have to be present. The organic electroluminescent device here may comprise one emitting layer or it may comprise a plurality of emitting layers. If a plurality of emission layers are present, these preferably have overall a plurality of emission maxima between 380 nm and 750 nm, resulting overall in white emission, i.e. various emitting compounds which are able to fluoresce or phosphoresce are used in the emitting layers. Particular preference is given to systems having three emitting layers, where the three layers exhibit blue, green and orange or red emission (for the basic structure see, for example, WO 2005/011013).

In accordance with the above-mentioned embodiments, the compound according to the invention can be employed in one or more of the various layers mentioned above. As stated above, the electronic properties of the substituents occurring are of importance here.

Preference is given to an electronic device comprising one or more of the compounds according to the invention as electron-transport material, hole-blocking material and/or as matrix material and/or as emitter material.

The materials preferably employed for the respective functions in the electronic devices according to the invention are mentioned below.

Besides the compounds of the formula (I), preferred fluorescent emitter materials are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position. Further preferred emitter materials are selected from indenofluorenamines or indenofluorenediamines, for example in accordance with WO 06/122630, benzoindenofluorenamines or benzoindenofluorenediamines, for example in accordance with WO 08/006449, and dibenzoindenofluorenamines or dibenzoindenofluorenediamines, for example in accordance with WO 07/140847. Examples of emitter materials from the class of the styrylamines are substituted or unsubstituted tristilbenamines or the emitter materials described in WO 06/000388, WO 06/058737, WO 06/000389, WO 07/065549 and WO 07/115610. Preference is furthermore given to the condensed hydrocarbons disclosed in WO 2010/012328.

Suitable fluorescent emitter materials are furthermore the structures depicted in the following table, and the derivatives of these structures disclosed in JP 06/001973, WO 04/047499, WO 06/098080, WO 07/065678, US 2005/0260442 and WO 04/092111.

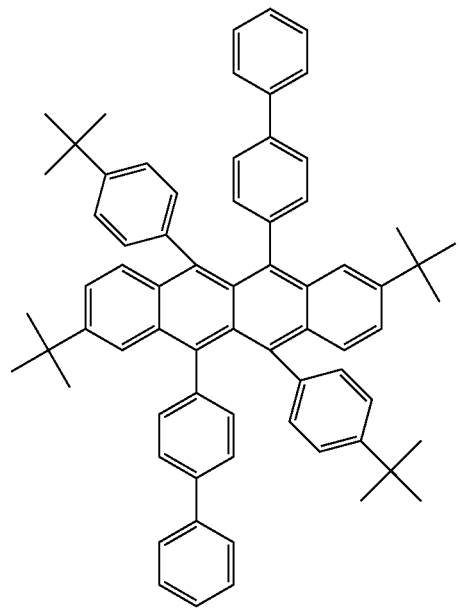 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]

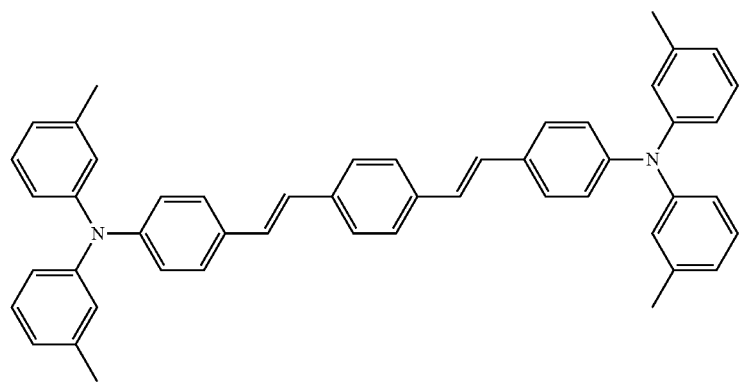 [SMILES: Cc1cccc(N(c2ccc(/C=C/c3ccc(/C=C/c4ccc(N(c5cccc(C)c5)c5cccc(C)c5)cc4)cc3)cc2)c2cccc(C)c2)c1]

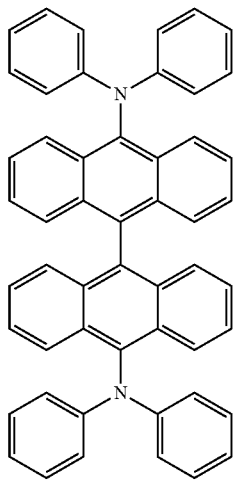 [SMILES: c1ccc(N(c2ccccc2)c2c3ccccc3c(-c3c4ccccc4c(N(c4ccccc4)c4ccccc4)c4ccccc34)c3ccccc23)cc1]
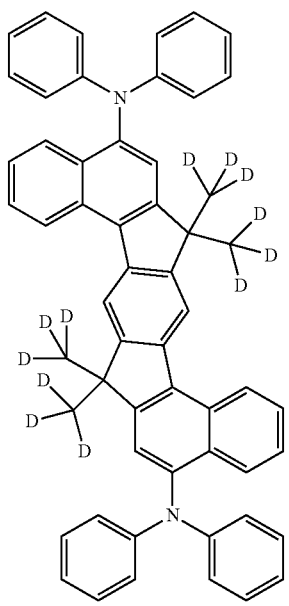 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

-continued
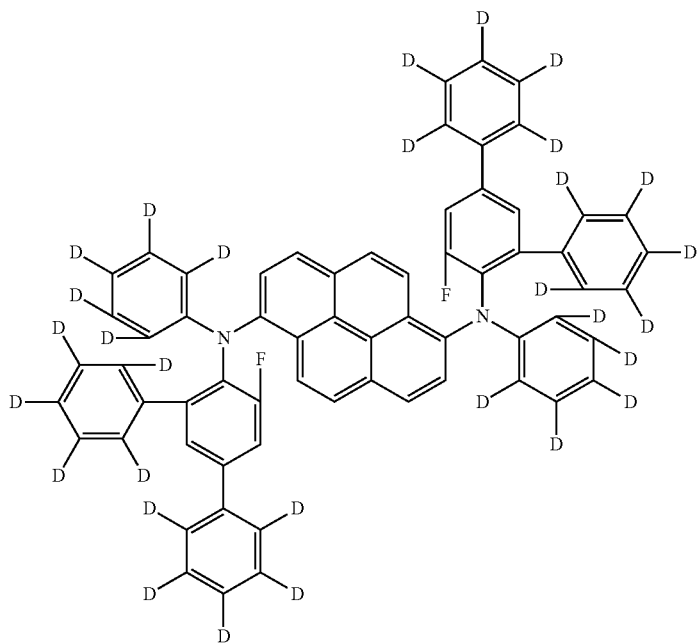 [SMILES: [2H]c1c([2H])c([2H])c(-c2cc(F)c(N(c3c([2H])c([2H])c([2H])c([2H])c3[2H])c3ccc4ccc5c(N(c6c(F)cc(-c7c([2H])c([2H])c([2H])c([2H])c7[2H])cc6-c6c([2H])c([2H])c([2H])c([2H])c6[2H])c6c([2H])c([2H])c([2H])c([2H])c6[2H])ccc6ccc3c4c65)c(-c3c([2H])c([2H])c([2H])c([2H])c3[2H])c2)c([2H])c1[2H]]
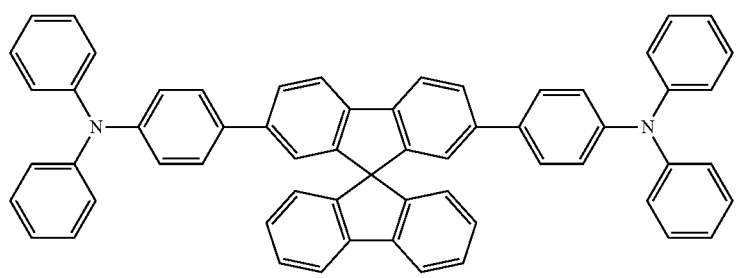 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-4)cc2)cc1]
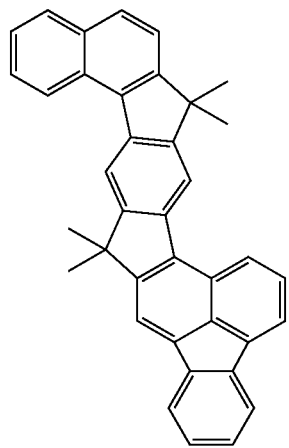 [SMILES: CC1(C)c2cc3c(cc2-c2c1ccc1ccccc21)C(C)(C)c1cc2c4c(cccc4c1-3)-c1ccccc1-2]

-continued
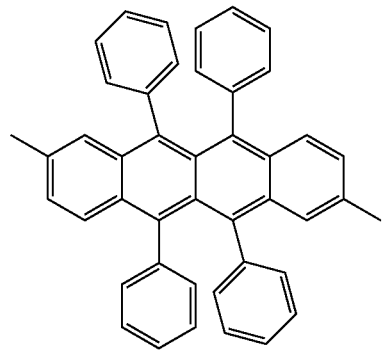
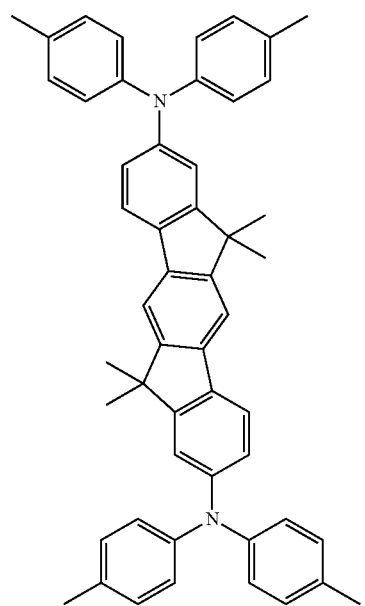
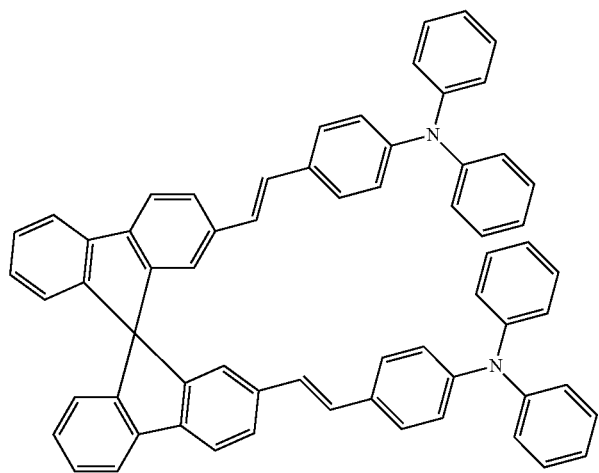 [SMILES: C(=C\c1ccc2c(c1)C1(c3ccccc3-2)c2ccccc2-c2ccc(/C=C/c3ccc(N(c4ccccc4)c4ccccc4)cc3)cc21)/c1ccc(N(c2ccccc2)c2ccccc2)cc1]

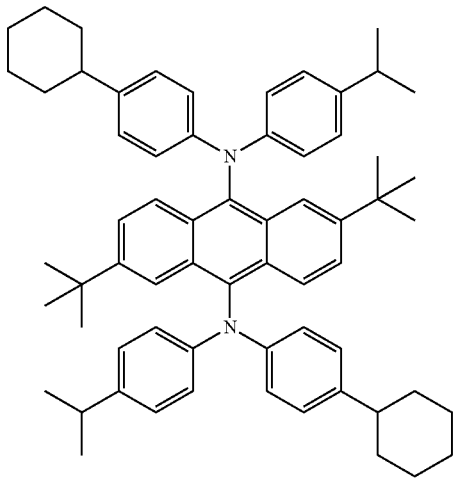 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
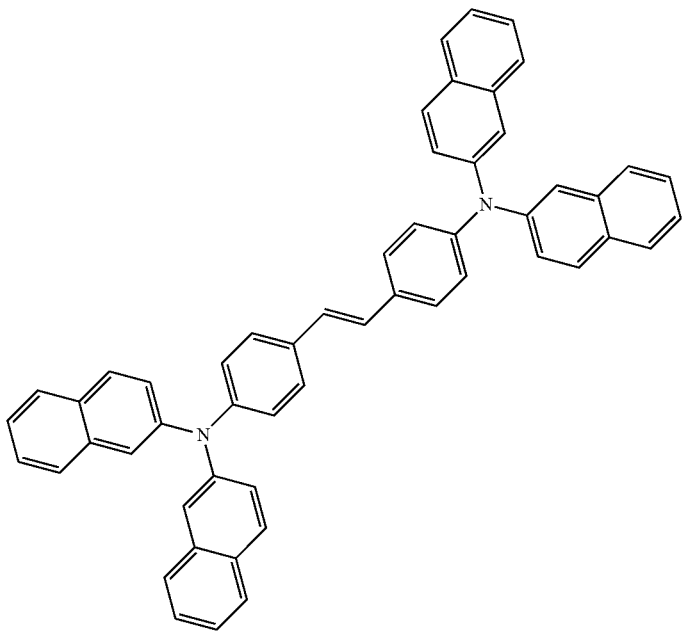 [SMILES: C(=C\c1ccc(N(c2ccc3ccccc3c2)c2ccc3ccccc3c2)cc1)/c1ccc(N(c2ccc3ccccc3c2)c2ccc3ccccc3c2)cc1]

-continued
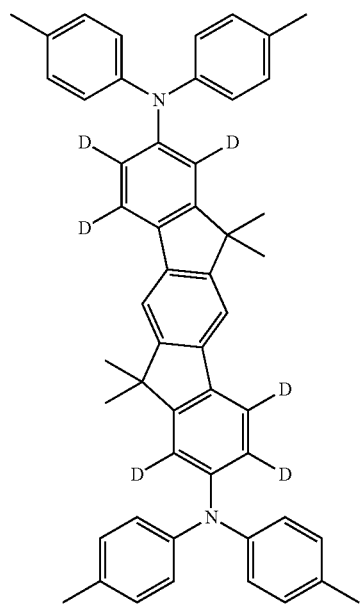
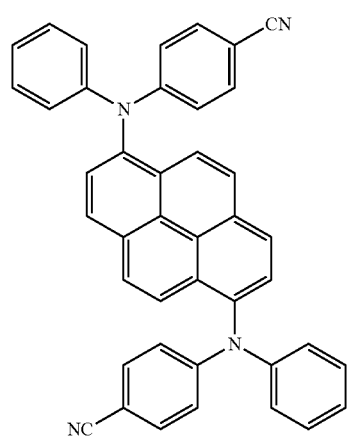 [SMILES: N#Cc1ccc(N(c2ccccc2)c2ccc3ccc4c(N(c5ccccc5)c5ccc(C#N)cc5)ccc5ccc2c3c54)cc1]

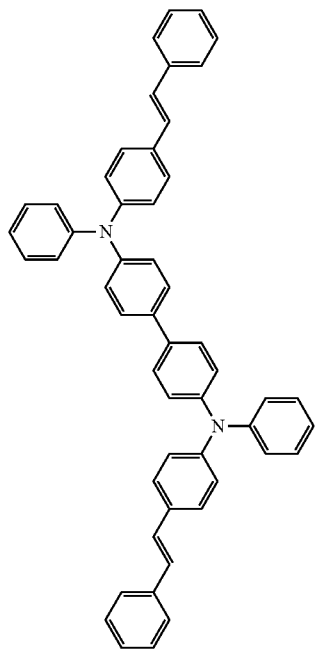 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
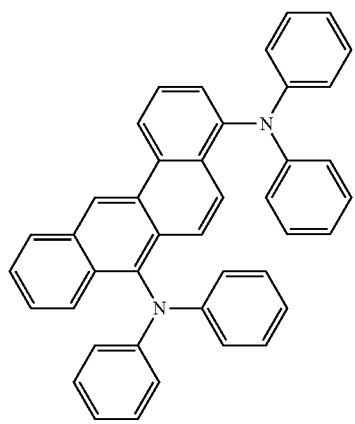 [SMILES: c1ccc(N(c2ccccc2)c2cccc3c2ccc2c(N(c4ccccc4)c4ccccc4)c4ccccc4cc23)cc1]
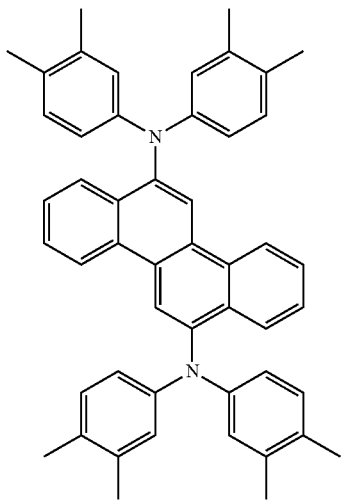

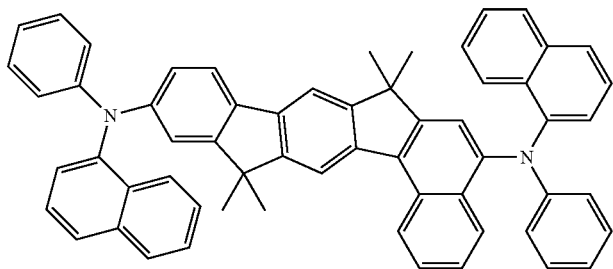 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
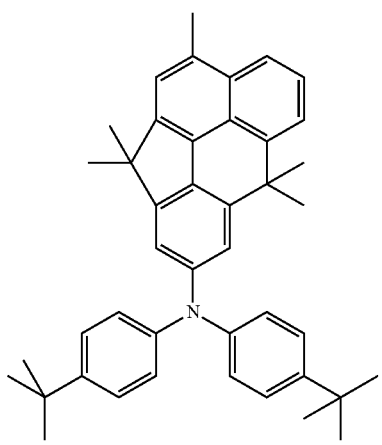 [SMILES: Cc1cc2c3c4c(cccc14)C(C)(C)c1cc(N(c4ccc(C(C)(C)C)cc4)c4ccc(C(C)(C)C)cc4)cc(c1-3)C2(C)C]
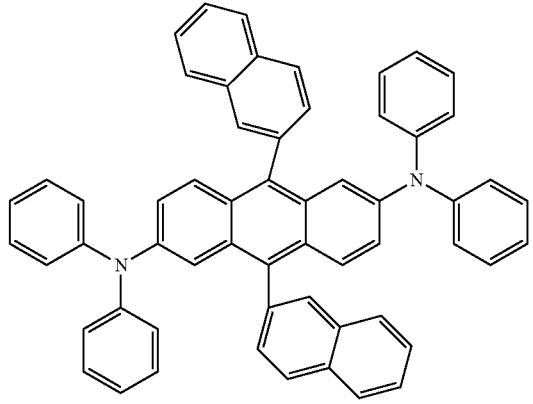 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
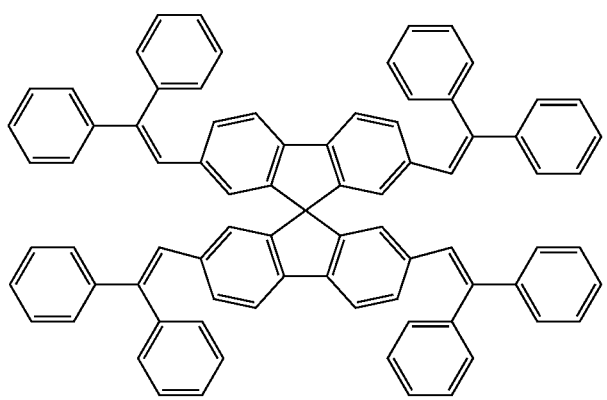 [SMILES: C(=C(c1ccccc1)c1ccccc1)c1ccc2c(c1)C1(c3cc(C=C(c4ccccc4)c4ccccc4)ccc3-2)c2cc(C=C(c3ccccc3)c3ccccc3)ccc2-c2ccc(C=C(c3ccccc3)c3ccccc3)cc21]

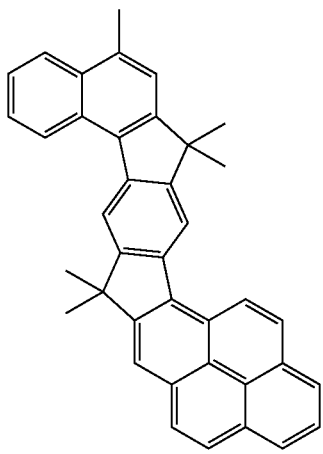 [SMILES: Cc1cc2c(c3ccccc13)-c1cc3c(cc1C2(C)C)-c1c(cc2ccc4cccc5ccc1c2c45)C3(C)C]
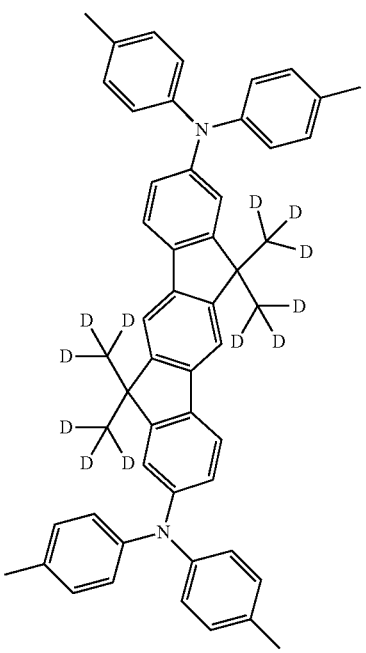
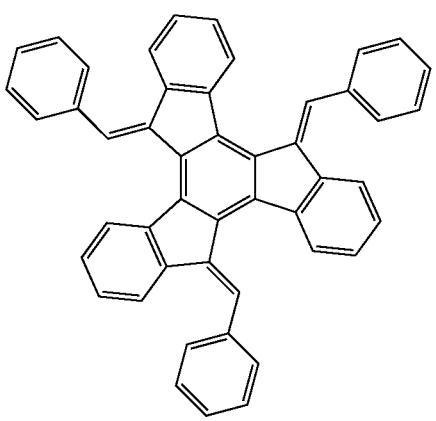 [SMILES: C(=C1/c2ccccc2-c2c1c1c(c3c2/C(=C/c2ccccc2)c2ccccc2-3)/C(=C/c2ccccc2)c2ccccc2-1)/c1ccccc1]

-continued
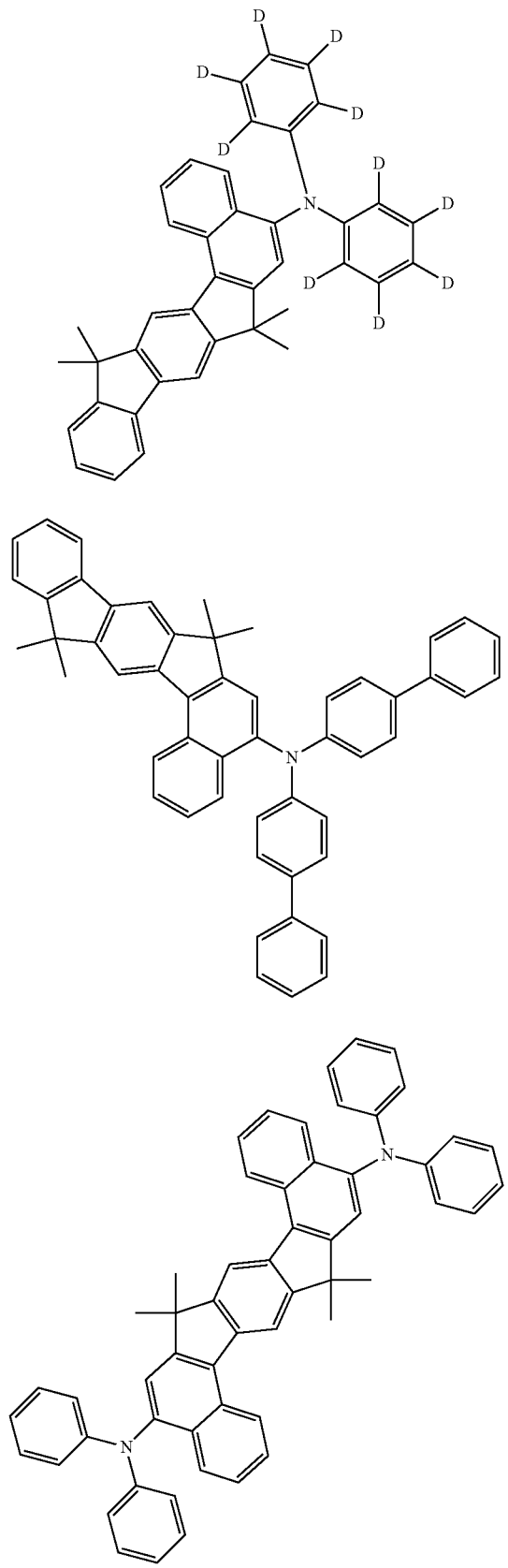

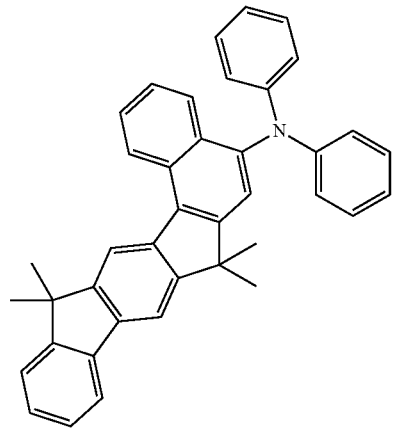 [SMILES: CC1(C)c2ccccc2-c2cc3c(cc21)-c1c(cc(N(c2ccccc2)c2ccccc2)c2ccccc12)C3(C)C]
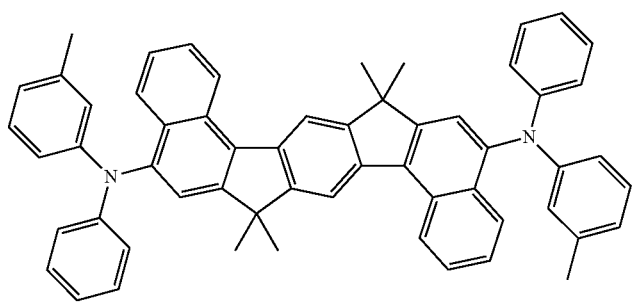 [SMILES: Cc1cccc(N(c2ccccc2)c2cc3c(c4ccccc24)-c2cc4c(cc2C3(C)C)-c2c(cc(N(c3ccccc3)c3cccc(C)c3)c3ccccc23)C4(C)C)c1]
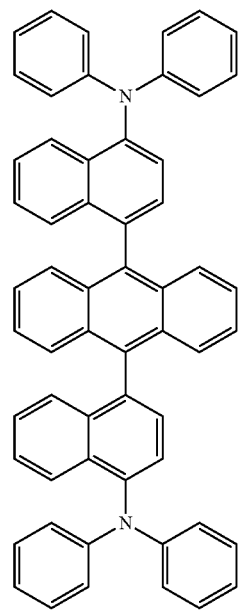 [SMILES: c1ccc(N(c2ccccc2)c2ccc(-c3c4ccccc4c(-c4ccc(N(c5ccccc5)c5ccccc5)c5ccccc45)c4ccccc34)c3ccccc23)cc1]

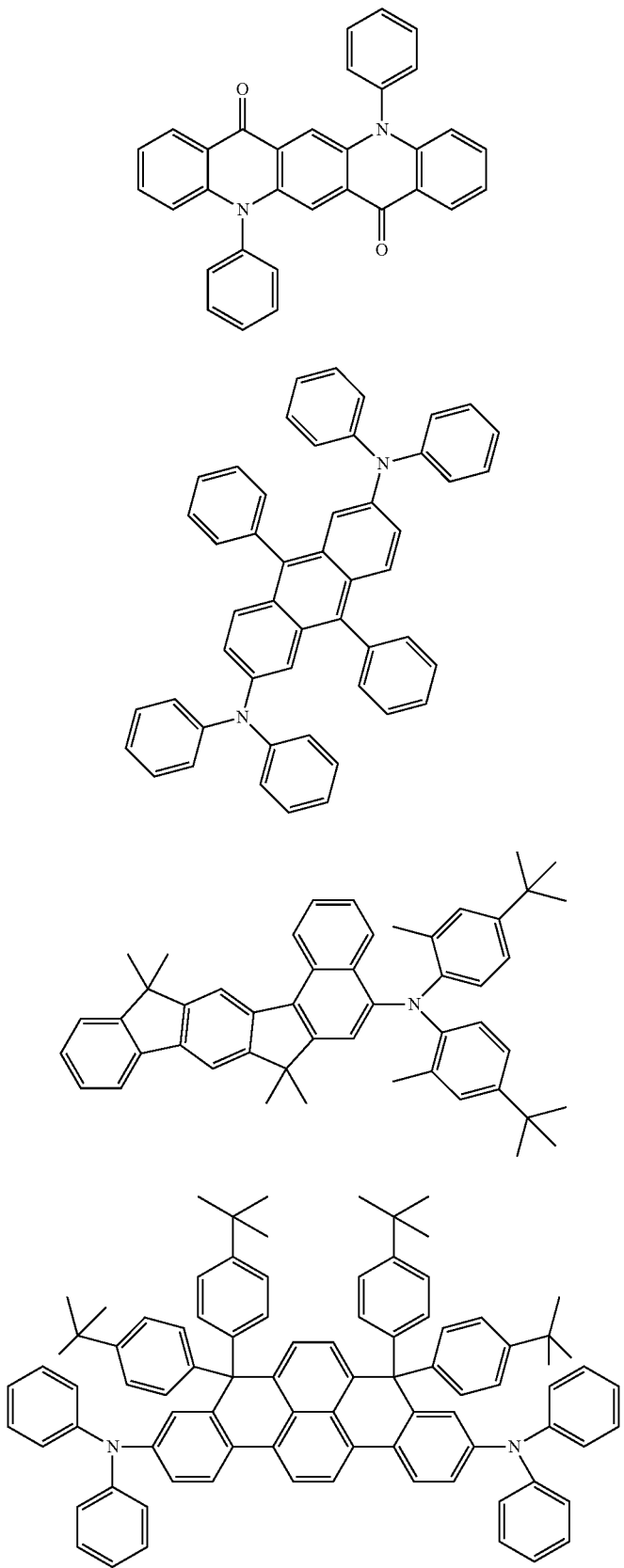

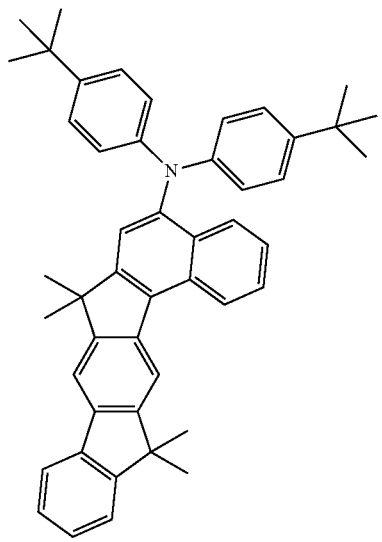 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
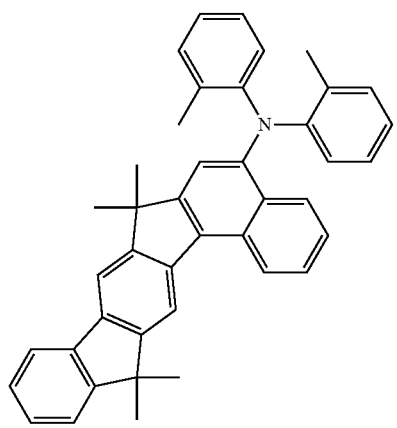 [SMILES: Cc1ccccc1N(c1ccccc1C)c1cc2c(c3ccccc13)-c1cc3c(cc1C2(C)C)-c1ccccc1C3(C)C]
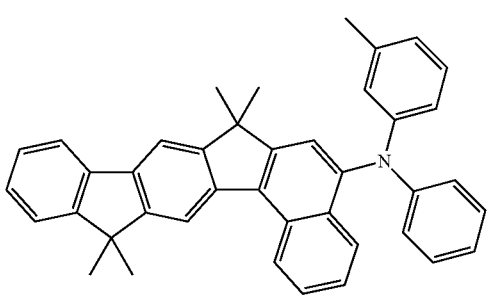 [SMILES: Cc1cccc(N(c2ccccc2)c2cc3c(c4ccccc24)-c2cc4c(cc2C3(C)C)-c2ccccc2C4(C)C)c1]
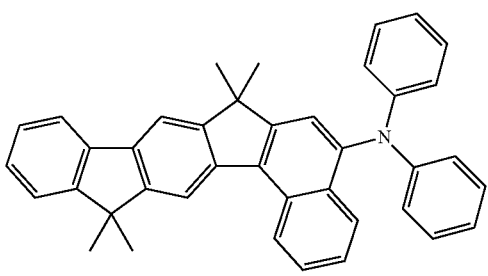 [SMILES: CC1(C)c2ccccc2-c2cc3c(cc21)-c1c(cc(N(c2ccccc2)c2ccccc2)c2ccccc12)C3(C)C]

-continued
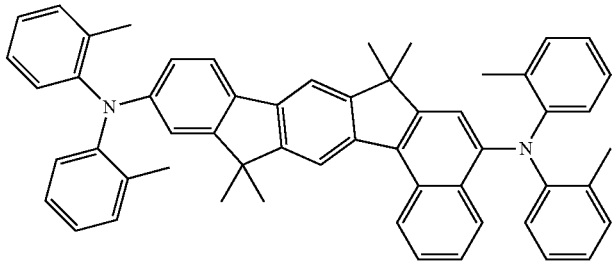 [SMILES: Cc1ccccc1N(c1ccc2c(c1)C(C)(C)c1cc3c(cc1-2)C(C)(C)c1cc(N(c2ccccc2C)c2ccccc2C)c2ccccc2c1-3)c1ccccc1C]
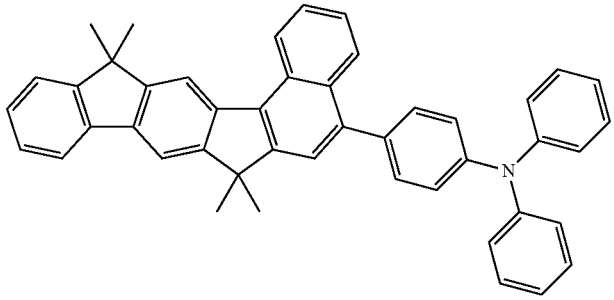 [SMILES: CC1(C)c2ccccc2-c2cc3c(cc21)-c1c(cc(-c2ccc(N(c4ccccc4)c4ccccc4)cc2)c2ccccc12)C3(C)C]
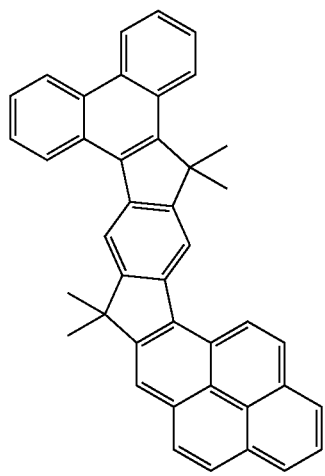 [SMILES: CC1(C)c2cc3c(cc2-c2c1cc1ccc4cccc5ccc2c1c45)C(C)(C)c1c-3c2ccccc2c2ccccc12]
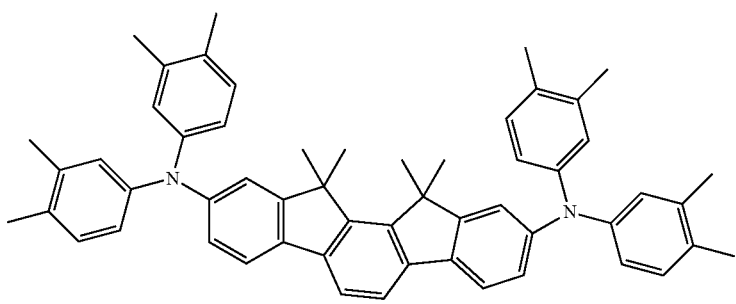
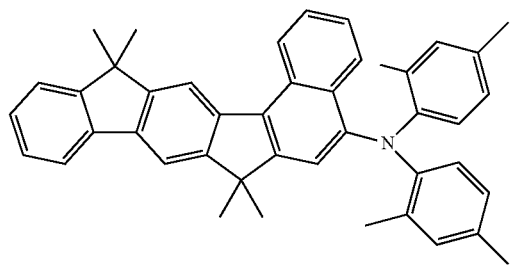 [SMILES: Cc1ccc(N(c2ccc(C)cc2C)c2cc3c(c4ccccc24)-c2cc4c(cc2C3(C)C)-c2ccccc2C4(C)C)c(C)c1]

-continued
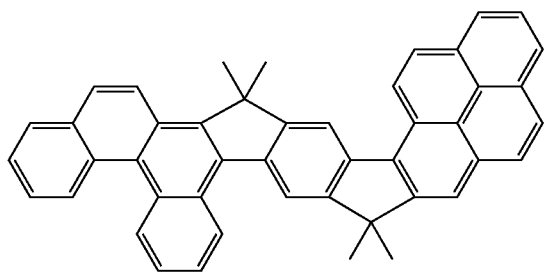 [SMILES: CC1(C)c2cc3c(cc2-c2c1cc1ccc4cccc5ccc2c1c45)C(C)(C)c1c-3c2ccccc2c2c1ccc1ccccc12]
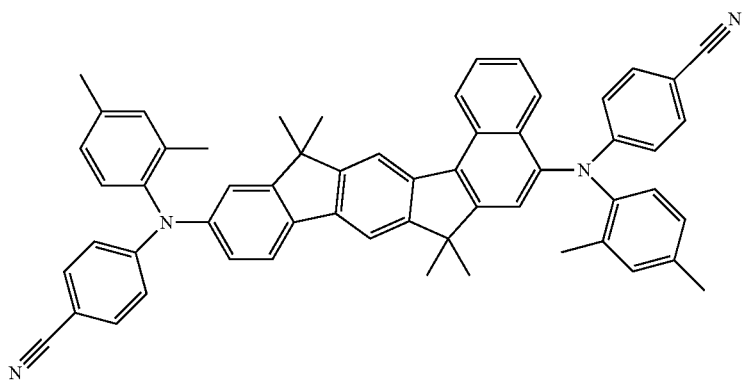 [SMILES: Cc1ccc(N(c2ccc(C#N)cc2)c2ccc3c(c2)C(C)(C)c2cc4c(cc2-3)C(C)(C)c2cc(N(c3ccc(C#N)cc3)c3ccc(C)cc3C)c3ccccc3c2-4)c(C)c1]
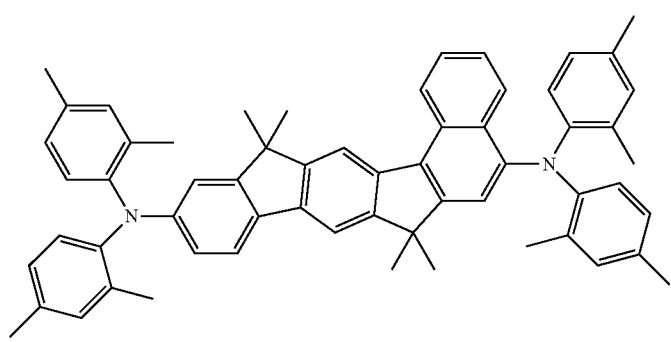
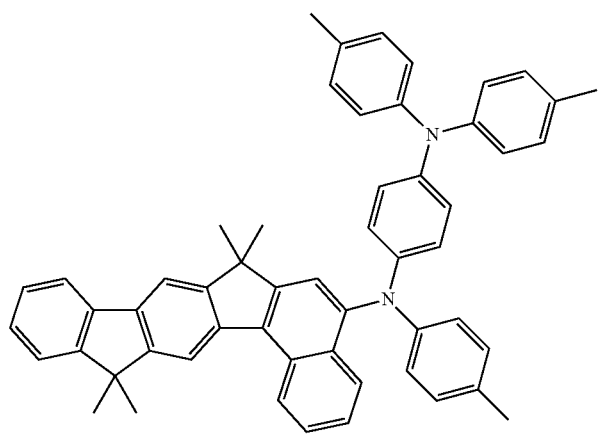 [SMILES: Cc1ccc(N(c2ccc(C)cc2)c2ccc(N(c3ccc(C)cc3)c3cc4c(c5ccccc35)-c3cc5c(cc3C4(C)C)-c3ccccc3C5(C)C)cc2)cc1]

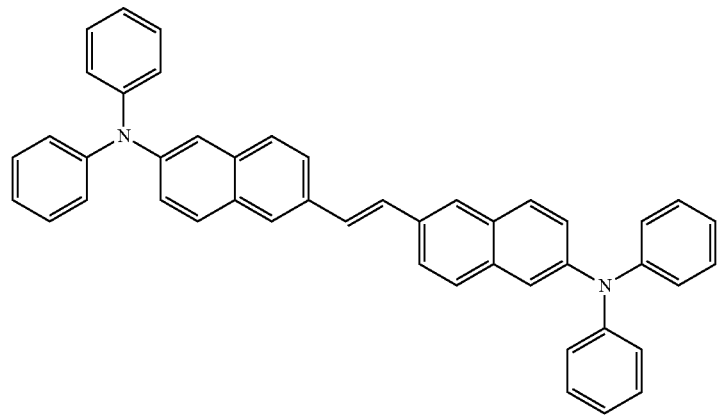 [SMILES: C(=C\c1ccc2cc(N(c3ccccc3)c3ccccc3)ccc2c1)/c1ccc2cc(N(c3ccccc3)c3ccccc3)ccc2c1]

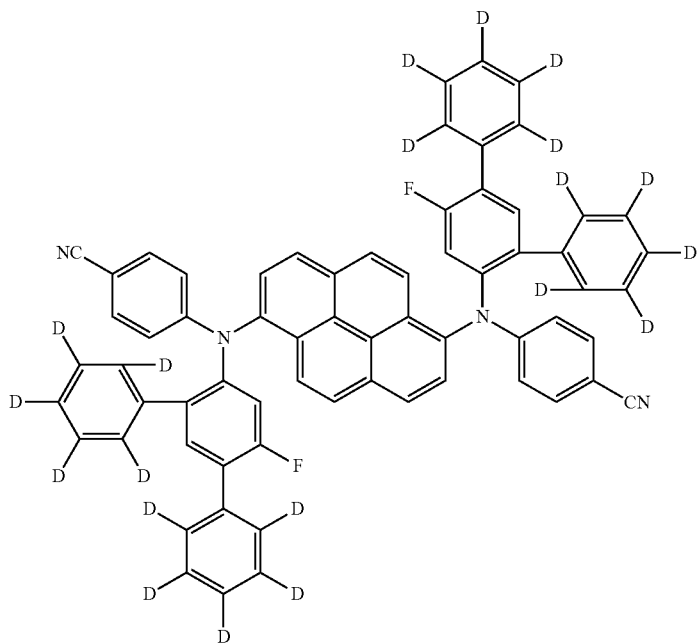 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

Suitable matrix materials in the electronic devices according to the invention are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 04/081017), the hole-conducting compounds (for example in accordance with WO 04/058911), the electron-conducting compounds, in particular ketones, phosphine oxides, sulfoxides, etc. (for example in accordance with WO 05/084081 and WO 05/084082), the atropisomers (for example in accordance with WO 06/048268), the boronic acid derivatives (for example in accordance with WO 06/117052) or the benzanthracenes (for example in accordance with WO 08/145239). Suitable matrix materials are furthermore also the compounds according to the invention. [lacuna] comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Suitable matrix materials are, for example, the materials depicted in the following table, and derivatives of these materials, as disclosed in WO 04/018587, WO 08/006449, U.S. Pat. No. 5,935,721, US 2005/0181232, JP 2000/273056, EP 681019, US 2004/0247937 and US 2005/0211958.

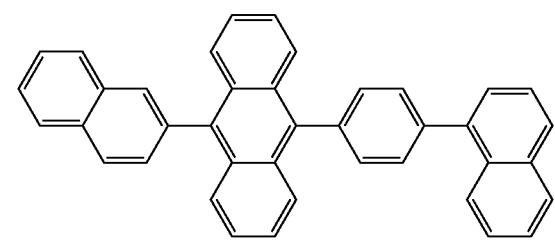 [SMILES: c1ccc2cc(-c3c4ccccc4c(-c4ccc(-c5cccc6ccccc56)cc4)c4ccccc34)ccc2c1]
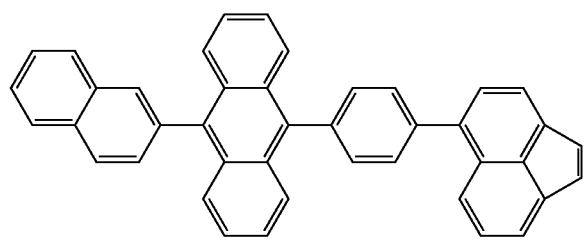 [SMILES: C1=Cc2ccc(-c3ccc(-c4c5ccccc5c(-c5ccc6ccccc6c5)c5ccccc45)cc3)c3cccc1c23]
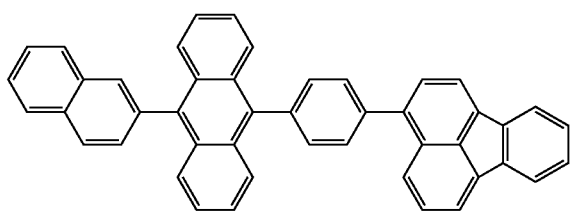 [SMILES: c1ccc2c(c1)-c1cccc3c(-c4ccc(-c5c6ccccc6c(-c6ccc7ccccc7c6)c6ccccc56)cc4)ccc-2c13]
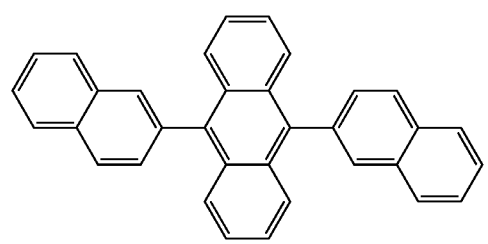 [SMILES: c1ccc2cc(-c3c4ccccc4c(-c4ccc5ccccc5c4)c4ccccc34)ccc2c1]
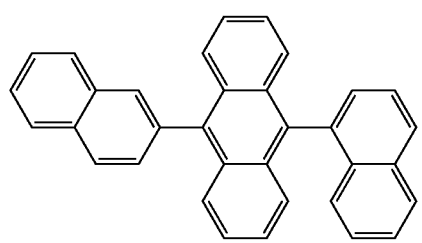 [SMILES: c1ccc2cc(-c3c4ccccc4c(-c4cccc5ccccc45)c4ccccc34)ccc2c1]
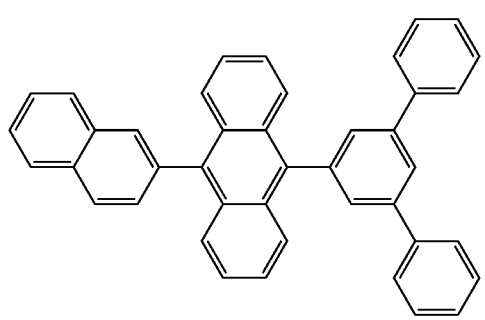 [SMILES: c1ccc(-c2cc(-c3ccccc3)cc(-c3c4ccccc4c(-c4ccc5ccccc5c4)c4ccccc34)c2)cc1]
-continued
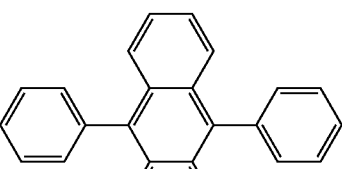
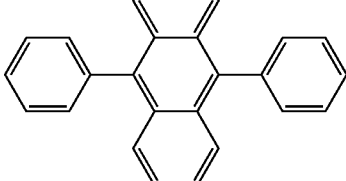
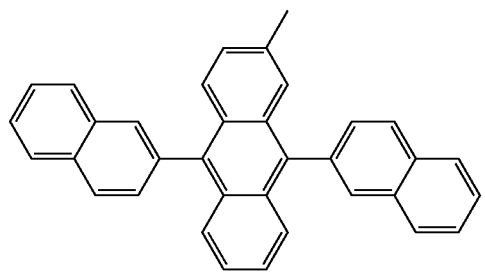 [SMILES: Cc1ccc2c(-c3ccc4ccccc4c3)c3ccccc3c(-c3ccc4ccccc4c3)c2c1]
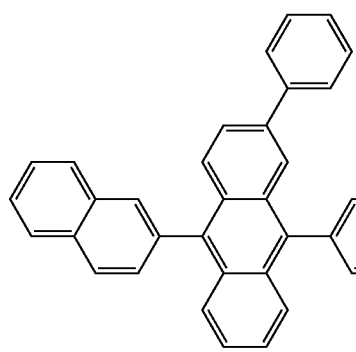
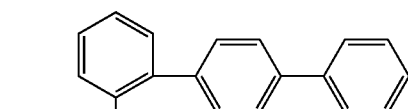
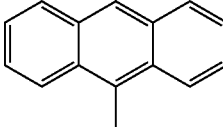
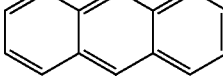
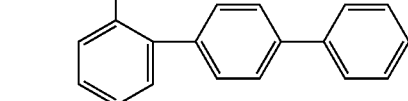

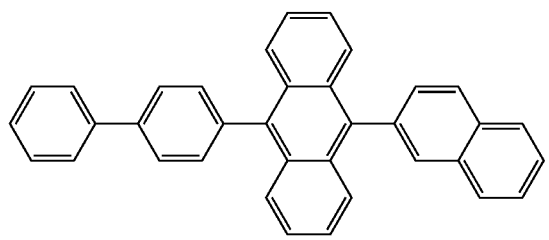 [SMILES: c1ccc(-c2ccc(-c3c4ccccc4c(-c4ccc5ccccc5c4)c4ccccc34)cc2)cc1]
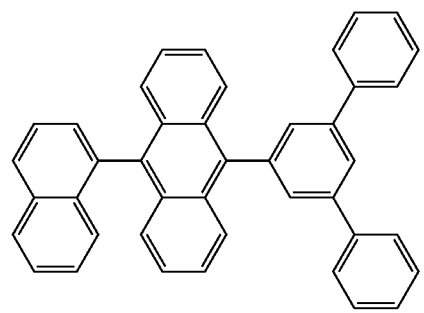 [SMILES: c1ccc(-c2cc(-c3ccccc3)cc(-c3c4ccccc4c(-c4cccc5ccccc45)c4ccccc34)c2)cc1]
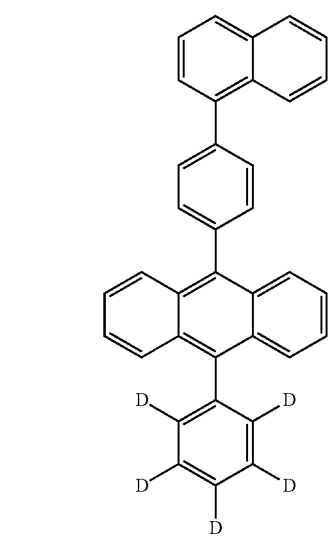 [SMILES: [2H]c1c([2H])c([2H])c(-c2c3ccccc3c(-c3ccc(-c4cccc5ccccc45)cc3)c3ccccc23)c([2H])c1[2H]]
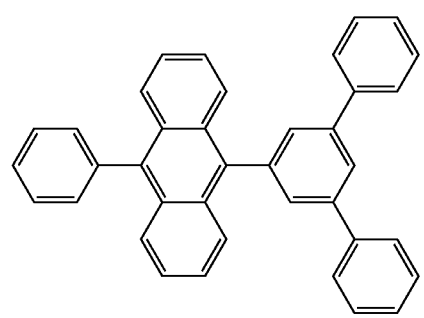 [SMILES: c1ccc(-c2cc(-c3ccccc3)cc(-c3c4ccccc4c(-c4ccccc4)c4ccccc34)c2)cc1]
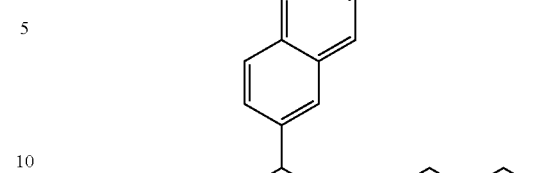
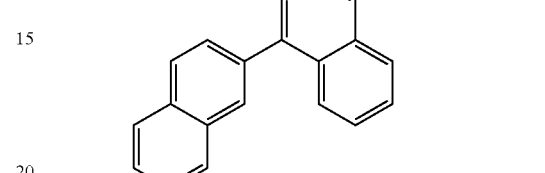
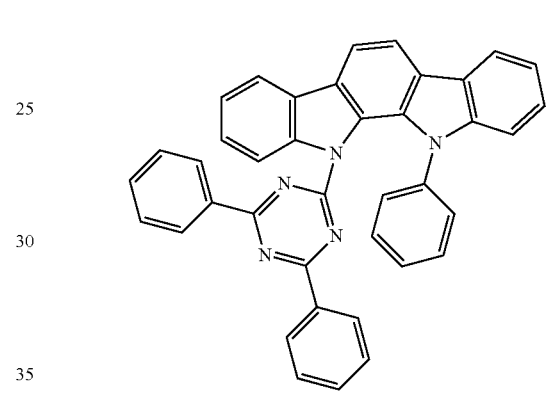
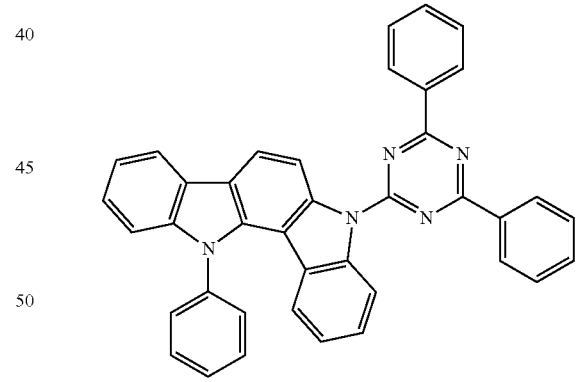
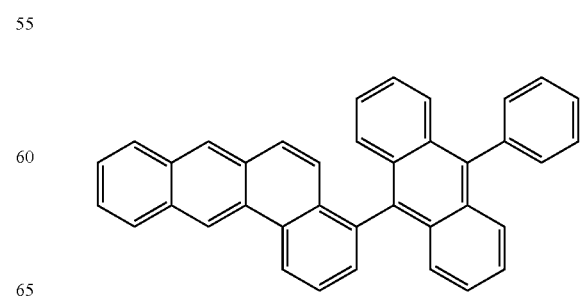

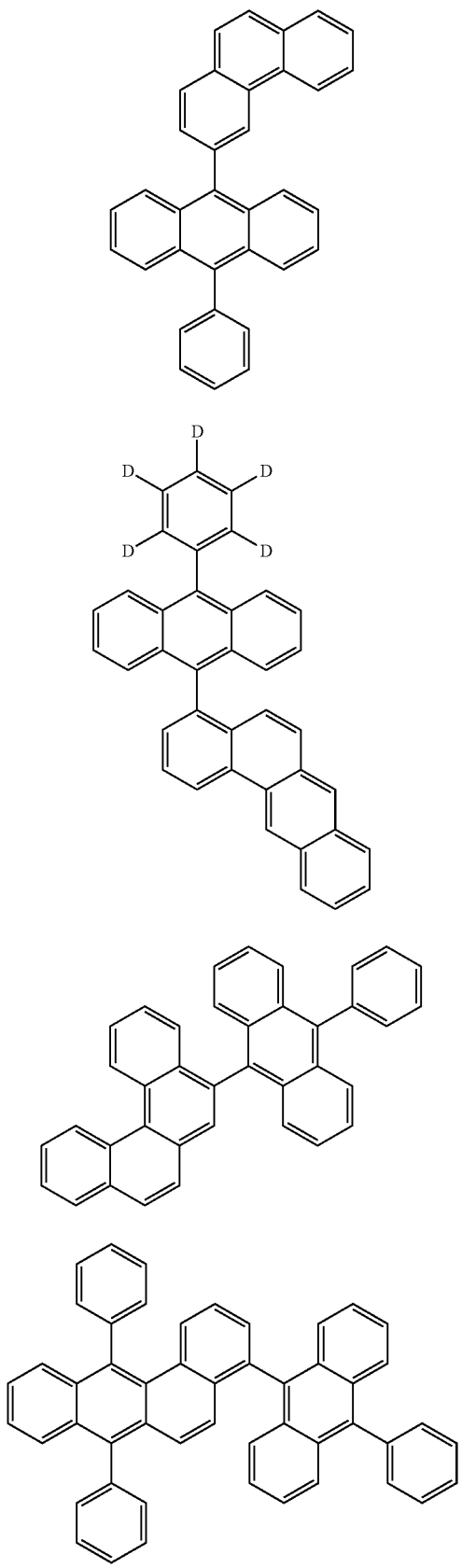
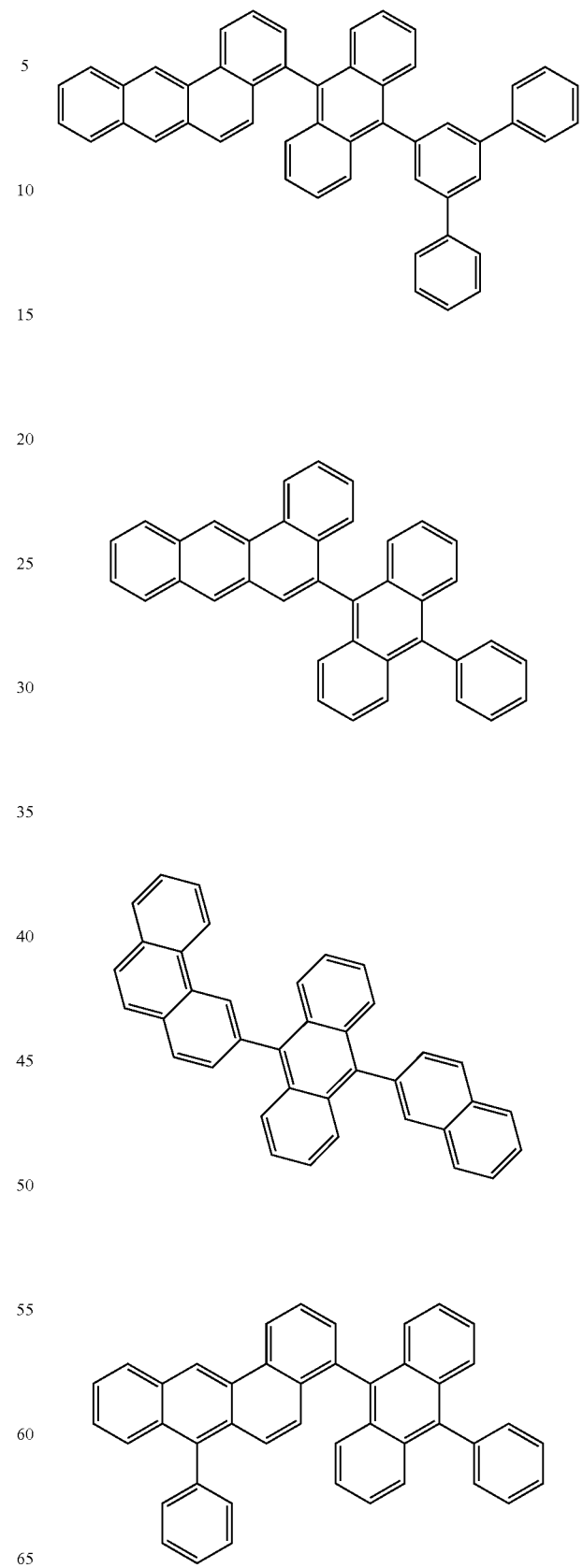

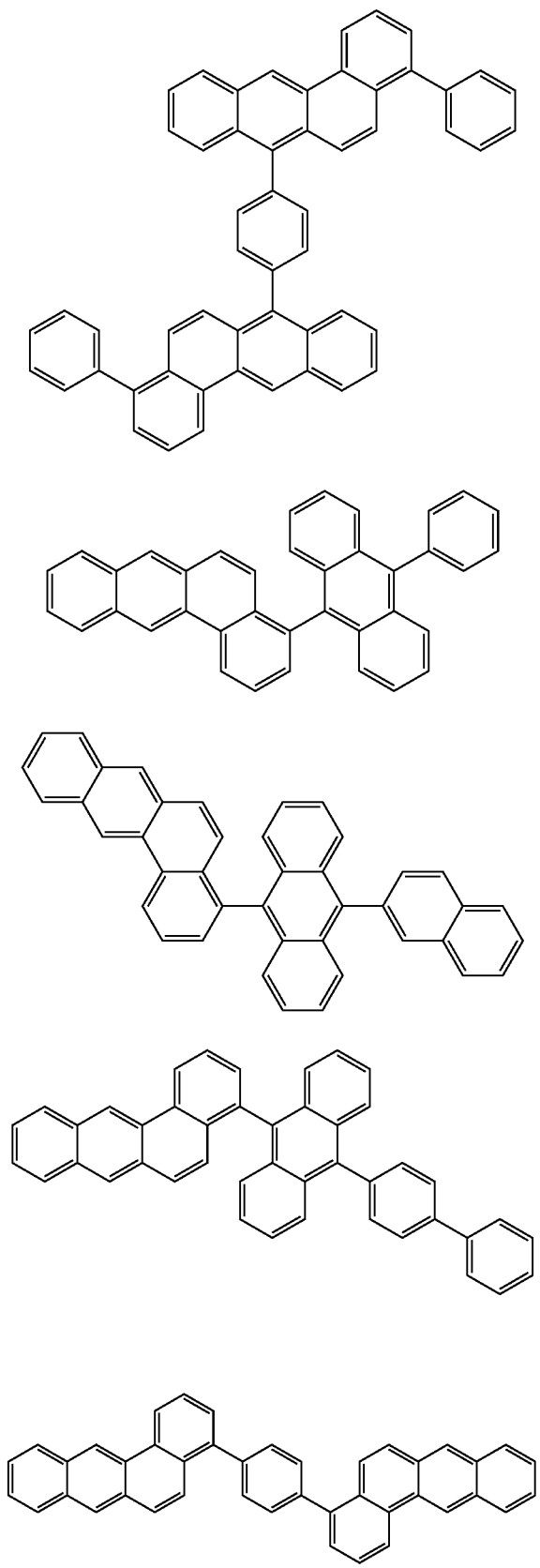
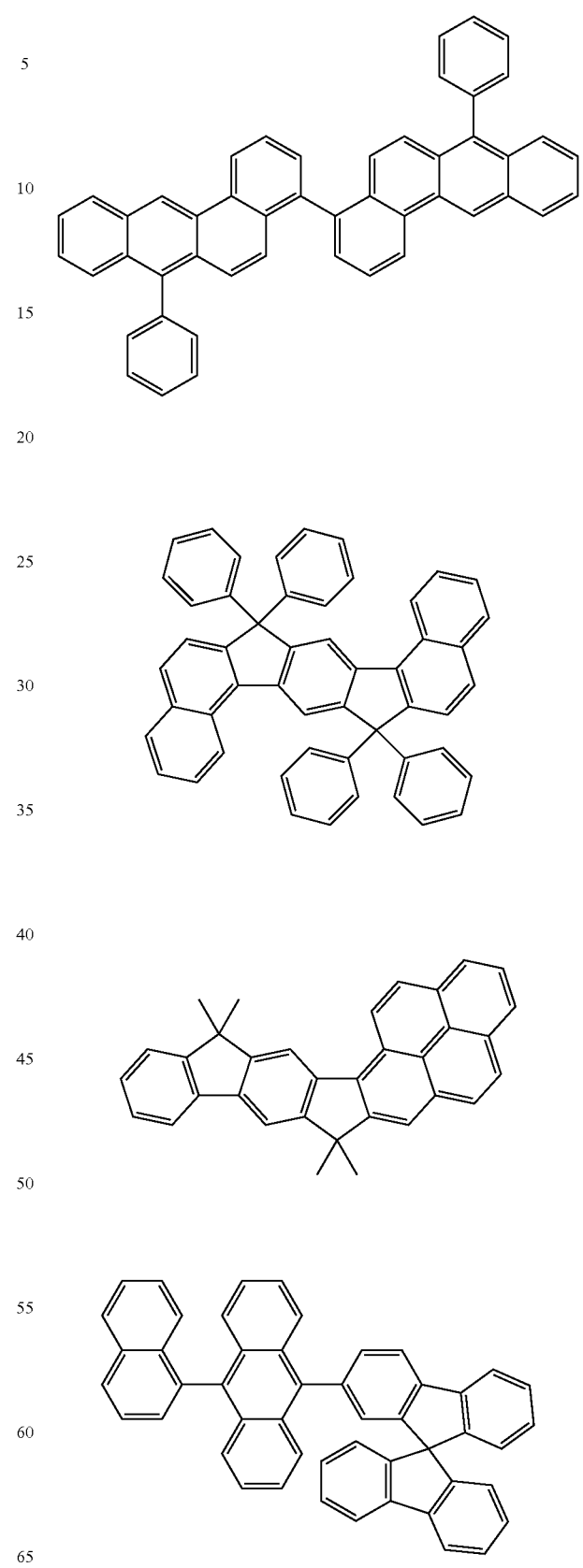

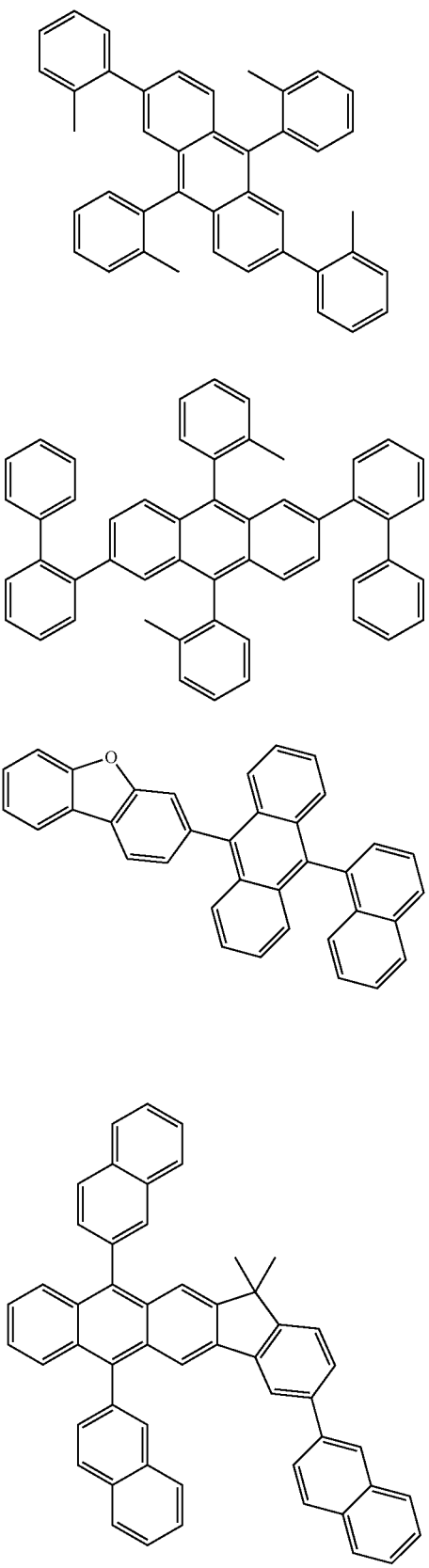

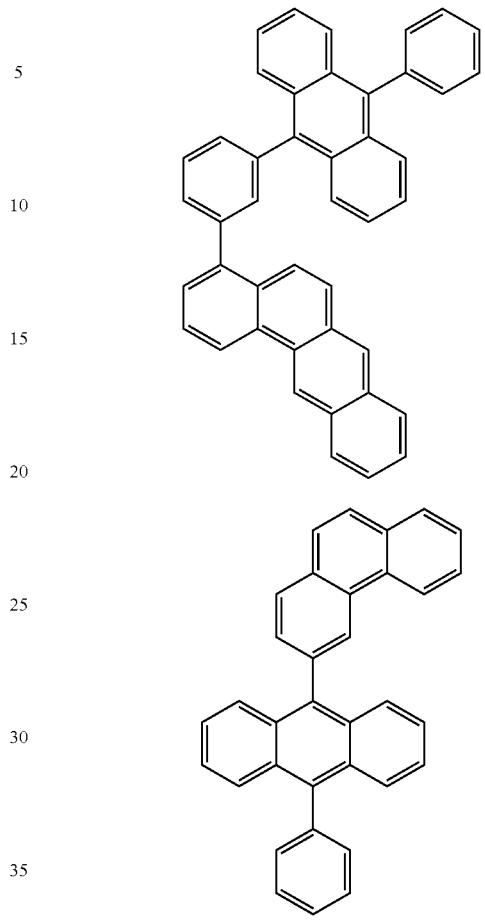

Suitable charge-transport materials, as can be used in the hole-injection or hole-transport layer of the organic electroluminescent device according to the invention, are, for example, the compounds disclosed in Y. Shirota et al., *Chem. Rev.* 2007, 107(4), 953-1010, or other materials as are employed in these layers in accordance with the prior art.

Examples of preferred hole-transport materials which can be used in a hole-transport or hole-injection layer in the electroluminescent device according to the invention are indenofluorenamines and derivatives (for example in accordance with WO 06/122630 or WO 06/100896), the amine derivatives disclosed in EP 1661888, hexaazatriphenylene derivatives (for example in accordance with WO 01/049806), amine derivatives containing condensed aromatic rings (for example in accordance with U.S. Pat. No. 5,061,569), the amine derivatives disclosed in WO 95/09147, monobenzoindenofluorenamines (for example in accordance with WO 08/006449) or dibenzoindenofluorenamines (for example in accordance with WO 07/140847). Hole-transport and hole-injection materials which are furthermore suitable are compounds as disclosed in JP 2001/226331, EP 676461, EP 650955, WO 01/049806, U.S. Pat. No. 4,780,536, WO 98/30071, EP 891121, EP 1661888, JP 2006/253445, EP 650955, WO 06/073054 and U.S. Pat. No. 5,061,569.

Suitable hole-transport or hole-injection materials are furthermore, for example, the materials shown in the following table.

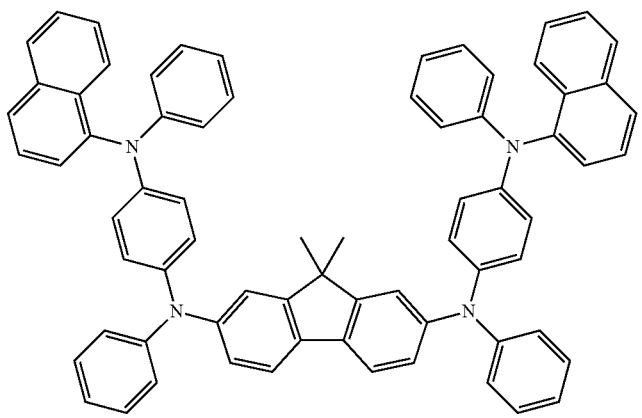 [SMILES: CC1(C)c2cc(N(c3ccccc3)c3ccc(N(c4ccccc4)c4cccc5ccccc45)cc3)ccc2-c2ccc(N(c3ccccc3)c3ccc(N(c4ccccc4)c4cccc5ccccc45)cc3)cc21]
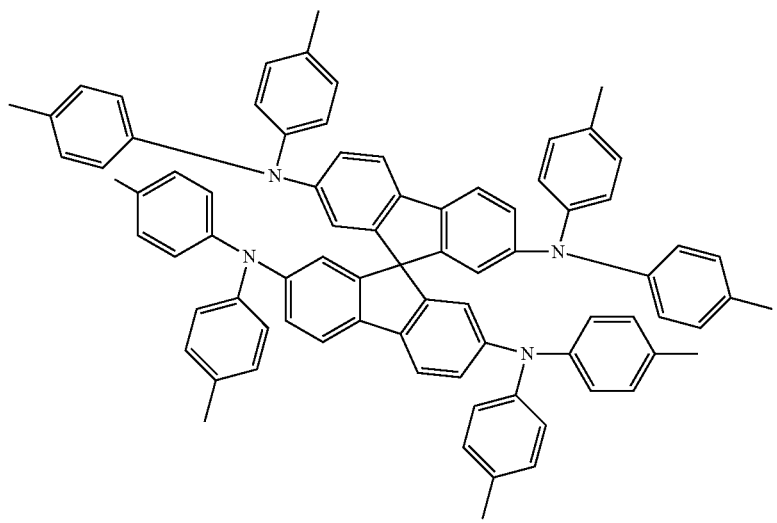
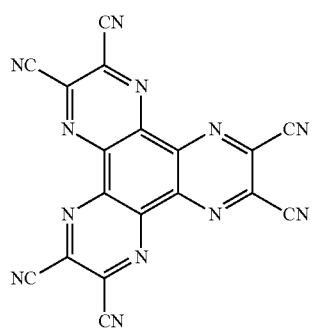 [SMILES: N#Cc1nc2c3nc(C#N)c(C#N)nc3c3nc(C#N)c(C#N)nc3c2nc1C#N]
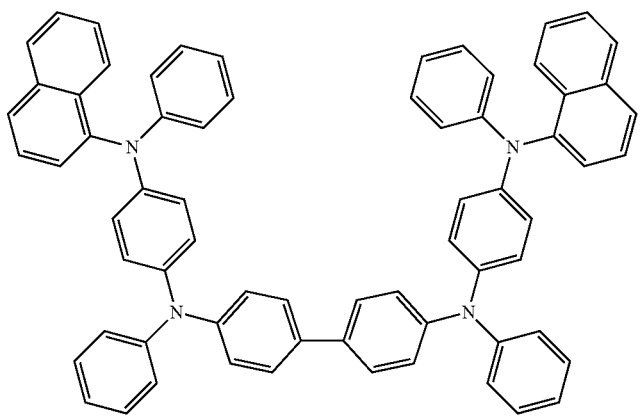 [SMILES: c1ccc(N(c2ccc(-c3ccc(N(c4ccccc4)c4ccc(N(c5ccccc5)c5cccc6ccccc56)cc4)cc3)cc2)c2ccc(N(c3ccccc3)c3cccc4ccccc34)cc2)cc1]

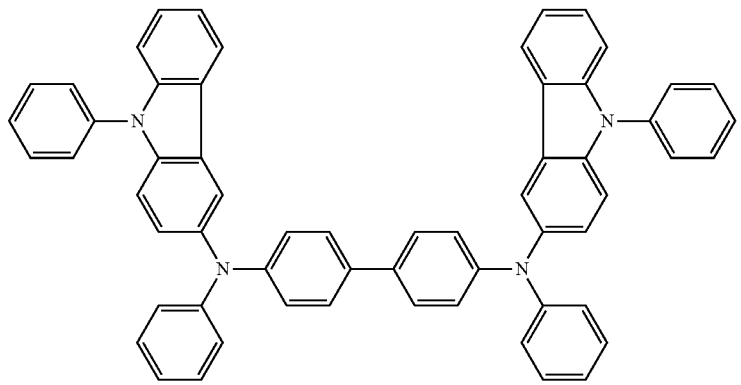 [SMILES: c1ccc(N(c2ccc(-c3ccc(N(c4ccccc4)c4ccc5c(c4)c4ccccc4n5-c4ccccc4)cc3)cc2)c2ccc3c(c2)c2ccccc2n3-c2ccccc2)cc1]
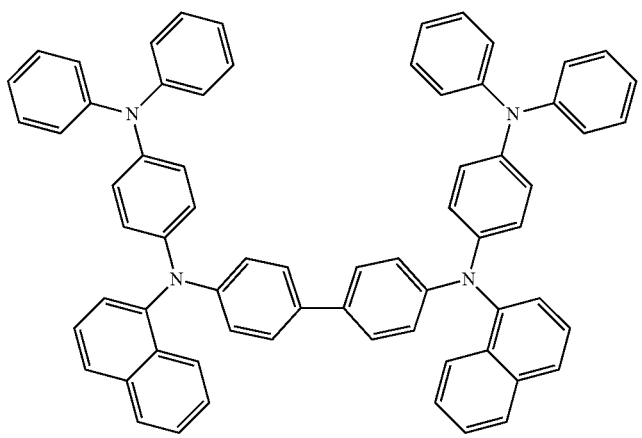 [SMILES: c1ccc(N(c2ccccc2)c2ccc(N(c3ccc(-c4ccc(N(c5ccc(N(c6ccccc6)c6ccccc6)cc5)c5cccc6ccccc56)cc4)cc3)c3cccc4ccccc34)cc2)cc1]
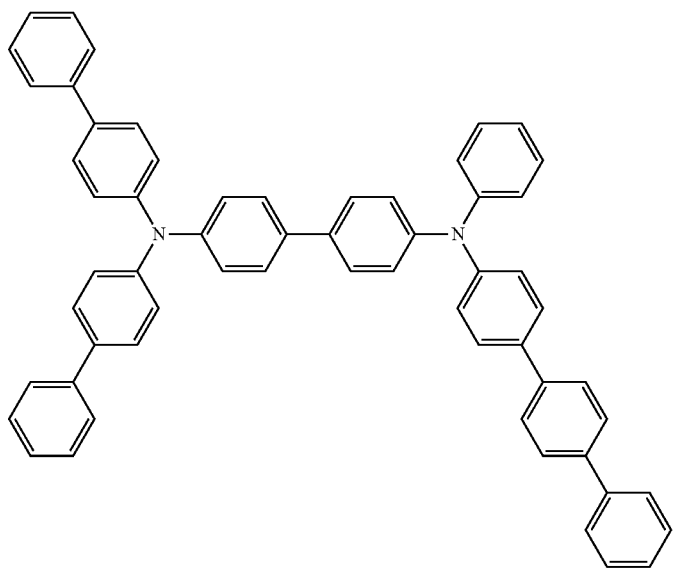 [SMILES: c1ccc(-c2ccc(-c3ccc(N(c4ccccc4)c4ccc(-c5ccc(N(c6ccc(-c7ccccc7)cc6)c6ccc(-c7ccccc7)cc6)cc5)cc4)cc3)cc2)cc1]

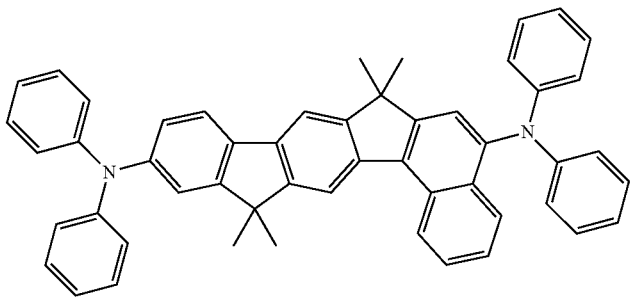 [SMILES: CC1(C)c2cc(N(c3ccccc3)c3ccccc3)ccc2-c2cc3c(cc21)-c1c(cc(N(c2ccccc2)c2ccccc2)c2ccccc12)C3(C)C]
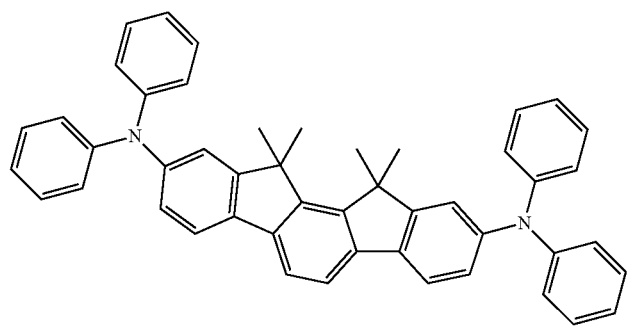 [SMILES: CC1(C)c2cc(N(c3ccccc3)c3ccccc3)ccc2-c2ccc3c(c21)C(C)(C)c1cc(N(c2ccccc2)c2ccccc2)ccc1-3]
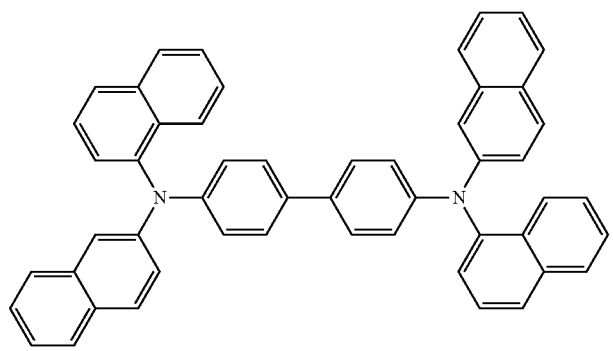 [SMILES: c1ccc2cc(N(c3ccc(-c4ccc(N(c5ccc6ccccc6c5)c5cccc6ccccc56)cc4)cc3)c3cccc4ccccc34)ccc2c1]
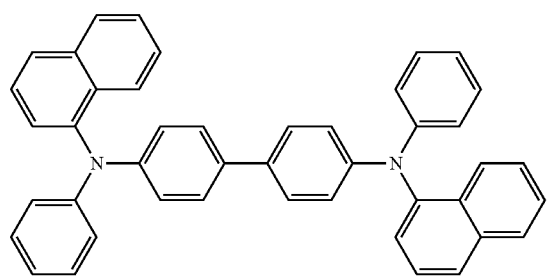 [SMILES: c1ccc(N(c2ccc(-c3ccc(N(c4ccccc4)c4cccc5ccccc45)cc3)cc2)c2cccc3ccccc23)cc1]

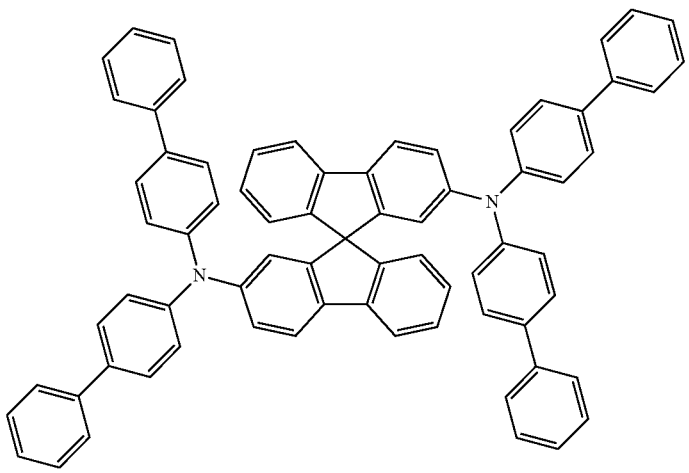 [SMILES: c1ccc(-c2ccc(N(c3ccc(-c4ccccc4)cc3)c3ccc4c(c3)C3(c5ccccc5-4)c4ccccc4-c4ccc(N(c5ccc(-c6ccccc6)cc5)c5ccc(-c6ccccc6)cc5)cc43)cc2)cc1]
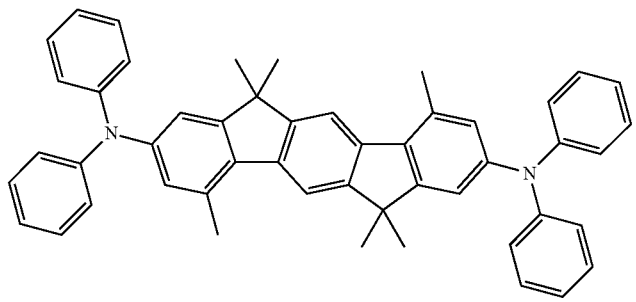 [SMILES: Cc1cc(N(c2ccccc2)c2ccccc2)cc2c1-c1cc3c(cc1C2(C)C)-c1c(C)cc(N(c2ccccc2)c2ccccc2)cc1C3(C)C]
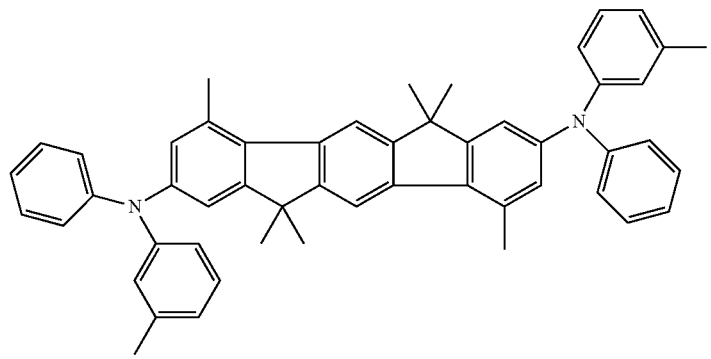 [SMILES: Cc1cccc(N(c2ccccc2)c2cc(C)c3c(c2)C(C)(C)c2cc4c(cc2-3)C(C)(C)c2cc(N(c3ccccc3)c3cccc(C)c3)cc(C)c2-4)c1]
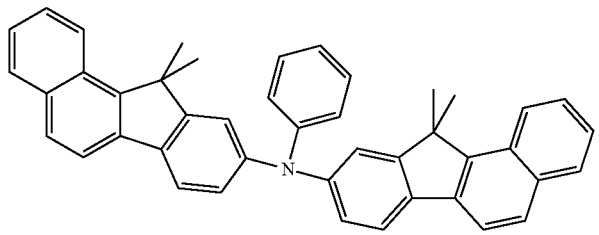 [SMILES: CC1(C)c2cc(N(c3ccccc3)c3ccc4c(c3)C(C)(C)c3c-4ccc4ccccc34)ccc2-c2ccc3ccccc3c21]

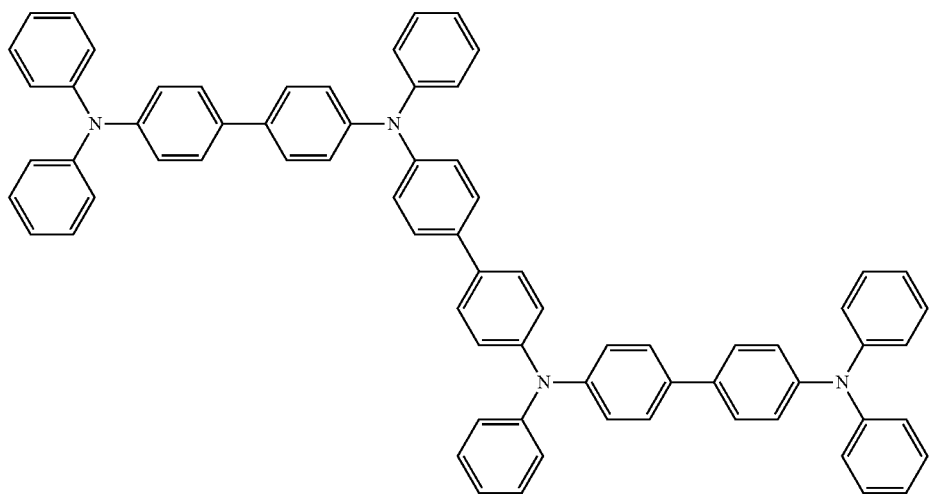 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1]
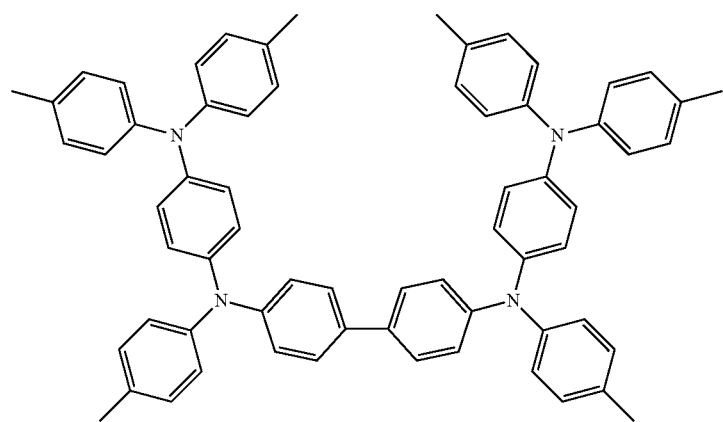
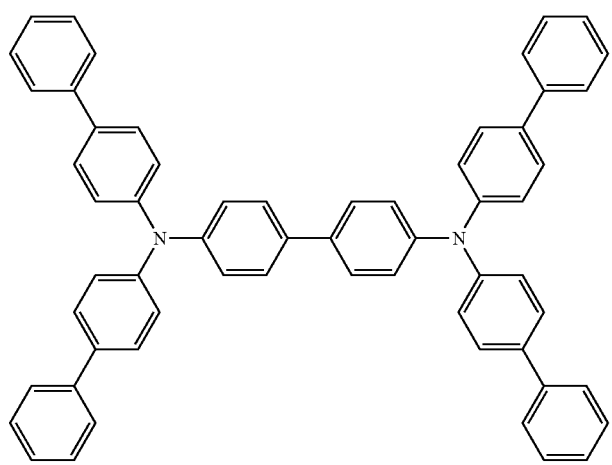 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1]

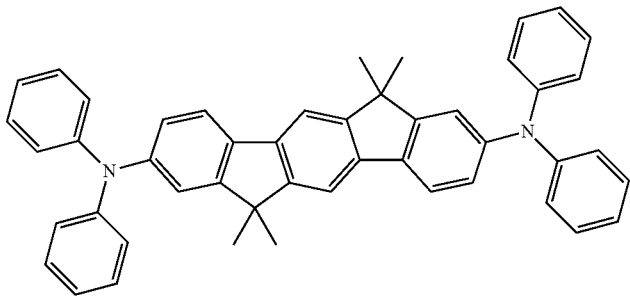 [SMILES: CC1(C)c2cc(N(c3ccccc3)c3ccccc3)ccc2-c2cc3c(cc21)-c1ccc(N(c2ccccc2)c2ccccc2)cc1C3(C)C]
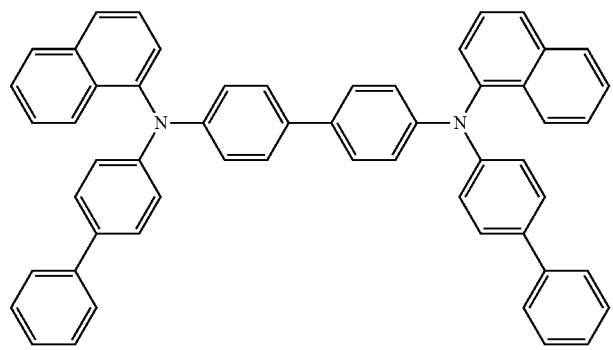 [SMILES: c1ccc(-c2ccc(N(c3ccc(-c4ccc(N(c5ccc(-c6ccccc6)cc5)c5cccc6ccccc56)cc4)cc3)c3cccc4ccccc34)cc2)cc1]
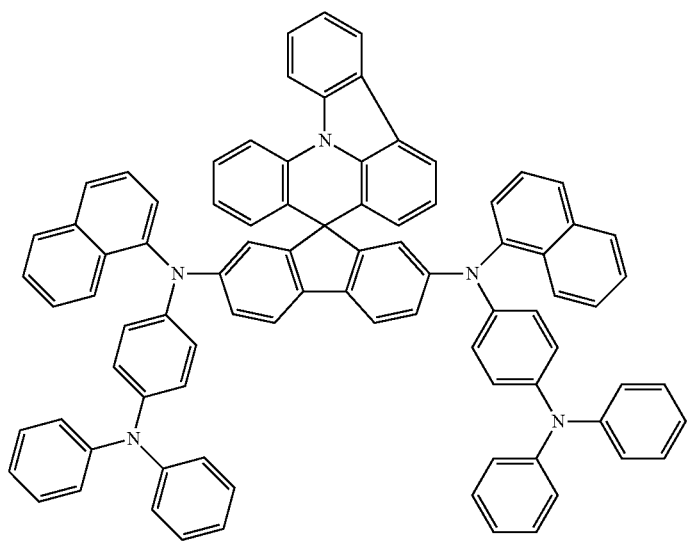 [SMILES: c1ccc(N(c2ccccc2)c2ccc(N(c3ccc4c(c3)C3(c5cc(N(c6ccc(N(c7ccccc7)c7ccccc7)cc6)c6cccc7ccccc67)ccc5-4)c4ccccc4-n4c5ccccc5c5cccc3c54)c3cccc4ccccc34)cc2)cc1]
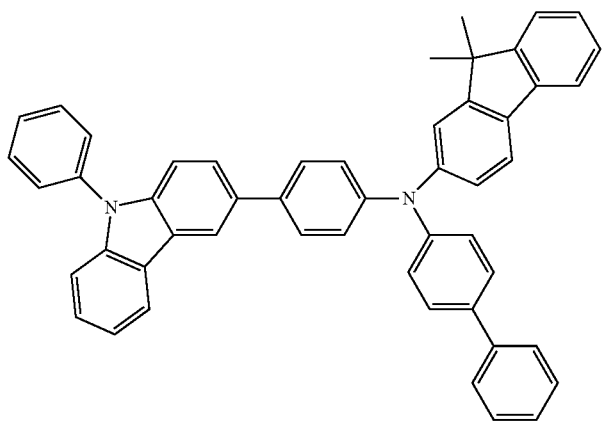 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag or Ba/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (O—SC) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

Preference is furthermore given to an organic electroluminescent device comprising one or more of the compounds according to the invention, characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it should be noted that the initial pressure may also be lower, for example less than $10^{-7}$ mbar.

Preference is likewise given to an organic electroluminescent device comprising one or more of the compounds according to the invention, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds, for example by long-chain alkyl groups or by oligophenyl groups.

The organic electroluminescent device can also be produced as a hybrid system by applying one or more layers from solution and applying one or more other layers by vapour deposition. Thus, for example, it is possible to apply an emitting layer comprising a compound of the formula (I) and a phosphorescent emitter compound from solution and to apply a hole-blocking layer and/or an electron-transport layer to this by vacuum vapour deposition. It is likewise possible to apply the emitting layer comprising a compound of the formula (I) and a phosphorescent emitter compound by vacuum vapour deposition and to apply one or more other layers from solution. Alternatively or in addition, it is also possible, for example, to apply an emitting layer from solution and to apply an electron-transport layer comprising a compound of the formula (I), optionally in combination with an organic alkali-metal compound, thereto by vacuum vapour deposition.

These processes are generally known to the person skilled in the art and can be applied by him without inventive step to organic electroluminescent devices comprising compounds of the formula (I).

The organic electroluminescent devices comprising one or more compounds of the formula (I) can be employed in accordance with the invention in displays, as light sources in lighting applications and as light sources in medical and/or cosmetic applications (for example photo-therapy).

The compounds according to the invention are distinguished by one or more of the following advantageous properties:

1. The compounds according to the invention have high charge-carrier mobility. It is preferably at values above $10^{-4}$ Vs/cm$^2$, particularly preferably at values above $10^{-3}$ Vs/cm$^2$. High charge-carrier mobility is highly desired, in particular, for use as electron-transport material and/or as hole-blocking material. It results in high values of the power efficiency of the electronic devices.

2. The compounds according to the invention have high stability. They can thus be sublimed without decomposition, meaning that high purity can be achieved. The high stability of the compounds has an advantageous effect on the lifetime and the operating data of the electronic devices which comprise the compounds.

3. The compounds according to the invention have a high glass-transition temperature. This has an advantageous effect on the film-formation properties of the materials and thus on the stability and the performance data of the devices according to the invention comprising the compounds.

The invention is now explained in greater detail by the following examples, without wishing to restrict it thereby. The person skilled in the art will be able to synthesise further compounds of the formula (I) and employ them in electronic devices using his general expert knowledge and the disclosure content of the present application.

USE EXAMPLES

Synthesis Example 1

4-[4-(10-Phenylanthracen-9-yl)phenyl]-6,7,11b-triazabenzo[c]fluorene

1st Step:

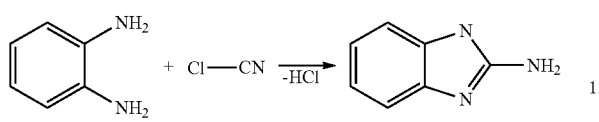

4000 ml of water and 648.0 g (6.0 mol) of o-phenylenediamine are initially introduced in a 6 l four-necked flask with mechanical stirrer, internal thermometer, dropping funnel and reflux condenser. Starting at room temperature, 369 g (6.3 mol) of cyanogen chloride are added dropwise from the dropping funnel over the course of 15 minutes with stirring in a cooling bath (acetone/dry ice), during which the temperature of the reaction mixture rises to an internal temperature of about 65° C. The pH is subsequently adjusted to about 9 using 550 g of 45% sodium hydroxide solution, and the mixture is cooled to 15° C. in the cooling bath with stirring. The solid is filtered off, rinsed with ice-water, and the 2-aminobenzimidazole is dried. Yield: 750 g (94%)

2nd Step:

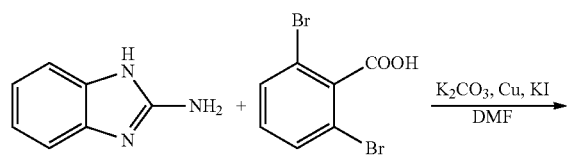

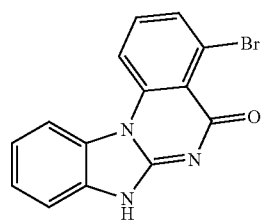

2-Aminobenzimidazole (22 g, 160 mmol) and 2,6-dibromobenzoic acid (44.8 g, 160 mmol) in 500 ml of N,N-dimethylformamide is stirred under reflux for 5 h with anhydrous potassium carbonate (27 g, 156 mmol) with 0.8 g of Ullmann copper and 0.01 g of potassium iodide in a 2 l four-necked flask with protective-gas inlet, reflux condenser and mechanical stirrer. After cooling, the reaction mixture is diluted with water and adjusted to pH 1 using 10% hydrochloric acid. The precipitate is filtered off with suction, washed with water and then recrystallised from N,N-dimethylformamide. Yield: 36.2 g (93%).

3rd Step:

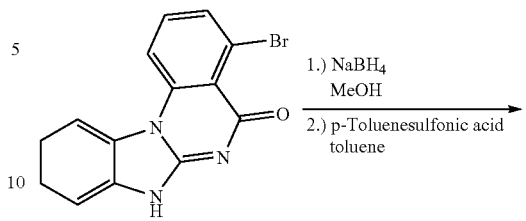

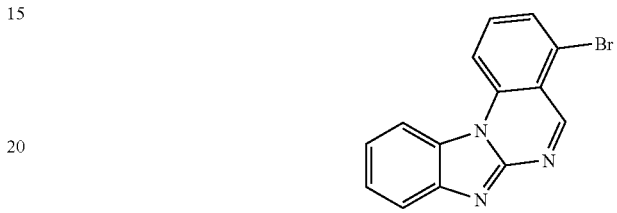

5 g (132 mmol) of NaBH$_4$ is added to a solution, stirred at room temperature, of 78.5 g (250 mmol) of the ketone in 2000 ml of ethanol in a 4 l four-necked flask with mechanical stirrer and protective-gas inlet. The reaction mixture is heated under reflux for 15 minutes and allowed to cool to room temperature. The solvent volume is reduced to less than one third, the mixture is transferred into a 10 l washing flask, sufficient water is added until the precipitate dissolves (about 5000 ml), and the mixture is extracted five times with a total of 4000 ml of dichloromethane. Washing of the combined organic phases twice with water, drying using sodium sulfate and removal of the solvent in vacuo gives the crude alcohol in quantitative yield. It is dissolved in 1500 ml of toluene and, after addition of 2-5% by weight of p-toluenesulfonic acid, heated in a water separator under a nitrogen atmosphere for 30 min. After cooling, the mixture is washed twice with saturated NaHCO$_3$ solution and once with water and dried using sodium sulfate. Removal of the solvent in a rotary evaporator and vacuum distillation of the residue gives the desired product. Yield: 59.6 g (80%)

4th Step:

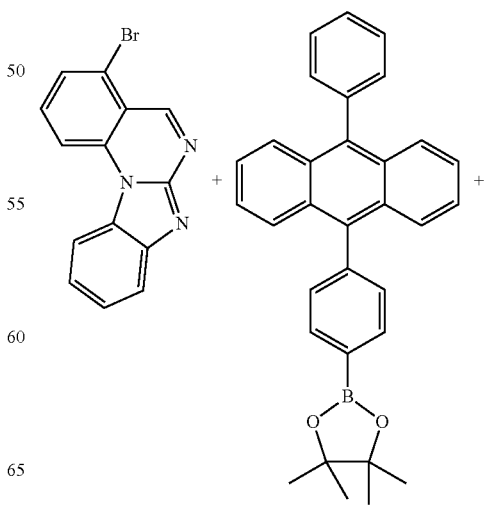

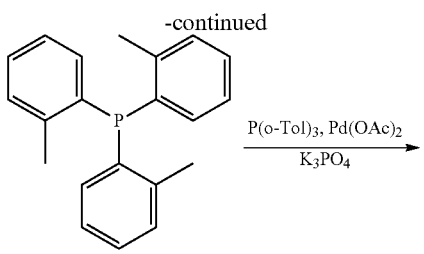

P(o-Tol)₃, Pd(OAc)₂
―――――――→
K₃PO₄

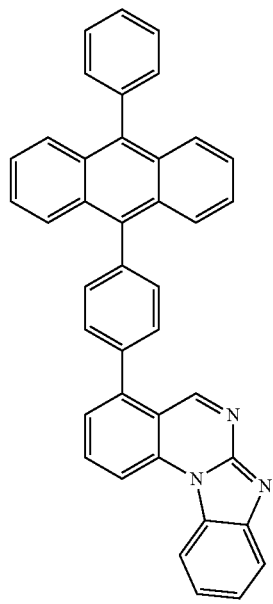

The product from the 3rd step (110.3 g, 0.37 mol), the boronic acid ester (187.1 g, 0.41 mol, purchased from MiguelAngel Chem) and potassium phosphate (165.5 g, 7.80 mol) are initially introduced in a flask. 1000 ml of toluene, 1000 ml of water and 415 ml of dioxane are subsequently added. The mixture is degassed by passing argon through it for 30 minutes with stirring. The phosphine (6.8 g, 22.28 mmol) is then added, the mixture is stirred briefly, and palladium(II) acetate (833 mg, 3.71 mmol) is then added. The mixture is subsequently heated under reflux (oil bath 120° C.) for 24 h. After cooling, glacial acetic acid/ethanol 1:1 (1200 ml) are added. The precipitated solid is filtered off with suction, rinsed 2× with about 250 ml of toluene, 2× with about 450 ml of water/ethanol mixture (ratio 1:1) and finally 2× with 550 ml of ethanol. The solid is extracted in 3 l of toluene in a Soxhlet extractor for 72 h and washed by stirring under reflux in degassed acetonitrile and degassed dichloromethane. The product is sublimed at 4×10⁻⁶ mbar and about 330° C. The purity according to HPLC is >99.9%. Yield: 111 g (55%); Tg (DSC)=161° C.

Synthesis Example 2

7,9-Diphenanthren-9-yl-4-b,10,11-triazabenzo[b]-fluorene

1st Step:

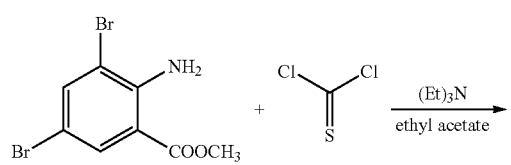

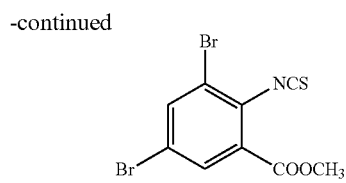

A mixture of thiophosgene (23 ml, 30 mmol) in 130 ml of ethyl acetate is cooled to −78° C. in a 500 ml four-necked flask with magnetic stirrer, internal thermometer, dropping funnel and protective-gas pass-over, and a mixture of triethylamine (8.4 ml, 60 mmol) in 80 ml of ethyl acetate is added dropwise over the course of 30 minutes with vigorous stirring. After a further 10 minutes, a solution of methyl 3,5-dibromo-2-aminobenzoate (8.4 g, 27.3 mmol) in 80 ml of ethyl acetate is added to the reaction mixture over the course of 30 minutes, and the mixture is stirred at room temperature for 12 h. The reaction mixture is diluted with 100 ml of ethyl acetate and washed successively with water and sat. NaCl solution and dried over MgSO₄. The solvent is distilled off. Column chromatography (eluent: hexane/toluene 9:1) gives the desired arylisothiocyanate ester. Yield: 8.7 g (91%)

2nd Step:

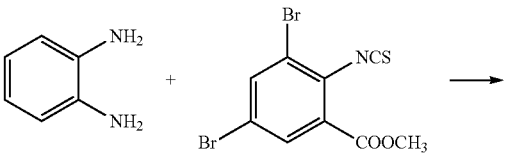

Arylisothiocyanate ester (54.4 g, 155 mmol) in 800 ml of dichloromethane is added dropwise over the course of 30 minutes to a solution of o-phenylenediamine (17.6 g, 163 mmol) in dichloromethane (800 ml), and the mixture is stirred overnight. Diisopropylcarbodiimide (DIC, 69.1 ml, 465 mmol) is then added, and the mixture is stirred for 18 h. The solvent is removed, and the residue is recrystallised in dichloromethane/hexane. The solid (a mixture of about 60% of benzimidazole ester and 40% of benzimidazoquinazoline) is dissolved in dioxane and heated consecutively in portions in each case for 26 minutes at 160° C. together with barium hydroxide (total: 250 g, 815 mmol) in a sealed reaction vessel in the microwave reactor.

The solid formed is washed successively with aqueous NH₄Cl solution, water, dioxane, dichloromethane and ethyl acetate. Yield: 58.5 g (96%)

3rd Step:

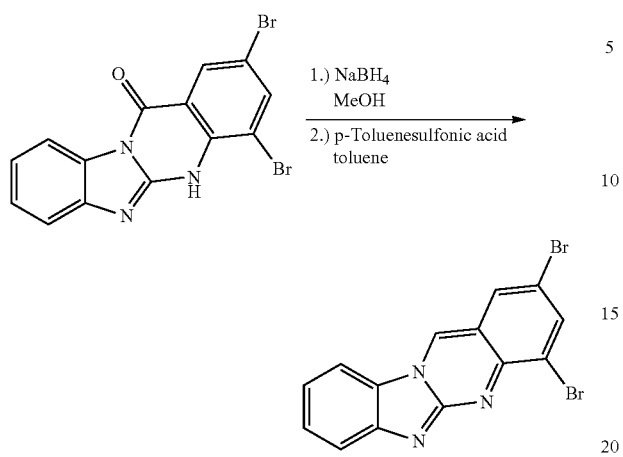

5 g (132 mmol) of NaBH$_4$ is added to a solution, stirred at room temperature, of 78.5 g (250 mmol) of the ketone in 2000 ml of ethanol in a 4 liter four-necked flask with mechanical stirrer and protective-gas inlet. The reaction mixture is refluxed for 15 minutes and allowed to cool to room temperature. The solvent volume is reduced to less than one third, the mixture is transferred into a 10 liter washing flask, sufficient water is added until the precipitate dissolves (about 5000 ml), and the mixture is extracted five times with a total of 4000 ml of dichloromethane. Washing of the combined organic phases twice with water, drying using sodium sulfate and removal of the solvent in vacuo gives the crude alcohol in quantitative yield. It is dissolved in 1500 ml of toluene and, after addition of 2-5% by weight of p-toluenesulfonic acid, heated in a water separator under a nitrogen atmosphere for 30 min. After cooling, the mixture is washed twice with saturated NaHCO$_3$ solution and once with water and dried using sodium sulfate. Removal of the solvent in a rotary evaporator and vacuum distillation of the residue gives the desired product. Yield: 59.6 g (80%)

4th Step:

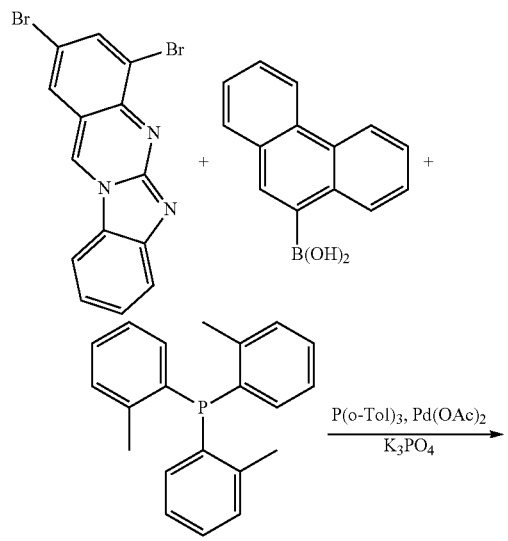

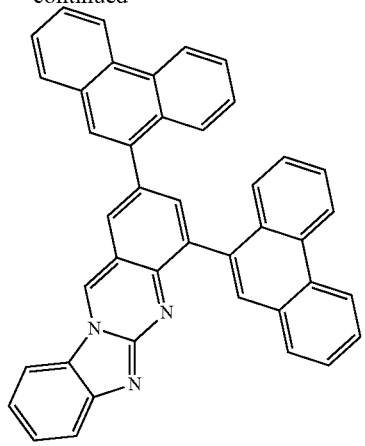

The bromide (139.5 g, 0.37 mol), the boronic acid ester (153.8 g, 0.80 mol) and the potassium phosphate (165.5 g, 7.80 mol) are initially introduced, then 1000 ml of toluene, 1000 ml of water and 415 ml of dioxane are added. The mixture is degassed by passing argon through it for 30 minutes with stirring. The phosphine (6.8 g, 22.28 mmol) is then added, the mixture is stirred briefly, the palladium(II) acetate (833 mg, 3.71 mmol) is then added. The mixture is subsequently heated under reflux (oil bath 120° C.) for 24 hours. After cooling, glacial acetic acid/ethanol 1:1 (1200 ml) is added. The precipitated solid is filtered off with suction, rinsed 2× with about 250 ml of toluene, 2× with about 450 ml of water/ethanol mixture (ratio 1:1) and finally 2× with 550 ml of ethanol. The solid is extracted in 3 l of toluene in a Soxhlet extractor for 72 h and washed by stirring under reflux in degassed acetonitrile and degassed dichloromethane. The product is then recrystallised 2× from dioxane. The product is sublimed at 2.5×10$^{-6}$ mbar and about 340° C. The purity according to HPLC is >99.9%. 116 g (55%) of 7,9-diphenanthren-9-yl-4-b,10,11-triazabenzo[b]fluorene are obtained as pale-yellow solid. Tg (DSC)=140° C.

Synthesis Example 3

10-Benzo[4,5]imidazo[1,2-c]quinazolin-4-yl-12,12-dimethyl-10,12-dihydro-10-azaindeno[2,1-b]fluorene 1st Step:

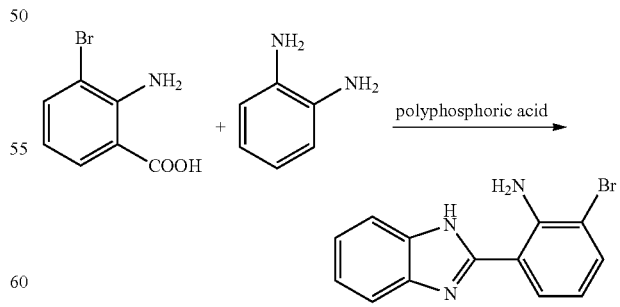

3-Bromoanthranilic acid (2-amino-3-bromobenzoic acid, 43.2 g, 0.2 mol) and o-phenylenediamine (21.6 g, 0.2 mol) in 400 ml of polyphosphoric acid are heated at 250° C. for 4-5 hours with stirring in a 4 l four-necked flask with mechanical stirrer, internal thermometer and reflux condenser. The reaction mixture is then cooled to 100° C., 2000 ml of ice-water are stirred in with vigorous stirring, and the pH is adjusted to 8-9 using 50% NaOH solution. The precipitate formed is filtered off, washed with water until neutral and recrystallised from an ethanol/water mixture (1:1). Yield: 19 g (33%)

2nd Step:

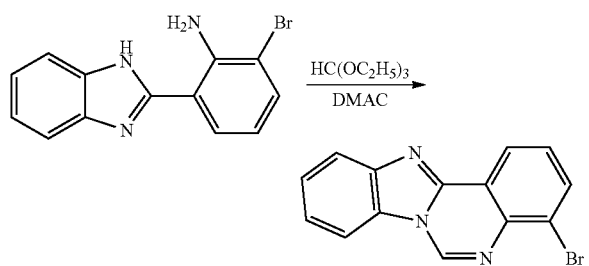

2-(2-Amino-3-bromophenyl)benzimidazole (57.6 g, 200 mmol) in 100 ml of triethyl orthoformate and 100 ml of N,N-dimethylacetamide (DMAC) is stirred under reflux for 4 hours in a 500 ml four-necked flask with protective-gas inlet, reflux condenser and mechanical stirrer. After cooling, the precipitate formed is filtered off with suction and then recrystallised from chloroform/water (1:1). Yield: 51.8 g (87%).

3rd Step:

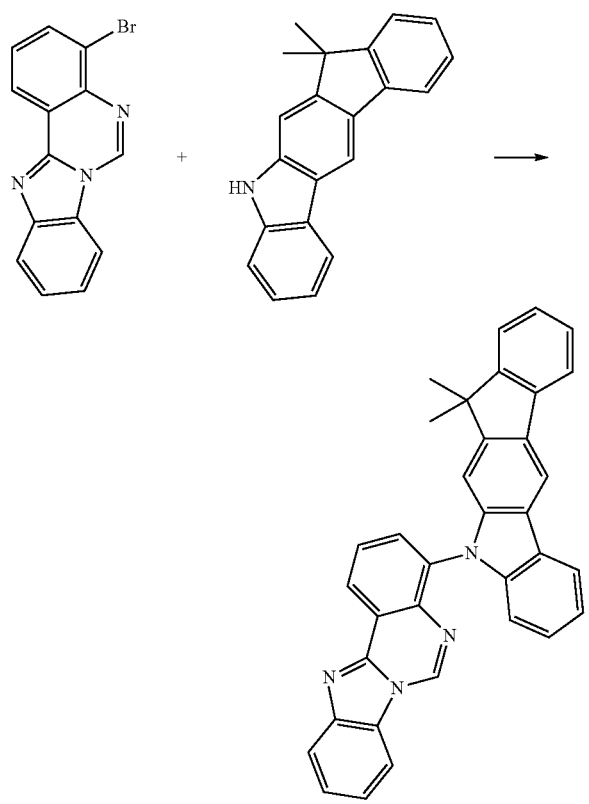

41.4 g (138 mmol) of the bromide, 37.5 g (132 mmol) of 12,12-dimethyl-10,12-dihydro-10-azaindeno[2,1-b]fluorene and potassium phosphate (84.2 g, 396 mmol) are dissolved in 750 mol of o-xylene and degassed in a 500 ml four-necked flask with protective-gas inlet, reflux condenser and mechanical stirrer. 1.08 g of 2-(dicyclohexylphosphino)-2',6'-methoxy-biphenyl (S-Phos, Aldrich) and 300 mg (1.3 mmol) of palladium acetate is then added, and the mixture is heated under reflux for 12 h. The mixture is cooled, poured into 1 l of water, and the org. phase is dried using $MgSO_4$. The solvent is removed, and the residue is recrystallised 2× from dioxane and extracted 1× with toluene in a Soxhlet extractor. The product is sublimed at $2 \times 10^{-6}$ mbar and about 350° C., giving 25.6 g (39%) of 10-benzo-[4,5]imidazo[1,2-c]quinazolin-4-yl-12,12-dimethyl-10,12-dihydro-10-azaindeno[2,1-b]fluorene as yellow solid. The purity according to HPLC is >99.9%. Tg (DSC)=142° C.

Device Examples

Production of OLEDs

OLEDs according to the invention and OLEDs in accordance with the prior art are produced by a general process in accordance with WO 04/058911, which is adapted to the circumstances described here (layer-thickness variation, materials used).

The results for various OLEDs are presented in the following Examples 1 to 14 (see Tables 1 and 2). Glass plates coated with structured ITO (indium tin oxide) in a thickness of 150 nm are coated with 20 nm of PEDOT (poly(3,4-ethylenedioxy-2,5-thiophene, purchased from H. C. Starck, Goslar, Germany, applied by spin coating from water) for improved processing. These coated glass plates form the substrates to which the OLEDs are applied. The OLEDs have in principle the following layer structure: substrate/hole-transport layer (HTL)/optional interlayer (IL)/electron-blocking layer (EBL)/emission layer (EML)/optional hole-blocking layer (HBL)/electron-transport layer (ETL)/optional electron-injection layer (EIL) and finally a cathode. The cathode is formed by an aluminium layer with a thickness of 100 nm. The precise structure of the OLEDs is shown in Table 1. The materials used for the production of the OLEDs are shown in Table 3.

All materials are applied by thermal vapour deposition in a vacuum chamber. The emission layer here always consists of at least one matrix material (host material) and an emitting dopant (emitter), with which the matrix material or matrix materials is admixed in a certain proportion by volume by co-evaporation. An expression such as H1:SEB1 (95%:5%) here means that material H1 is present in the layer in a proportion by volume of 95% and SEB1 is present in the layer in a proportion by volume of 5%. The electron-transport layer may also analogously consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminance characteristic lines (IUL characteristic lines), and the lifetime are determined. The lifetime is defined as the time after which the luminous density has dropped to a certain proportion from a certain initial luminous density $I_0$. The expression LD50 means that the lifetime given is the time by which the luminous density has dropped to $0.5 \cdot I_0$ (to 50%), i.e. from, for example, 6000 cd/m² to 3000 cd/m².

The compounds according to the invention can be employed, inter alia, as matrix materials (host materials) for phosphorescent dopants. Compound H2 according to the invention is used here. The comparison used in accordance with the prior art is compound H3. The use of the compounds according to the invention results in higher efficiency and a longer lifetime (Ex. 12-14) and in a low operating voltage, particularly in combination with electron conductors according to the invention (ETM2, Ex. 14).

The compounds are furthermore suitable as electron conductors in fluorescent devices. OLEDs comprising the blue-emitting dopant SEB-1 and compounds ETM2 and ETM3 according to the invention are shown. The results for the OLEDs are summarised in Table 2. Ex. 1-3 show OLEDs comprising materials in accordance with the prior art and serve as comparative examples. OLEDs 6-11 according to the invention exhibit the advantages on use of compounds ETM2 and ETM3 according to the invention. Devices in which the charge-transport materials according to the invention are used exhibit a lower operating voltage and a longer lifetime.

TABLE 1

Structure of the OLEDs

| Ex. | HTL Thickness | IL Thickness | EBL Thickness | EML Thickness | ETL Thickness | EIL Thickness |
|---|---|---|---|---|---|---|
| 1 (comp.) | HTM1 140 nm | HIL1 5 nm | NPB 20 nm | H1:SEB1 (95%:5%) 20 nm | ETM1:LiQ (50:50) 30 nm | |
| 2 (comp.) | HTM1 140 nm | HIL1 5 nm | NPB 20 nm | H1:SEB1 (95%:5%) 20 nm | ETM1:LiQ (25:75) 30 nm | |
| 3 (comp.) | HTM1 140 nm | HIL1 5 nm | NPB 20 nm | H1:SEB1 (95%:5%) 20 nm | ETM1 30 nm | LiQ 3 nm |
| 4 (comp.) | HTM1 20 nm | | NPB 20 nm | H3:TER1 (85%:15%) 30 nm | Alq 20 nm | LiF 1 nm |
| 5 (comp.) | HTM1 160 nm | | EBM1 20 nm | H3:TEG1 (90%:10%) 30 nm | ETM1:LiQ (50%:50%) 40 nm | |
| 6 | HTM1 140 nm | HIL1 5 nm | NPB 20 nm | H1:SEB1 (95%:5%) 20 nm | ETM2:LiQ (50:50) 30 nm | |
| 7 | HTM1 140 nm | HIL1 5 nm | NPB 20 nm | H1:SEB1 (95%:5%) 20 nm | ETM2:LiQ (25:75) 30 nm | |
| 8 | HTM1 140 nm | HIL1 5 nm | NPB 20 nm | H1:SEB1 (95%:5%) 20 nm | ETM2 30 nm | LiQ 3 nm |
| 9 | HTM1 140 nm | HIL1 5 nm | NPB 20 nm | H1:SEB1 (95%:5%) 20 nm | ETM3:LiQ (50:50) 30 nm | |
| 10 | HTM1 140 nm | HIL1 5 nm | NPB 20 nm | H1:SEB1 (95%:5%) 20 nm | ETM3:LiQ (25:75) 30 nm | |
| 11 | HTM1 140 nm | HIL1 5 nm | NPB 20 nm | H1:SEB1 (95%:5%) 20 nm | ETM3 30 nm | LiQ 3 nm |
| 12 | HTM1 20 nm | | NPB 20 nm | H2:TER1 (85%:15%) 30 nm | Alq 20 nm | LiF 1 nm |
| 13 | HTM1 160 nm | | EBM1 20 nm | H2:TEG1 (90%:10%) 30 nm | ETM1:LiQ (50%:50%) 40 nm | |
| 14 | HTM1 160 nm | | EBM1 20 nm | H2:TEG1 (90%:10%) 30 nm | ETM2:LiQ (50%:50%) 40 nm | |

TABLE 2

Results for the OLEDs

| Ex. | Voltage [V] for 1000 cd/m2 | Efficiency [cd/A] at 1000 cd/m2 | Efficiency [lm/W] at 1000 cd/m² | CE x/y at 1000 cd/m² | | LT50 I = 6000 cd/m² |
|---|---|---|---|---|---|---|
| 1 (comp.) | 4.2 | 9.6 | 7.3 | 0.142 | 0.145 | 180 |
| 2 (comp.) | 5.1 | 7.3 | 4.5 | 0.142 | 0.147 | 490 |
| 3 (comp.) | 3.6 | 7.9 | 6.8 | 0.142 | 0.150 | 80 |
| 4 (comp.) | 4.7 | 7.1 | 4.7 | 0.69 | 0.31 | 420 |
| 5 (comp.) | 4.6 | 54 | 37 | 0.37 | 0.60 | 400* |
| 6 | 3.6 | 9.4 | 8.2 | 0.142 | 0.144 | 270 |
| 7 | 4.3 | 7.3 | 5.3 | 0.142 | 0.146 | 650 |
| 8 | 3.6 | 8.1 | 7.1 | 0.142 | 0.149 | 120 |
| 9 | 3.8 | 9.8 | 8.1 | 0.142 | 0.145 | 190 |
| 10 | 4.6 | 8.9 | 6.1 | 0.142 | 0.147 | 700 |
| 11 | 3.3 | 8.0 | 7.6 | 0.142 | 0.147 | 155 |

TABLE 2-continued
Results for the OLEDs
| Ex. | Voltage [V] for 1000 cd/m2 | Efficiency [cd/A] at 1000 cd/m2 | Efficiency [lm/W] at 1000 cd/m$^2$ | CE x/y at 1000 cd/m$^2$ | | LT50 I = 6000 cd/m$^2$ |
|---|---|---|---|---|---|---|
| 12 | 4.0 | 7.3 | 9.3 | 0.69 | 0.31 | 620 |
| 13 | 4.1 | 58 | 44 | 0.37 | 0.60 | 550* |
| 14 | 3.7 | 58 | 50 | 0.37 | 0.60 | 850* |
*For these devices, the lifetime LT80 from 4000 cd/m$^2$ was determined.
TABLE 3
Structural formulae of the materials used
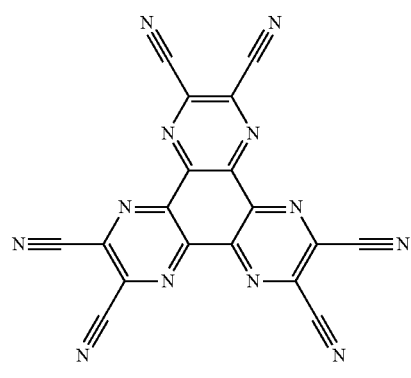
HIL1
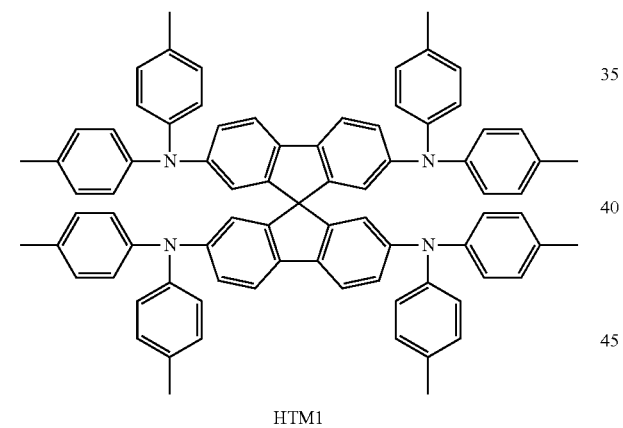
HTM1
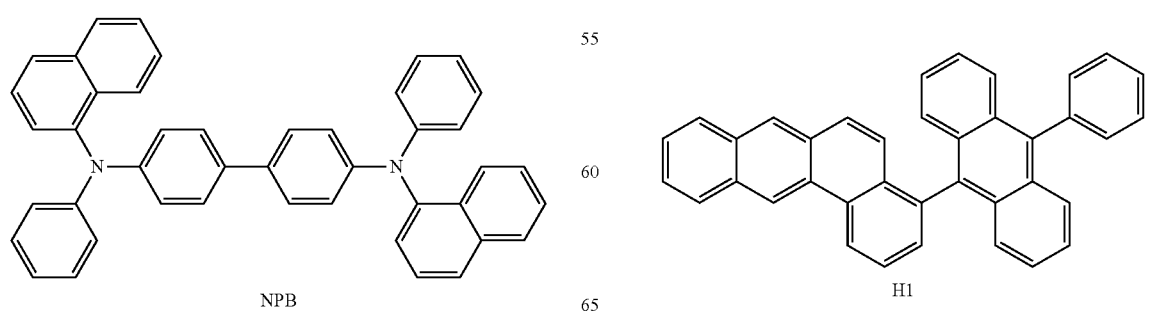
NPB
TABLE 3-continued
Structural formulae of the materials used
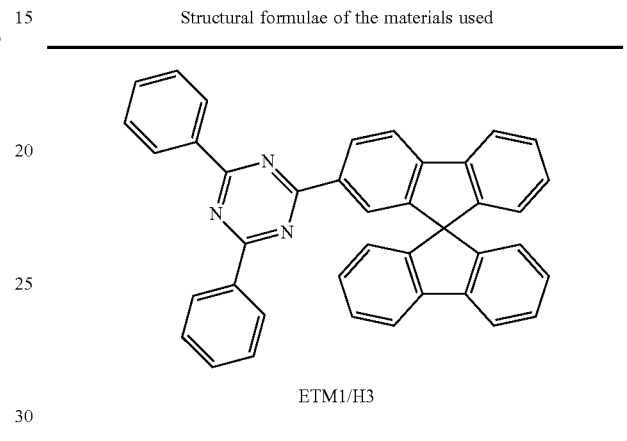
ETM1/H3
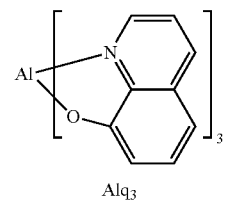
Alq$_3$
H1

TABLE 3-continued
Structural formulae of the materials used
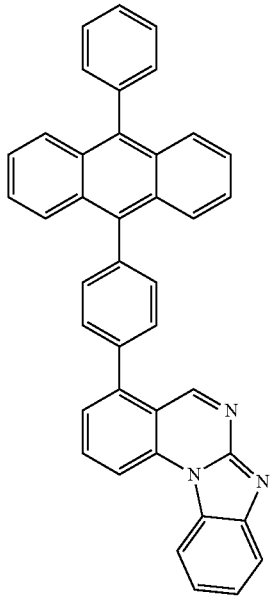
ETM2 (Synthesis Ex. 1)
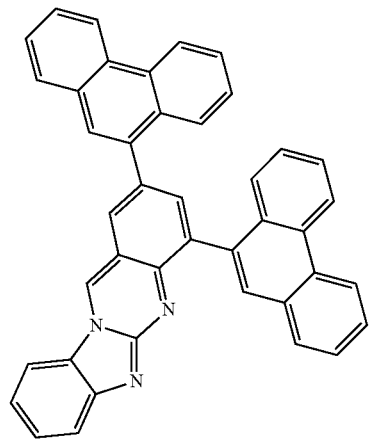
ETM3 (Synthesis Ex. 2)
TABLE 3-continued
Structural formulae of the materials used
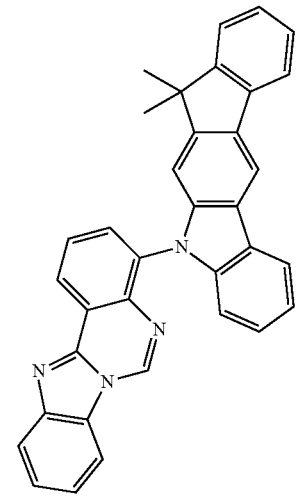
H2 (Synthesis Ex. 3)
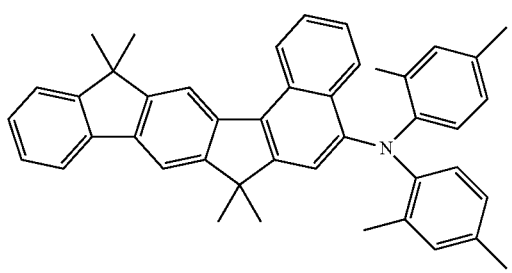
SEB1
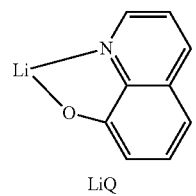
LiQ
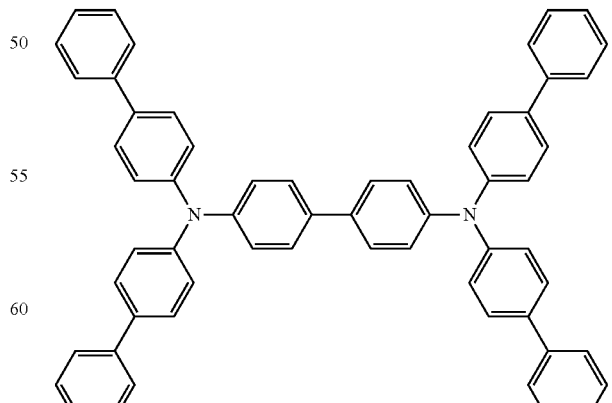
EBM1

TABLE 3-continued
Structural formulae of the materials used
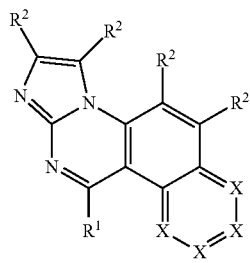
TEG1
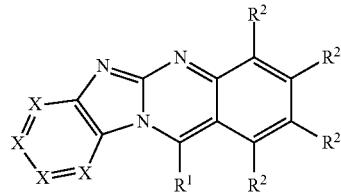
TER1
The invention claimed is:
1. A compound of the formula (I-1a), (I-1b), (I-1c), (I-1d), (I-2a), (I-2b), (I-2c), (I-2d), (I-3b) or (I-3d)
formula (I-1a)
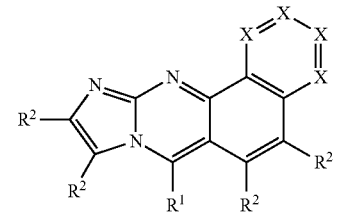
formula (I-1b)
formula (I-1c)
formula (I-1d)
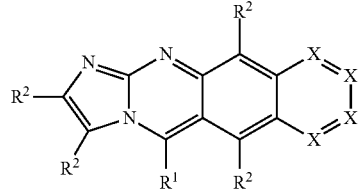
formula (I-2a)
formula (I-2b)
formula (I-2c)
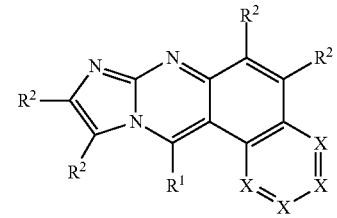
formula (I-2d)
formula (I-3b)
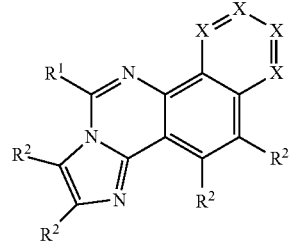
formula (I-3d)
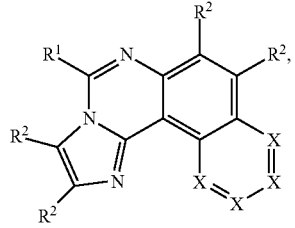

R¹ is H, D, F, Cl, Br, I, CHO, N(R³)₂, C(=O)R³, P(=O)(R³)₂, S(=O)R³, S(=O)₂R³, CR³=C(R³)₂, CN, NO₂, Si(R³)₃, B(OR³)₂, OS(=O)₂R³, SO₃H, C(=O)OR³, OR³, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by —R³C=CR³—, —C≡C—, Si(R³)₂, Ge(R³)₂, Sn(R³)₂, C=O, C=S, C=Se, C=NR³, P(=O)(R³), S=O, S(=O)₂, NR³, —O—, —S— or C(=O)NR³ and where one or more H atoms is optionally replaced by D, F, Cl, Br, I, CN or NO₂, and where, furthermore, R¹ is optionally linked to a group R² bonded in the 1,3-position adjacent to R¹ and may form a mono- or polycyclic, aliphatic or aromatic ring system;

R² is on each occurrence, identically or differently, H, D, F, Cl, Br, I, CHO, N(R³)₂, C(=O)R³, P(=O)(R³)₂, S(=O)R³, S(=O)₂R³, CR³=C(R³)₂, CN, NO₂, Si(R³)₃, B(OR³)₂, OS(=O)₂R³, SO₃H, C(=O)OR³, OR³, a straight-chain alkyl, alkoxy or thioalkyl group having 1 to 40 C atoms or a branched or cyclic alkyl, alkoxy or thioalkyl group having 3 to 40 C atoms or an alkenyl or alkynyl group having 2 to 40 C atoms, each of which is optionally substituted by one or more radicals R³, where one or more non-adjacent CH₂ groups is optionally replaced by —R³C=CR³—, —C≡C—, Si(R³)₂, Ge(R³)₂, Sn(R³)₂, C=O, C=S, C=Se, C=NR³, P(=O)(R³), S=O, S(=O)₂, NR³, —O—, —S— or C(=O)NR³ and where one or more H atoms is optionally replaced by D, F, Cl, Br, I, CN or NO₂, or an aromatic or heteroaromatic ring system having 5 to 60 aromatic ring atoms, which may in each case be substituted by one or more radicals R³, and which is optionally condensed with the ring to which it is bonded, or an aryloxy or heteroaryloxy group having 5 to 60 aromatic ring atoms, which is optionally substituted by one or more radicals R³, or a combination of these systems, where two or more radicals R² is optionally linked to one another and may form a mono- or polycyclic, aliphatic or aromatic ring system, R³ is on each occurrence, identically or differently, H, D, F, Cl, Br, I, CHO, N(R⁴)₂, C(=O)R⁴, P(=O)(R⁴)₂, S(=O)R⁴, S(=O)₂R⁴, CR⁴=C(R⁴)₂, CN, NO₂, Si(R⁴)₃, B(OR⁴)₂, OS(=O)₂R⁴, SO₃H, C(=O)OR⁴, OR⁴, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, each of which is optionally substituted by one or more radicals R⁴, where one or more non-adjacent CH₂ groups is optionally replaced by —R⁴C=CR⁴—, —C≡C—, Si(R⁴)₂, Ge(R⁴)₂, Sn(R⁴)₂, C=O, C=S, C=Se, C=NR⁴, P(=O)(R⁴), S=O, S(=O)₂, NR⁴, —O—, —S— or C(=O)NR⁴ and where one or more H atoms is optionally replaced by D, F, Cl, Br, I, CN or NO₂, or an aromatic or heteroaromatic ring system having 5 to 30 aromatic ring atoms, which may in each case be substituted by one or more radicals R⁴, or an aryloxy or heteroaryloxy group having 5 to 30 aromatic ring atoms, which is optionally substituted by one or more radicals R⁴, or a combination of these systems, where two or more radicals R³ is optionally linked to one another and may form a mono- or polycyclic, aliphatic or aromatic ring system, R⁴ is on each occurrence, identically or differently, H, D, F or an aliphatic, aromatic and/or heteroaromatic organic radical having 1 to 20 C atoms, in which, in addition, one or more H atoms is optionally replaced by D or F; two or more identical or different substituents R⁴ here may also be linked to one another and form a mono- or polycyclic, aliphatic or aromatic ring system;

X is on each occurrence, identically or differently, CR³ or N, with the proviso that not more than two adjacent X are simultaneously equal to N;

and where at least one radical R² must be selected from the group comprising aromatic or heteroaromatic ring systems having 5 to 60 aromatic ring atoms, which may in each case be substituted by one or more radicals R³ and which is optionally condensed with the ring to which they are bonded, and fully conjugated alkenyl or alkynyl groups having 2 to 40 C atoms, which is optionally substituted by one or more radicals R³.

2. The compound according to claim 1, wherein the compound corresponds to one of the formulae (I-1e) to (I-1k), (I-2e) to (I-2k) and (I-3e), (I-3g) to (I-3k)

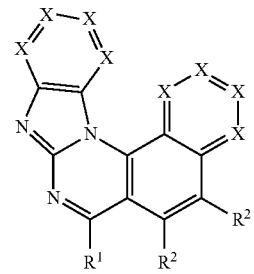

formula (I-1e)

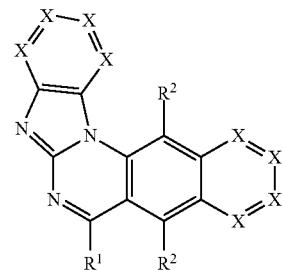

formula (I-1f)

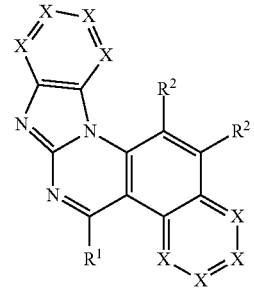

formula (I-1g)

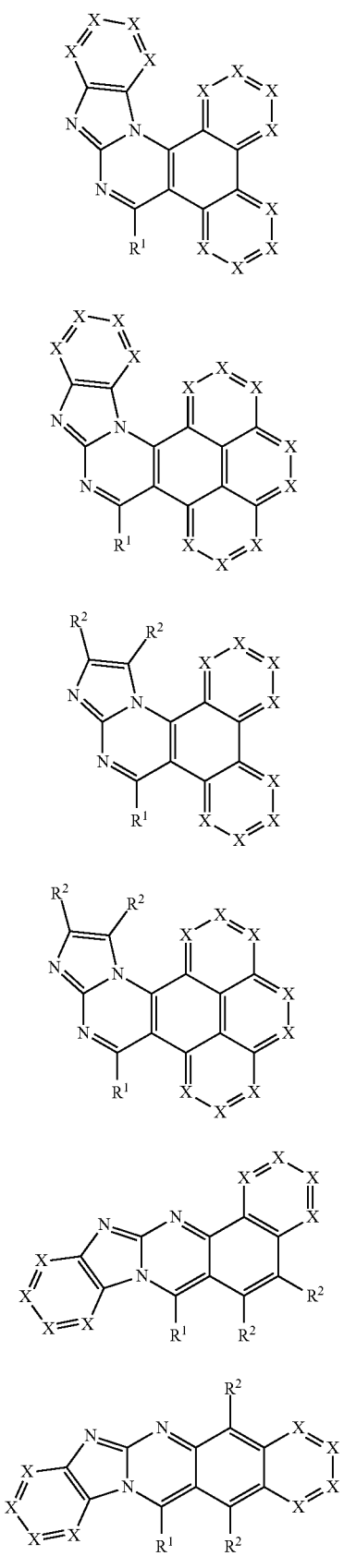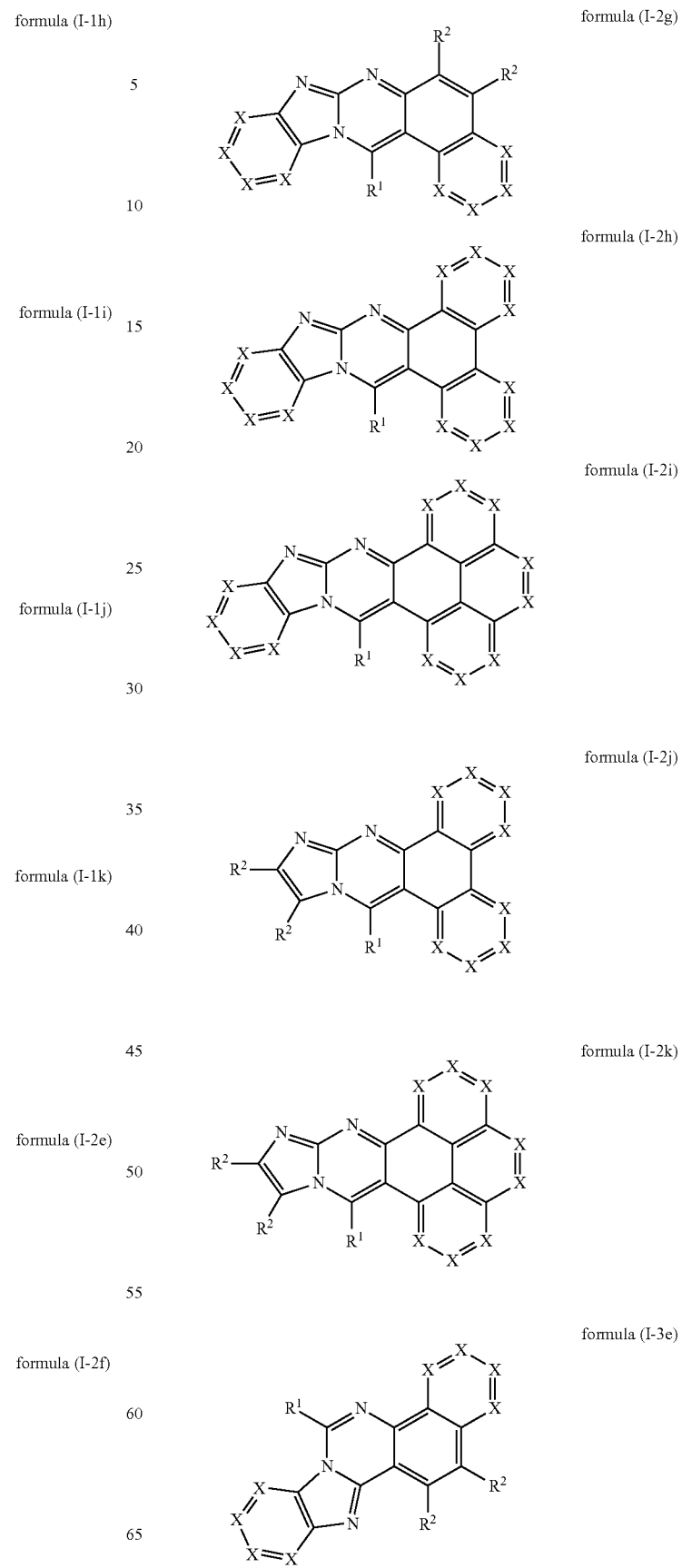

formula (I-3g)

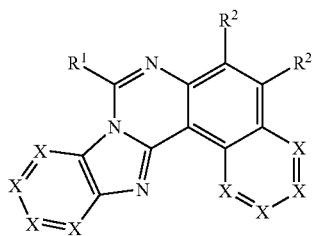

formula (I-3h)

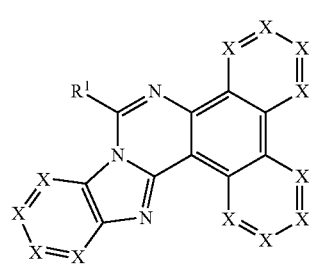

formula (I-3i)

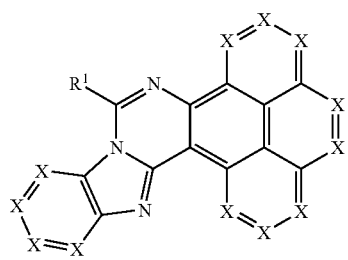

formula (I-3j)

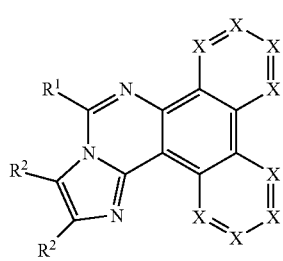

formula (I-3k)

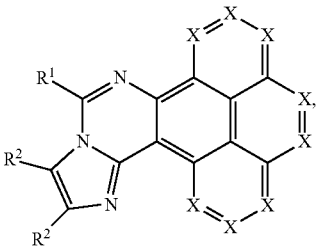

where $R^1$, $R^2$ and X are as defined in claim 1.

3. The compound according to claim 2, wherein X is equal to $CR^3$.

4. The compound according to claim 1, wherein the following applies to $R^1$:

$R^1$ is H, D, F, $N(R^3)_2$, $C(\!=\!O)R^3$, $CR^3\!=\!C(R^3)_2$, CN, $Si(R^3)_3$, $OR^3$, a straight-chain alkyl or alkoxy group having 1 to 10 C atoms, a branched or cyclic alkyl or alkoxy group having 3 to 10 C atoms or an alkenyl or alkynyl group having 2 to 10 C atoms, where the said groups may each be substituted by one or more radicals $R^3$ and where one or more adjacent or non-adjacent $CH_2$ groups is optionally replaced by $-\!C\!\equiv\!C\!-$, $R^3C\!=\!CR^3$, $Si(R^3)_2$, $C\!=\!O$, $C\!=\!NR^3$, $NR^3$, $-\!O\!-$, $-\!S\!-$ or $C(\!=\!O)NR^3$.

5. A process for the preparation of the compound according to claim 1, wherein the process includes one or more condensation reactions between one or more amino groups and one or more carbonyl or carboxyl functions with formation of a heterocyclic ring.

6. A formulation comprising at least one compound according to claim 1 and at least one solvent.

7. A mixture comprising at least one compound according to claim 1 and at least one phosphorescent emitter compound.

8. An electronic device which comprises the compound according to claim 1.

9. An organic electroluminescent device which comprises the compound according to claim 1.

10. The electronic device according to claim 8, wherein the device is an organic integrated circuit, an organic field-effect transistor, an organic thin-film transistor, an organic light-emitting transistor, an organic solar cell, an organic optical detector, an organic photoreceptor, an organic field-quench device, a light-emitting electrochemical cell, an organic laser diode or an organic electroluminescent device.

11. An organic electroluminescent device which comprises the compound according to claim 1 is employed as electron-transport material in an electron-transport layer and/or is employed as hole-blocking material in a hole-blocking layer and/or is employed as emitter material in an emitting layer and/or is employed as matrix material in an emitting layer.

* * * * *